United States Patent
Arslan et al.

(10) Patent No.: US 10,704,094 B1
(45) Date of Patent: Jul. 7, 2020

(54) MULTIPART REAGENTS HAVING INCREASED AVIDITY FOR POLYMERASE BINDING

(71) Applicant: ELEMENT BIOSCIENCES, INC., San Diego, CA (US)

(72) Inventors: Sinan Arslan, San Diego, CA (US); Chunhong Zhou, San Diego, CA (US); Molly Min He, San Diego, CA (US); Matthew Kellinger, San Diego, CA (US); Adeline Huizhen Mah, San Diego, CA (US); Michael Previte, San Diego, CA (US); Lei Sun, San Diego, CA (US)

(73) Assignee: ELEMENT BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 16/740,357

(22) Filed: Jan. 10, 2020

Related U.S. Application Data

(63) Continuation-in-part of application No. 16/579,794, filed on Sep. 23, 2019, and a continuation-in-part of application No. PCT/US2019/061556, filed on Nov. 14, 2019, which is a continuation-in-part of application No. 16/363,842, filed on Mar. 25, 2019.

(60) Provisional application No. 62/897,172, filed on Sep. 6, 2019, provisional application No. 62/776,898, filed on Dec. 7, 2018, provisional application No. 62/767,343, filed on Nov. 14, 2018.

(51) Int. Cl.
| | |
|---|---|
| *C12Q 1/68* | (2018.01) |
| *C12Q 1/6869* | (2018.01) |
| *C12Q 1/6876* | (2018.01) |
| *G01N 33/543* | (2006.01) |
| *G01N 21/64* | (2006.01) |
| *C12N 9/12* | (2006.01) |

(52) U.S. Cl.
CPC ......... *C12Q 1/6876* (2013.01); *C12N 9/1241* (2013.01); *G01N 21/6428* (2013.01); *G01N 33/54306* (2013.01); *G01N 2021/6439* (2013.01)

(58) Field of Classification Search
CPC ......... C12Q 1/68; C12Q 1/6869; C07H 21/00
See application file for complete search history.

(56) References Cited

U.S. PATENT DOCUMENTS

| | | |
|---|---|---|
| 3,950,649 A | 4/1976 | Yonekubo |
| 4,222,743 A | 9/1980 | Wang |
| 5,184,021 A | 2/1993 | Smith |
| 5,422,712 A | 6/1995 | Ogino |
| 5,624,711 A | 4/1997 | Sundberg et al. |
| 6,210,891 B1 | 4/2001 | Nyren et al. |
| 6,287,874 B1 | 9/2001 | Hefti |
| 6,440,748 B1 | 8/2002 | Katerkamp et al. |
| 6,482,590 B1 | 11/2002 | Ullman et al. |
| 6,548,607 B2 | 4/2003 | Halverson et al. |
| 6,818,425 B2 | 11/2004 | Hjorleifsdottir et al. |
| 6,829,051 B2 | 12/2004 | Abe et al. |
| 6,833,246 B2 | 12/2004 | Balasubramanian |
| 7,030,383 B2 | 4/2006 | Babayoff et al. |
| 7,189,580 B2 | 1/2007 | Lapidus et al. |
| 7,264,934 B2 | 9/2007 | Fuller |
| 7,416,844 B2 | 8/2008 | Korlach et al. |
| 7,501,245 B2 | 3/2009 | Quake et al. |
| 7,611,669 B1 | 11/2009 | Crisanti et al. |
| 7,755,841 B2 | 7/2010 | Christenson et al. |
| 7,763,423 B2 | 7/2010 | Roitman et al. |
| 7,960,116 B2 | 6/2011 | Eid et al. |
| 8,039,817 B2 | 10/2011 | Feng et al. |
| 8,120,002 B2 | 2/2012 | Van Dijk et al. |
| 8,133,672 B2 | 3/2012 | Bjornson et al. |
| 8,142,599 B2 | 3/2012 | Sekar |
| 8,242,463 B2 | 8/2012 | Feng et al. |
| 8,257,954 B2 | 9/2012 | Clark et al. |
| 8,278,630 B1 | 10/2012 | Feng et al. |
| 8,399,196 B2 | 3/2013 | Hoser |
| 8,405,048 B2 | 3/2013 | Hayashi |
| 8,481,264 B2 | 7/2013 | Bjornson et al. |
| 8,530,164 B2 | 9/2013 | Patel et al. |
| 8,546,772 B2 | 10/2013 | Feng et al. |
| 8,586,947 B1 | 11/2013 | Feng et al. |
| 8,632,975 B2 | 1/2014 | Vander Horn et al. |

(Continued)

FOREIGN PATENT DOCUMENTS

| | | |
|---|---|---|
| WO | WO-9508000 A2 | 3/1995 |
| WO | WO-0018957 A1 | 4/2000 |

(Continued)

OTHER PUBLICATIONS

Ameringer et al. Ultrathin Functional Star PEG Coatings for DNA Microarrays. Biomacromolecules 6(4):1819-1823 (2005).

(Continued)

*Primary Examiner* — Ethan C Whisenant
(74) *Attorney, Agent, or Firm* — Wilson Sonsini Goodrich & Rosati

(57) ABSTRACT

Multivalent binding compositions including a particle-nucleotide conjugate having a plurality of copies of a nucleotide attached to the particle are described. The multivalent binding compositions allow one to localize detectable signals to active regions of biochemical interaction, e.g., sites of protein-protein interaction, protein-nucleic acid interaction, nucleic acid hybridization, or enzymatic reaction, and can be used to identify sites of base incorporation in elongating nucleic acid chains during polymerase reactions and to provide improved base discrimination for sequencing and array based applications.

30 Claims, 32 Drawing Sheets

(56) References Cited

U.S. PATENT DOCUMENTS

| | | | |
|---|---|---|---|
| 8,658,365 | B2 | 2/2014 | Bjornson et al. |
| 8,698,102 | B2 | 4/2014 | Feng et al. |
| 8,703,461 | B2 | 4/2014 | Peris et al. |
| 8,715,932 | B2 | 5/2014 | Su et al. |
| 9,068,220 | B2 | 6/2015 | Feng et al. |
| 9,255,258 | B2 | 2/2016 | Vander Horn et al. |
| 9,399,767 | B2 | 7/2016 | Peris et al. |
| 9,385,898 | B2 | 8/2016 | Feng et al. |
| 9,410,193 | B2 | 8/2016 | Makarov et al. |
| 9,546,398 | B2 | 1/2017 | Peter et al. |
| 9,593,315 | B2 | 3/2017 | Peris et al. |
| 9,605,310 | B2 | 3/2017 | Balasubramanian et al. |
| 9,765,310 | B2 | 9/2017 | Vander Horn et al. |
| 9,862,992 | B2 | 1/2018 | Nagasaki et al. |
| 9,914,961 | B2 | 3/2018 | Klapproth et al. |
| 9,944,924 | B2 | 4/2018 | Rigatti et al. |
| 9,944,984 | B2 | 4/2018 | Drmanac et al. |
| 10,150,992 | B2 | 12/2018 | Menchen et al. |
| 10,336,991 | B2 | 7/2019 | Peris et al. |
| 10,519,496 | B2 | 12/2019 | Balasubramanian et al. |
| 2002/0030811 | A1 | 3/2002 | Schindler |
| 2002/0102586 | A1 | 8/2002 | Ju et al. |
| 2002/0139936 | A1 | 10/2002 | Dumas |
| 2003/0152490 | A1 | 8/2003 | Trulson et al. |
| 2003/0175737 | A1 | 9/2003 | Schulein et al. |
| 2004/0005585 | A1 | 1/2004 | Bi et al. |
| 2004/0005697 | A1 | 1/2004 | Mahant et al. |
| 2004/0106121 | A1 | 6/2004 | Ugolin et al. |
| 2005/0100951 | A1 | 5/2005 | Pircher |
| 2006/0105453 | A1 | 5/2006 | Brenan et al. |
| 2007/0298006 | A1 | 12/2007 | Tomalia et al. |
| 2008/0171331 | A1 | 7/2008 | Drmanac |
| 2008/0242560 | A1 | 10/2008 | Gunderson et al. |
| 2009/0203531 | A1 | 8/2009 | Kurn |
| 2010/0311127 | A1 | 12/2010 | Piepenburg et al. |
| 2010/0311144 | A1 | 12/2010 | Peris et al. |
| 2011/0059865 | A1 | 3/2011 | Smith et al. |
| 2011/0251078 | A1 | 10/2011 | Rothberg et al. |
| 2011/0281741 | A1 | 11/2011 | Rothberg et al. |
| 2011/0301044 | A1 | 12/2011 | Feng et al. |
| 2013/0004949 | A1 | 1/2013 | Rearick |
| 2013/0016530 | A1 | 1/2013 | Lipcsei et al. |
| 2013/0165350 | A1 | 6/2013 | Kuimelis et al. |
| 2013/0338044 | A1 | 12/2013 | Liao et al. |
| 2014/0079923 | A1 | 3/2014 | George et al. |
| 2014/0080717 | A1 | 3/2014 | Li et al. |
| 2015/0023840 | A1 | 1/2015 | Kinz-Thompson et al. |
| 2016/0025744 | A1 | 1/2016 | Feldman et al. |
| 2016/0287152 | A1 | 10/2016 | Schwartz et al. |
| 2016/0369334 | A1 | 12/2016 | Zhou et al. |
| 2017/0191125 | A1 | 7/2017 | Vijayan et al. |
| 2017/0204459 | A1 | 7/2017 | Barany et al. |
| 2017/0369857 | A1 | 12/2017 | Vander Horn et al. |
| 2018/0023119 | A1 | 1/2018 | Adey et al. |
| 2018/0313782 | A1 | 11/2018 | Rothberg et al. |
| 2019/0048404 | A1 | 2/2019 | Dambacher |
| 2019/0119740 | A1 | 4/2019 | Ahn et al. |

FOREIGN PATENT DOCUMENTS

| | | | |
|---|---|---|---|
| WO | WO-2005111240 | A2 | 11/2005 |
| WO | WO-2010057185 | A1 | 5/2010 |
| WO | WO-2017087974 | A1 | 5/2017 |
| WO | WO-2019018366 | A1 | 1/2019 |
| WO | WO-2019231568 | A1 | 12/2019 |

OTHER PUBLICATIONS

Bergstrom et al. Reduction of Fibrinogen Adsorption on PEG-Coated Polystyrene Surfaces. J Biomed Mater Res. 26(6):779-790 (1992).

Booth et al. Efficiency of the Polymerase Chain Reaction. Chemical Engineering Science 65(17):4996-5006 (2010).

Chen et al. Layer-by-Layer-Assembled Healable Antifouling Films. Adv. Mater. 27(39):5882-5888 (2015).

Chin et al. Solid-Phase PCR for Rapid Multiplex Detection of *Salmonella* Spp. at the Subspecies Level, with Amplification Efficiency Comparable to Conventional PCR. Analytical and Bioanalytical Chemistry, 409(10):2715-2726 (2017).

Gabriel et al., Electrografting of poly(ethylene glycol) acrylate: a one-step strategy for the synthesis of protein-repellent surfaces. Agnewandte Chemie. 44(34):5505-5509 (2005).

Giovambattista et al., Effect of surface polarity on water contact angle and interfacial hydration structure. The Journal of Physical Chemistry B. 111(32):9581-9587 (2007).

Godawat et al., Characterizing hydrophobicity of interfaces by using cavity formation, solute binding, and water correlations. Proceedings of the National Academy of Sciences of the United States of America. 160(36):15119-15124 (2009).

Guttenberg et al. Planar chip device for PCR and hybridization with surface acoustic wave pump. Lab on a Chip 5(3):308-317 (2005).

Harbers et al. A functionalized poly(ethylene glycol)-based bioassay surface chemistry that facilitates bio-immobilization and inhibits non-specific protein, bacterial, and mammalian cell adhesion. Chem Mater 19(18):4405-4414 (2007).

Heather et al. The Sequence of Sequencers: The History of Sequencing DNA. Genomics 107:1-8 (2016).

Joung et al. Hyper-Branched Poly(poly(ethylene glycol)methacrylate)-Grafted Surfaces by Photo-Polymerization with Iniferter for Bioactive Interfaces. Acta Biomater. 4(4):960-966 (2008).

Kumar et al., Patterned Self-Assembled Monolayers and Meso-Scale Phenomena. Accounts of Chemical Research. 28(5): 219-226 (1995).

Linnes et al. Polyethersulfone improves isothermal nucleic acid amplification compared to current paper-based diagnostics. Biomed Microdevices 18(2):30 (2016).

Lou et al. Increased amplification efficiency of microchip-based PCR by dynamic surface passivation. Biotechniquest 36(2):48-252 (2004).

Lu et al., Thermal properties and surface energy characteristics of interpenetratingpolyacrylate and polybenzoxazine networks. Polymer. 49(22):4852-4860 (2008).

Ma et al. Molecular Crowding Effects on Microgel-Tethered Oligonucleotide Probes. Langmuir 32(25):6551-6558 (2016).

Ma et al. Solid-Phase Nucleic Acid Sequence-Based Amplification and Length-Scale Effects during RNA Amplification. Anal Chem. 90(11):6532-6539 (2018).

Mardis. Next-Generation DNA Sequencing Methods. Annu Rev Genomics Hum Genet 9:387-402 (2008).

Mechref et al. Fused-Silica Capillaries with Surface-Bound Dextran Layer Crosslinked with Di-Epoxypolyethylene Glycol for Capillary Electrophoresis of Biological Substances at Reduced Electroosmotic Flow. Electrophoresis 16(4):617-624 (1995).

Palanisamy et al. Considerations of solid-phase DNA amplification. Bioconjug chem 21(4):690-695 (2010).

Pan et al., A simple procedure to improve the surface passivation for single molecule fluorescence studies. Physical Biology. 12(4):045006 (2015).

Schlapak et al. Dense Passivating Poly(ethylene glycol) Films on Indium Tin Oxide Substrates. Langmuir 23(20):10244-10253 (2007).

Schlapak et al., Selective protein and DNA adsorption on PLL-PEG films modulated by ionic strength. Soft Matter. 5:613-621 (2009).

Xia et al. Minimizing the Surface Effect of PDMS-Glass Microchip on Polymerase Chain Reaction by Dynamic Polymer Passivation. J Chem Technol Biotechnol 82:33-38 (2007).

Zanoli et al. Isothermal Amplification Methods for the Detection of Nucleic Acids in Microfluidic Devices. Biosensors 3:18-43 (2013).

Zhang et al. Microfluidic DNA amplification—a review. Anal Chim Acta 638(2):115-125 (2009).

Zhang et al. Miniaturized PCR chips for nucleic acid amplification and analysis: latest advances and future trends. Nucleic Acids Res 35(13):4223-4237 (2007).

Zhang et al., Effects of Polyethylene Glycol on DNA Adsorption and Hybridization on Gold Nanoparticles and Graphene Oxide. Langmuir. 28(40): 14330-14337 (2012).

(56) References Cited

OTHER PUBLICATIONS

Zhong et al. Enhancing the specificity of polymerase chain reaction by graphene oxide through surface modification: zwitterionic polymer is superior to other polymers with different charges. Int J Nanomedicine 11:5989-6002 (2016).

Definition of clonal amplification provided by qiagen.com [retrieved on Mar. 6, 2020].

Heller. DNA microarray technology: devices, systems, and applications. Annu. Rev. Biomed. Eng. 4:129-53 (2002).

Ju et al. Four-Color DNA Sequencing by Synthesis Using Cleavable Fluorescent Nucleotide Reversible Terminators, PNAS USA 103:19635-19640 (2006).

PCT/US2019/061556 International Search Report and Written Opinion dated Apr. 2, 2020.

MULTIPART REAGENTS HAVING INCREASED AVIDITY FOR POLYMERASE BINDING

CROSS-REFERENCE

This application is a continuation-in-part of U.S. application Ser. No. 16/579,794, filed on Sep. 23, 2019, which claims the benefit of U.S. Provisional Application No. 62/897,172, filed on Sep. 6, 2019; and is a continuation-in-part of PCT/US2019/061556, filed Nov. 14, 2019, which is a continuation-in-part of U.S. application Ser. No. 16/363,842, filed Mar. 25, 2019, which claims the benefit of U.S. Provisional Application No. 62/767,343, filed on Nov. 14, 2018, and of U.S. Provisional Application No. 62/776,898, filed on Dec. 7, 2018, each of which is incorporated herein by reference in its entirety.

BACKGROUND

A variety of DNA sequencing methodologies have been developed and commercialized over the past two decades (see, for example, E. Mardis (2008), "Next-Generation DNA Sequencing Methods", Annu. Rev. Genomics Hum. Genet. 9:387-402; and J. Heather and B. Chain, (2016), "The Sequence of Sequencers: The History of Sequencing DNA", Genomics 107:1-8 for recent reviews). Many "second generation" and "third generation" sequencing technologies utilize a massively parallel, cyclic array approach to sequencing-by-synthesis (SBS), in which accurate decoding of a single-stranded template oligonucleotide sequence tethered to a solid support relies on successfully classifying signals that arise from the stepwise addition of A, G, C, and T nucleotides by a polymerase to a complementary oligonucleotide strand. These methods typically require the oligonucleotide template to be modified with a known adapter sequence of fixed length, affixed to a solid support in a random or patterned array by hybridization to surface-tethered probes of known sequence that is complementary to that of the adapter sequence, and then probed using, for example, a single molecule (non-amplified), synchronous sequencing-by-synthesis (smSBS) approach (e.g., the Helicos technology), or a single molecule, asynchronous sequencing-by-synthesis (smASBS) approach (e.g., the Pacific Biosciences technology). In the smSBS approach, terminator nucleotides encoded with fluorescent tags are used, such that a replication enzyme can only incorporate a single base per cycle. The Helicos technology, for example, used a single fluorescent tag and a sequential introduction of A, G, C, T was performed—once base per cycle. During each cycle, an imaging step was performed to classify the correct 'base" for each single molecule template on an array. Following the imaging steps, the reversibly-linked tags are removed, such that the replicating enzyme (polymerase) can incorporate the next templating base. These cycles are repeated many times to eventually decode the template oligonucleotide strands on the random array and determine their respective sequences.

While successful, the cyclic array approach has generally suffered from two fundamental inadequacies: (i) the cycle times for addition of each successive nucleotide to the complementary strand are long, and (ii) the signals arising from the stepwise addition of single nucleotides are weak (typically detected through the use of fluorescent labels and fluorescence imaging techniques) and exhibit low contrast-to-noise ratios (CNRs) as will be discussed in more detail below, and therefore require long imaging times using costly instrumentation comprising high precision optics to achieve accurate base-calling.

Attempts to address the cycle time issue for cyclic array sequencing approaches have been made, for example, through the advent of single molecule asynchronous sequencing-by-synthesis (smASBS) approaches, e.g., the Pacific Biosciences technology in which four spectrally-distinct fluorescent tags are linked to the respective A, G, C, and T nucleotides, the addition of which can then be classified in "real-time". In this approach, all four labeled nucleotides are introduced simultaneously and images are acquired during the entire strand replication process. Each position in the sequence is classified as 'A', 'G', 'C', and 'T' based on the spectrum of the detected light. Here, the cycle times can theoretically be as fast as the polymerase-catalyzed replication rate, but the trade-off is decreased CNR, thereby introducing classification errors that ultimately lead to diminished accuracy, and putting greater reliance on high precision optics and costly instrumentation.

Attempts to address the signal limitations in some cyclic array sequencing approaches (i.e., non-single molecule approaches) have been made by incorporating an amplification step in the process. Solid-phase amplification of template DNA molecules tethered to a solid support in a random or patterned array increases the number of copies of the target to be sequenced, such that the signal arising from a "colony" of replicate template molecules upon step-wise addition of detectable bases to their respective complementary strands can be classified as 'A', 'G', 'C', or 'T'. The probability of successful classification (and thus the accuracy of base-calling) is dependent on the respective CNR during each detection event, which is often limiting.

Thus, there is a need for improved solid supports and solid phase amplification methods for nucleic acid sequencing that will increase the magnitude of base addition signals, decrease non-specific background signals, and thus improve CNR, thereby improving the accuracy of base-calling, potentially shortening cycle times, and reducing the dependence of the sequencing process on high precision optics and costly instrumentation.

SUMMARY

Some embodiments relate to a method of performing nucleic acid sequence determination, the method comprising: a) providing a surface; wherein the surface comprises: i) a substrate; ii) at least one hydrophilic polymer coating layer; iii) a plurality of oligonucleotide molecules attached to at least one hydrophilic polymer coating layer; and iv) at least one discrete region of the surface that comprises a plurality of clonally-amplified sample nucleic acid molecules immobilized to the plurality of attached oligonucleotide molecules, wherein the plurality of immobilized clonally-amplified sample nucleic acid molecules are present with a surface density of at least 5000 molecules/mm$^2$, b) performing a nucleic acid amplification reaction on sample nucleic acid molecules prior to or after annealing them to the plurality of oligonucleotide molecules; and c) performing at least a single nucleotide binding or incorporation reactions, wherein the nucleotides are labeled with a detectable tag. In some embodiments, the method further comprises detecting or characterizing the nucleotide based on the detectable tag.

Disclosed herein are surfaces comprising a substrate, at least one layer of a hydrophilic, low nonspecific binding (i.e., low background) coating, and a plurality of oligonucleotide molecules attached to at least one layer of hydrophilic, low-binding, low background coating.

The disclosed low nonspecific binding solid supports may be used for a variety of bioassays including, but are not limited to, DNA sequencing and genotyping. These supports comprise temperature- and chemically-stable functionalized substrates that withstand exposure to multiple solvent exchanges and temperature changes, and that confer low nonspecific binding properties throughout the duration of the assay. The disclosed supports may have some or all of the following properties:

1. Surface functionalization performed using any combination of polar protic, polar aprotic and/or nonpolar solvents that leads to an increase in the efficacy of bioassay performance by >5-fold (e.g., improvement in reaction rate and/or desired product formation, respectively) over traditional approaches.

2. Minimal contact angle measurement post functionalization (e.g., <35 degrees), which is maintained through successive solvent and temperature changes.

3. Low nonspecific binding of biomolecules versus specifically-bound molecules (e.g., greater than 1 specifically-bound molecule vs. <0.25 nonspecifically-bound molecule/region of interest). This can be translated directly to improved contrast to noise (CNR) when using any of a variety of detection methodologies.

Disclosed herein are surfaces comprising: a) a substrate; b) at least one hydrophilic polymer coating layer; c) a plurality of oligonucleotide molecules attached to at least one hydrophilic polymer coating layer; and d) at least one discrete region of the surface that comprises a plurality of clonally-amplified, sample nucleic acid molecules that have been annealed to the plurality of attached oligonucleotide molecules, wherein a fluorescence image of the surface exhibits a contrast-to-noise ratio (CNR) of at least 20.

In some embodiments, the fluorescence image of the surface exhibits a contrast-to-noise ratio (CNR) of at least 20 when the sample nucleic acid molecules or complementary sequences thereof are labeled with a Cyanine dye-3 (Cy3) fluorophore, and when the fluorescence image is acquired using an Olympus IX83 inverted fluorescence microscope with a 20×, 0.75 NA objective, a 532 nm light source, a bandpass and dichroic mirror filter set optimized for 532 nm excitation and Cy3 fluorescence emission, and a camera (e.g., Andor sCMOS, Zyla 4.2) under non-signal saturating conditions while the surface is immersed in a buffer (e.g., 25 mM ACES, pH 7.4 buffer).

In some embodiments, the fluorescence image of the surface exhibits a contrast-to-noise ratio (CNR) of at least 40. In some embodiments, the fluorescence image of the surface exhibits a contrast-to-noise ratio (CNR) of at least 60. In some embodiments, the substrate comprises glass. In some embodiments, the substrate comprises plastic. In some embodiments, the at least one hydrophilic polymer coating layer comprises PEG. In some embodiments, the surface further comprises a second hydrophilic polymer coating layer. In some embodiments, at least one hydrophilic polymer layer comprises a branched hydrophilic polymer, e.g., PEG, having at least 4 branches. In some embodiments, at least one hydrophilic polymer layer comprises a branched hydrophilic polymer, e.g., PEG, having at least 8 branches. In some embodiments, at least one hydrophilic polymer layer comprises a branched hydrophilic polymer, e.g., PEG, having at least 16 branches. In some embodiments, at least one hydrophilic polymer layer comprises a branched hydrophilic polymer, e.g., PEG, having at least 32 branches. In some embodiments, the plurality of oligonucleotide molecules are present at a surface density of at least 50,000 molecules/$\mu m^2$. In some embodiments, the plurality of oligonucleotide molecules are present at a surface density of at least 100,000 molecules/$\mu m^2$. In some embodiments, the plurality of oligonucleotide molecules are present at a surface density of at least 500,000 molecules/$\mu m^2$. In some embodiments, the sample nucleic acid molecules were administered at a concentration of no greater than 500 nM prior to annealing and clonal amplification. In some embodiments, the sample nucleic acid molecules were administered at a concentration of no greater than 20 pM prior to annealing and clonal amplification. In some embodiments, the sample nucleic acid molecules comprise single-stranded multimeric nucleic acid molecules comprising repeats of a regularly occurring monomer unit. In some embodiments, the single-stranded multimeric nucleic acid molecules are at least 10 kb in length. In some embodiments, the surface further comprises double-stranded monomeric copies of the regularly occurring monomer unit. In some embodiments, said surface is positioned on the interior of a flow channel. In some embodiments, the plurality of oligonucleotide molecules are present at a uniform surface density across the surface. In some embodiments, the plurality of oligonucleotide molecules are present at a local surface density of at least 100,000 molecules/$\mu m^2$ at a first position on the surface, and at a second local surface density at a second position on the surface. In some embodiments, a background fluorescence intensity measured at a region of the surface that is laterally-displaced from the at least one discrete region is no more than 2× of the intensity measured at the at least one discrete region prior to said clonal amplification. In some embodiments, the surface comprises a first layer comprising a monolayer of polymer molecules tethered to a surface of the substrate; a second layer comprising polymer molecules tethered to the polymer molecules of the first layer; and a third layer comprising polymer molecules tethered to the polymer molecules of the second layer, wherein at least one layer comprises branched polymer molecules. In some embodiments, the third layer further comprises oligonucleotides tethered to the polymer molecules of the third layer. In some embodiments, the oligonucleotides tethered to the polymer molecules of the third layer are distributed at a plurality of depths throughout the third layer. In some embodiments, the surface further comprises a fourth layer comprising branched polymer molecules tethered to the polymer molecules of the third layer, and a fifth layer comprising polymer molecules tethered to the branched polymer molecules of the fourth layer. In some embodiments, the polymer molecules of the fifth layer further comprise oligonucleotides tethered to the polymer molecules of the fifth layer. In some embodiments, the oligonucleotides tethered to the polymer molecules of the fifth layer are distributed at a plurality of depths throughout the fifth layer. In some embodiments, the at least one hydrophilic polymer coating layer, comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo(ethylene glycol) methyl ether methacrylate) (POEGMA), polyglutamic acid (PGA), poly-lysine, poly-glucoside, streptavidin, and dextran. In some embodiments, the image of the surface exhibits a ratio of fluorescence intensities for specifically-amplified, Cy3-labeled sample nucleic acid molecules, or complementary sequences thereof, and nonspecific Cy3 dye adsorption background ($B_{inter}$) of at least 3:1. In some embodiments, the image of the surface exhibits a ratio of fluorescence intensities for specifically-amplified, Cy3-labeled sample nucleic acid molecules, or complementary sequences thereof, and a combination of nonspecific Cy3 dye adsorption background and nonspecific amplification background ($B_{inter}+B_{intra}$) of at least 3:1. In some embodiments, the image of the surface exhibits a ratio of fluorescence intensities for specifically-amplified, Cy3-labeled sample nucleic acid molecules, or complementary sequences thereof, and nonspecific dye adsorption background ($B_{inter}$) of at least 5:1. In some embodiments, the image of the surface exhibits a ratio of fluorescence intensities for specifically-amplified, Cy3-labeled sample nucleic acid molecules, or complementary sequences thereof, and a combination of nonspecific Cy3 dye adsorption background and nonspecific amplification background ($B_{inter}+B_{intra}$) of at least 5:1.

Also disclosed herein are surfaces comprising: a) a substrate; b) at least one layers of hydrophilic polymer coating; and c) a plurality of oligonucleotide molecules attached to at least one of the hydrophilic polymer coating layers, wherein the surface exhibits a level of non-specific Cy3 dye adsorption of less than about 0.25 molecules/$\mu m^2$.

In some embodiments, the surface exhibits a level of non-specific Cy3 dye adsorption of less than about 0.1 molecules/$\mu m^2$. In some embodiments, the surface exhibits a ratio of specific Cy3 oligonucleotide labeling to non-specific Cy3 dye adsorption is greater than about 4:1. In some embodiments, the surface exhibits a ratio of specific Cy3 oligonucleotide labeling to non-specific Cy3 dye adsorption is greater than about 10:1. In some embodiments, the plurality of oligonucleotide molecules are attached at a surface density of at least 10,000 molecules/$\mu m^2$. In some embodiments, the plurality of oligonucleotide molecules are attached at a surface density of at least 100,000 molecules/$\mu m^2$. In some embodiments, the surface further comprises a plurality of clonally-amplified clusters of template molecules that have been annealed to the plurality of oligonucleotide molecules, and wherein a fluorescence image of the surface exhibits a contrast-to-noise ratio (CNR) of at least 20. In some embodiments, the contrast-to-noise ratio (CNR) is at least 50. In some embodiments, the contrast-to-noise ratio (CNR) is at least 100. In some embodiments, at least one of the at least two hydrophilic polymer layers comprises a branched polyethylene glycol (PEG) molecule. In some embodiments, the surface comprises a surface of a capillary lumen or at least one internal surface of a flow cell. In some embodiments, the capillary lumen or flow cell is configured for use in performing a nucleic acid hybridization, amplification, or sequencing reaction, or any combination thereof. In some embodiments, the surface further comprises a branched polymer blocking layer. In some embodiments, the branched polymer blocking layer is a branched PEG blocking layer. In some embodiments, the branched polymer blocking layer is covalently tethered to the topmost hydrophilic polymer layer. In some embodiments, the polymers of the first layer comprise primary amine functional groups and the polymers of the second layer comprise N-hydroxysuccinimide (NHS) ester functional groups and, following the deposition of the second layer, the second layer is tethered to the first layer using a covalent amide linkage. In some embodiments, the polymers of the first layer comprise N-hydroxysuccinimide (NHS) ester functional groups and the polymers of the second layer comprise primary amine functional groups and, following the deposition of the second layer, the second layer is tethered to the first layer using a covalent amide linkage. In some embodiments, the oligonucleotides are tethered to the polymer molecules of the second or a third layer at an oligonucleotide-to-polymer molar ratio of about 1:5. In some embodiments, the oligonucleotides are tethered to the polymer molecules of the second or a third layer at an oligonucleotide-to-polymer molar ratio of about 2:5. In some embodiments, the oligonucleotides are tethered to the polymer molecules of the second or a third layer at an oligonucleotide-to-polymer molar ratio of about 3:5. In some embodiments, the oligonucleotides are tethered to the polymer molecules of the second or a third layer at an oligonucleotide-to-polymer molar ratio of about 4:5. In some embodiments, the oligonucleotides are tethered to the polymer molecules of the second or a third layer at an oligonucleotide-to-polymer molar ratio of about 1:1. In some embodiments, the oligonucleotides are tethered to the polymer molecules of the second or a third layer at an oligonucleotide-to-polymer molar ratio of about 4:1. In some embodiments, the oligonucleotides are tethered to the polymer molecules of the second or a third layer at an oligonucleotide-to-polymer molar ratio of about 8:1. In some embodiments, the oligonucleotides are tethered to the polymer molecules of the second or a third layer at an oligonucleotide-to-polymer molar ratio of about 16:1. In some embodiments, the oligonucleotides are tethered to the polymer molecules of the second or a third layer at an oligonucleotide-to-polymer molar ratio of about 32:1. In some embodiments, the oligonucleotides are present at a surface density of at least 10,000 molecules per square micrometer. In some embodiments, the oligonucleotides are present at a surface density of at least 100,000 molecules per square micrometer. In some embodiments, the oligonucleotides are uniformly distributed within the third layer.

Disclosed herein are methods of depositing oligonucleotides on a substrate surface, the method comprising: a) conjugating a first hydrophilic polymer to the substrate surface in a first layer; b) conjugating a second hydrophilic polymer to the first layer to form a second layer, wherein the hydrophilic polymer molecules of the second layer are joined to the first layer by at least two covalent linkages per molecule; and c) conjugating an outermost hydrophilic polymer to the second layer, wherein the outermost hydrophilic polymer molecules comprise oligonucleotide molecules covalently attached thereto prior to conjugating to the second layer.

In some embodiments, the hydrophilic polymer molecules of the second layer are joined to the first layer by at least four covalent linkages per molecule. In some embodiments, the hydrophilic polymer molecules of the second layer are joined to the first layer by at least eight covalent linkages per molecule. In some embodiments, the method further comprises conjugating the outermost hydrophilic polymer directly to the second layer. In some embodiments, the method further comprises conjugating a third hydrophilic polymer to the second layer to form a third layer, and conjugating the outermost hydrophilic polymer to the second layer via the third layer. In some embodiments, the method further comprises conjugating a third hydrophilic polymer to the second layer to form a third layer, conjugating a fourth hydrophilic polymer to the third layer to form a fourth layer, and conjugating the outermost hydrophilic polymer to the second layer via the fourth and third layers. In some embodiments, the first hydrophilic polymer comprises PEG. In some embodiments, the first hydrophilic polymer comprises PGA. In some embodiments, at least one of the hydrophilic polymer layers comprises a branched polymer. In some embodiments, the branched polymer comprises at least 4 branches. In some embodiments, the branched polymer comprises at least 8 branches. In some embodiments, the branched polymer comprises 16 to 32 branches. In some embodiments, the hydrophilic polymer molecules of the fourth layer are joined to the third layer by at least two covalent linkages per molecule. In some embodiments, the hydrophilic polymer molecules of the fourth layer are joined to the third layer by at least four covalent linkages per molecule. In some embodiments, the hydrophilic polymer molecules of the fourth layer are joined to the third layer by at least eight covalent linkages per molecule. In some embodiments, the hydrophilic polymer is delivered to the substrate surface in a solvent comprising ethanol. In some embodiments, the hydrophilic polymer is delivered to the substrate surface in a solvent comprising methanol. In some embodiments, the hydrophilic polymer is delivered to the substrate surface in a solvent comprising dimethyl sulfoxide (DMSO). In some embodiments, the hydrophilic polymer is delivered to the substrate surface in a solvent comprising acetonitrile. In some embodiments, the hydrophilic polymer is delivered to the substrate surface in a solvent comprising buffered phosphate. In some embodiments, the hydrophilic polymer is delivered to the substrate surface in a solvent comprising buffered 3-(N-morpholino) propanesulfonic acid (MOPS). In some embodiments, the hydrophilic polymer is delivered to the substrate surface in a solvent comprising 75% acetonitrile, 25% phosphate buffer. In some embodiments, the hydrophilic polymer is delivered to the substrate surface in a solvent comprising 90% methanol, 10% MOPS buffer.

Disclosed herein are surfaces comprising oligonucleotides at a density of at least 10,000 molecules per square micrometer, wherein the oligonucleotides are tethered to the surface via a multilayered hydrophilic polymeric stratum, and wherein the oligonucleotides are evenly distributed throughout an outermost layer of the multilayered hydrophilic polymeric stratum.

In some embodiments, the oligonucleotides are distributed at a surface density of at least 50,000 molecules per square micrometer. In some embodiments, the oligonucleotides are distributed at a surface density of at least 100,000 molecules per square micrometer. In some embodiments, the oligonucleotides are distributed at a surface density of at least 500,000 molecules per square micrometer. In some embodiments, at least 10% of the tethered oligonucleotides are annealed to target (or sample) oligonucleotides. In some embodiments, the multilayered hydrophilic polymeric stratum is saturated by a hydrophilic solvent. In some embodiments, the surface comprises a surface of a glass, fused-silica, silicon, or polymer (e.g., plastic) substrate. In some embodiments, the multilayered hydrophilic polymeric stratum comprises three or more polymer layers. In some embodiments, the multilayered hydrophilic polymeric stratum comprises five or more polymer layers. In some embodiments, one or more layers of the hydrophilic polymeric stratum comprise branched PEG, branched PVA, branched poly(vinyl pyridine), branched PVP, branched PAA, branched PNIPAM, branched PMA, branched PHEMA, branched PEGMA, branched PGA, branched poly-lysine, branched poly-glucoside, or dextran. In some embodiments, one or more layers of the hydrophilic polymeric stratum comprise branched PEG molecules. In some embodiments, the branched PEG molecules comprises at least 4 branches. In some embodiments, the branched PEG molecules comprise at least 8 branches. In some embodiments, the branched PEG molecules comprise 16 to 32 branches. In some embodiments, at least a first layer and a second layer of the hydrophilic polymeric stratum are tethered to each other using a covalent amide linkage. In some embodiments, at least a first layer and a second layer of the hydrophilic polymeric stratum are tethered to each other by at least two covalent linkages per polymer molecule. In some embodiments, at least a first layer and a second layer of the hydrophilic polymeric stratum are tethered to each other by at least four covalent linkages per polymer molecule. In some embodiments, at least a first layer and a second layer of the hydrophilic polymeric stratum are tethered to each other by at least eight covalent linkages per polymer molecule. In some embodiments, the surface density of tethered oligonucleotides is at least 50,000 molecules per square micrometer. In some embodiments, the surface density of tethered oligonucleotides is at least 100,000 molecules per square micrometer. In some embodiments, the surface exhibits nonspecific binding of CY3 dye of less than 0.25 molecules/$\mu m^2$. In some embodiments, the surface further comprises clusters of clonally-amplified copies of the annealed target oligonucleotides, wherein substantially all of the clonally-amplified copies of the annealed target oligonucleotides comprise a Cy3-labeled nucleotide annealed at a first position, and wherein a fluorescence image of the surface exhibits a contrast-to-noise (CNR) ratio of at least 20. In some embodiments, the contrast-to-noise ratio (CNR) is at least 50. In some embodiments, the contrast-to-noise ratio (CNR) is at least 100. In some embodiments, the contrast-to-noise ratio (CNR) is at least 150. In some embodiments, the contrast-to-noise ratio (CNR) is at least 200. In some embodiments, the clonally-amplified copies of the annealed target oligonucleotides are prepared using a bridge amplification protocol. In some embodiments, the clonally-amplified copies of the annealed target oligonucleotides are prepared using an isothermal bridge amplification protocol. In some embodiments, the clonally-amplified copies of the annealed target oligonucleotides are prepared using a rolling circle amplification (RCA) protocol. In some embodiments, the clonally-amplified copies of the annealed target oligonucleotides are prepared using a helicase-dependent amplification protocol. In some embodiments, the clonally-amplified copies of the annealed target oligonucleotides are prepared using a recombinase-dependent amplification protocol. In some embodiments, the clonally-amplified copies of the annealed target oligonucleotides are prepared using a single-stranded binding (SSB) protein-dependent amplification protocol. In some embodiments, the surface comprises a surface of a capillary lumen or at least one internal surface of a flow cell. In some embodiments, the capillary lumen or flow cell is configured for use in performing a nucleic acid hybridization, amplification, or sequencing reaction, or any combination thereof.

Disclosed herein are methods for performing solid-phase nucleic acid hybridization, the method comprising: a) providing any one of the surfaces disclosed herein; and b) performing a solid-phase nucleic acid hybridization reaction, wherein template nucleic acid molecules are annealed to the tethered oligonucleotides. Also disclosed herein are methods for performing solid-phase nucleic acid amplification, the method comprising: a) providing any one of the surfaces disclosed herein; and b) performing a solid-phase nucleic acid amplification reaction using template nucleic acid molecules hybridized to the tethered oligonucleotides.

In some embodiments, the solid phase nucleic acid amplification comprises thermocycling. In some embodiments, the solid phase nucleic acid amplification comprises isothermal amplification. In some embodiments, the solid phase nucleic acid amplification comprises rolling circle amplification. In some embodiments, the solid phase nucleic acid amplification comprises bridge amplification. In some embodiments, the solid phase nucleic acid amplification comprises isothermal bridge amplification. In some embodiments, the solid phase nucleic acid amplification comprises multiple displacement amplification. In some embodiments, the solid phase nucleic acid amplification comprises helicase treatment. In some embodiments, the solid phase nucleic acid amplification comprises recombinase treatment. In some embodiments, there is no change in a surface density of tethered oligonucleotides over at least 30 cycles of the solid-phase nucleic acid amplification reaction. In some embodiments, there is no change in a surface density of tethered oligonucleotides over at least 40 cycles of the solid-phase nucleic acid amplification reaction. In some embodiments, there is no change in a surface density of tethered oligonucleotides over at least 50 cycles of the solid-phase nucleic acid amplification reaction.

Disclosed herein are methods of performing nucleic acid sequence determination, the method comprising: a) providing any one of the surfaces disclosed herein; b) performing a solid-phase nucleic acid amplification reaction using template nucleic acid molecules hybridized to the tethered oligonucleotides; and c) performing a cyclic series of single nucleotide binding or incorporation reactions, wherein the nucleotides are labeled with a detectable tag.

In some embodiments, the detectable tag is a fluorophore. In some embodiments, the fluorophore is Cy3, and wherein a fluorescence image of the surface acquired as described elsewhere herein under non-signal saturating conditions after the binding or incorporation of a first Cy3-labeled nucleotide exhibits a contrast-to-noise (CNR) ratio of at least 20. In some embodiments, the contrast-to-noise ratio (CNR) is at least 50. In some embodiments, the contrast-to-noise ratio (CNR) is at least 100. In some embodiments, the contrast-to-noise ratio (CNR) is at least 150. In some embodiments, the contrast-to-noise ratio (CNR) is at least 200. In some embodiments, the solid-phase nucleic acid amplification reaction comprises a bridge amplification reaction. In some embodiments, the solid-phase nucleic acid amplification reaction comprises an isothermal bridge amplification reaction. In some embodiments, the solid-phase nucleic acid amplification reaction comprises a rolling circle amplification (RCA) reaction. In some embodiments, the solid-phase nucleic acid amplification reaction comprises a helicase-dependent amplification reaction. In some embodiments, the solid-phase nucleic acid amplification reaction comprises a recombinase-dependent amplification reaction.

Disclosed herein are devices for performing nucleic acid amplification, the device comprising: a) any one of the surfaces disclosed herein; wherein the surface comprises a surface of a capillary lumen or at least one internal surface of a flow cell.

In some embodiments, the device further comprises at least one fluid inlet into the capillary lumen. In some embodiments, the device further comprises at least one fluid outlet. In some embodiments, the device further comprises at least one pump. In some embodiments, the device further comprises at least one fluid mixing manifold. In some embodiments, the device further comprises at least one temperature control element. In some embodiment, the device further comprises at least one optical window.

Disclosed here are systems for performing nucleic acid sequencing, the system comprising: a) at least one of the devices disclosed herein; b) a fluid control module; and c) an imaging module.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference in its entirety. In the event of a conflict between a term herein and a term in an incorporated reference, the term herein controls.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6A: example of simulated data for which the SNR=2 and CNR=1.25. FIG. 6B: example of simulated data for which SNR=2 and CNR=12.29.

FIG. 19A provides examples of image data for two different hybridization buffer formulations and protocols. FIG. 19B provides an example of the corresponding image data obtained using a standard hybridization buffer and protocol.

FIG. 25A: modified glass surface. At inset, one sees that the surface yields a CNR of 226. FIG. 25B: modified plastic surface. At inset, one sees that the surface yields a CNR of 109.

DETAILED DESCRIPTION

Figure 1:
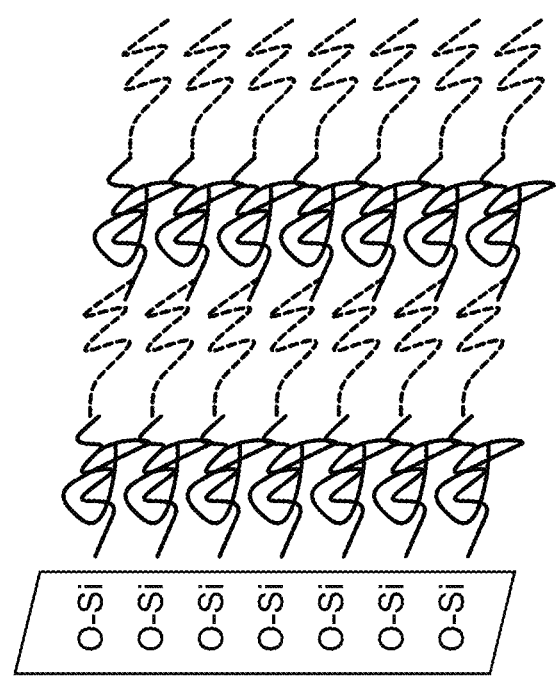
FIG. 1 provides a schematic illustration of one embodiment of the low binding solid supports of the present disclosure in which the support comprises a glass substrate and alternating layers of hydrophilic coatings which are covalently or non-covalently adhered to the glass, and which further comprises chemically-reactive functional groups that serve as attachment sites for oligonucleotide primers.

Disclosed herein are novel solid supports for use in solid-phase nucleic acid amplification and sequencing, or other bioassay applications. The solid supports disclosed herein exhibit low non-specific binding of proteins and other amplification reaction components, and improved stability to repetitive exposure to different solvents, changes in temperature, chemical affronts such as low pH, or long term storage.

Alone or in combination with improved nucleic acid hybridization and amplification protocols, some supports disclosed herein lead to one or more of: (i) reduced requirements for the amount of starting material necessary, (ii) lowered temperature requirements for isothermal or thermal ramping amplification protocols, (iii) increased amplification rates, (iv) increased amplification specificity (that is, more selective amplification of the single-stranded template molecules of the amplified colonies while decreasing non-specific amplification of surface primers and primer-dimers), and (v) allow greater discrimination of sequence-specific signal from background signals (such as signals arising from both interstitial and intrastitial background), thereby providing improved contrast-to-noise ratio (CNR) and base-calling accuracy compared to conventional nucleic acid amplification and sequencing methodologies.

The starting point for achieving the aforementioned improvements, or any combination thereof, are the disclosed low non-specific binding supports comprising one or more polymer coatings, e.g., PEG polymer films, that minimize non-specific binding of protein and labeled nucleotides to the solid support. The subsequent demonstration of improved nucleic acid hybridization and amplification rates and specificity may be achieved through one or more of the following additional aspects of the present disclosure: (i) primer design (sequence and/or modifications), (ii) control of tethered primer density on the solid support, (iii) the surface composition of the solid support, (iv) the surface polymer density of the solid support, (v) the use of improved hybridization conditions before and during amplification, and/or (vi) the use of improved amplification formulations that decrease non-specific primer amplification or increase template amplification efficiency.

The advantages of the disclosed low non-specific binding supports and associated hybridization and amplification methods confer one or more of the following additional advantages for any sequencing system: (i) decreased fluidic wash times (due to reduced non-specific binding, and thus faster sequencing cycle times), (ii) decreased imaging times (and thus faster turnaround times for assay readout and sequencing cycles), (iii) decreased overall work flow time requirements (due to decreased cycle times), (iv) decreased detection instrumentation costs (due to the improvements in CNR), (v) improved readout (base-calling) accuracy (due to improvements in CNR), (vi) improved reagent stability and decreased reagent usage requirements (and thus reduced reagents costs), and (vii) fewer run-time failures due to nucleic acid amplification failures.

The low binding hydrophilic surfaces (multilayer and/or monolayer) for surface bioassays, e.g., genotyping and sequencing assays, are created by using any combination of the following.

Polar protic, polar aprotic and/or nonpolar solvents for depositing and/or coupling linear or multi-branched hydrophilic polymer subunits on a substrate surface. Some multi-branched hydrophilic polymer subunits may contain functional end groups to promote covalent coupling or non-covalent binding interactions with other polymer subunits. Examples of suitable functional end groups include biotin, methoxy ether, carboxylate, amine, ester compounds, azide, alkyne, maleimide, thiol, and silane groups.

Any combination of linear, branched, or multi-branched polymer subunits coupled through subsequent layered addition via modified coupling chemistry/solvent/buffering systems that may include individual subunits with orthogonal end coupling chemistries or any of the respective combinations, such that resultant surface is hydrophilic and exhibits low nonspecific binding of proteins and other molecular assay components. In some instances, the hydrophilic, functionalized substrate surfaces of the present disclosure exhibit contact angle measurements that do not exceed 35 degrees.

Compatible buffering systems in addition to the aforementioned solvents, with a desirable pH range of 5-10. Examples include, but are not limited to, phosphate buffered saline, phosphate buffer, TAPS, MES, MOPS, or any combination of these.

Subsequent biomolecule attachment (e.g., of proteins, peptides, nucleic acids, oligonucleotides, or cells) on the low binding/hydrophilic substrates via any of a variety of individual conjugation chemistries to be described below, or any combination thereof. Layer deposition and/or conjugation reactions may be performed using solvent mixtures which may contain any ratio of the following components: ethanol, methanol, acetonitrile, acetone, DMSO, DMF, H$_2$O, and the like. In addition, compatible buffering systems in the desirable pH range of 5-10 may be used for controlling the rate and efficiency of deposition and coupling, whereby coupling rates is excess of >5x of those for conventional aqueous buffer-based methods may be achieved.

Definitions

Unless otherwise defined, all technical terms used herein have the same meaning as commonly understood by one of ordinary skill in the art in the field to which this disclosure belongs.

As used in this specification and the appended claims, the singular forms "a", "an", and "the" include plural references unless the context clearly dictates otherwise. Any reference to "or" herein is intended to encompass "and/or" unless otherwise stated.

As used herein, the term 'about' a number refers to that number plus or minus 10% of that number. The term 'about' when used in the context of a range refers to that range minus 10% of its lowest value and plus 10% of its greatest value.

As used herein, the phrase 'at least one of' in the context of a series encompasses lists including a single member of the series, two members of the series, up to and including all members of the series, alone or in some cases in combination with unlisted components.

As used herein, fluorescence is 'specific' if it arises from fluorophores that are annealed or otherwise tethered to the surface, such as through a nucleic acid having a region of reverse complementarity to a corresponding segment of an oligo on the surface and annealed to said corresponding segment. This fluorescence is contrasted with fluorescence arising from fluorophores not tethered to the surface through such an annealing process, or in some cases to background florescence of the surface.

Nucleic Acids:

As used herein, a "nucleic acid" (also referred to as a "polynucleotide", "oligonucleotide", ribonucleic acid (RNA), or deoxyribonucleic acid (DNA)) is a linear polymer of two or more nucleotides joined by covalent internucleosidic linkages, or variants or functional fragments thereof. In naturally occurring examples of nucleic acids, the internucleoside linkage is typically a phosphodiester bond. However, other examples optionally comprise other internucleoside linkages, such as phosphorothiolate linkages and may or may not comprise a phosphate group. Nucleic acids include double- and single-stranded DNA, as well as double- and single-stranded RNA, DNA/RNA hybrids, peptide-nucleic acids (PNAs), hybrids between PNAs and DNA or RNA, and may also include other types of nucleic acid modifications.

As used herein, a "nucleotide" refers to a nucleotide, nucleoside, or analog thereof. In some cases, the nucleotide is an N- or C-glycoside of a purine or pyrimidine base (e.g., a deoxyribonucleoside containing 2-deoxy-D-ribose or ribonucleoside containing D-ribose). Examples of other nucleotide analogs include, but are not limited to, phosphorothioates, phosphoramidates, methyl phosphonates, chiral-methyl phosphonates, 2-O-methyl ribonucleotides, and the like.

Nucleic acids may optionally be attached to one or more non-nucleotide moieties such as labels and other small molecules, large molecules (such as proteins, lipids, sugars, etc.), and solid or semi-solid supports, for example through covalent or non-covalent linkages with either the 5' or 3' end of the nucleic acid. Labels include any moiety that is detectable using any of a variety of detection methods known to those of skill in the art, and thus renders the attached oligonucleotide or nucleic acid similarly detectable. Some labels emit electromagnetic radiation that is optically detectable or visible. Alternately or in combination, some labels comprise a mass tag that renders the labeled oligonucleotide or nucleic acid visible in mass spectral data, or a redox tag that renders the labeled oligonucleotide or nucleic acid detectable by amperometry or voltammetry. Some labels comprise a magnetic tag that facilitates separation and/or purification of the labeled oligonucleotide or nucleic acid. The nucleotide or polynucleotide is often not attached to a label, and the presence of the oligonucleotide or nucleic acid is directly detected.

The disclosed low non-specific binding supports and associated nucleic acid hybridization and amplification methods may be used for the analysis of nucleic acid molecules derived from any of a variety of different cell, tissue, or sample types known to those of skill in the art. For example, nucleic acids may be extracted from cells, or tissue samples comprising one or more types of cells, derived from eukaryotes (such as animals, plants, fungi, protista), archaebacteria, or eubacteria. In some cases, nucleic acids may be extracted from prokaryotic or eukaryotic cells, such as adherent or non-adherent eukaryotic cells. Nucleic acids are variously extracted from, for example, primary or immortalized rodent, porcine, feline, canine, bovine, equine, primate, or human cell lines. Nucleic acids may be extracted from any of a variety of different cell, organ, or tissue types (e.g., white blood cells, red blood cells, platelets, epithelial cells, endothelial cells, neurons, glial cells, astrocytes, fibroblasts, skeletal muscle cells, smooth muscle cells, gametes, or cells from the heart, lungs, brain, liver, kidney, spleen, pancreas, thymus, bladder, stomach, colon, or small intestine). Nucleic acids may be extracted from normal or healthy cells. Alternately or in combination, acids are extracted from diseased cells, such as cancerous cells, or from pathogenic cells that are infecting a host. Some nucleic acids may be extracted from a distinct subset of cell types, e.g., immune cells (such as T cells, cytotoxic (killer) T cells, helper T cells, alpha beta T cells, gamma delta T cells, T cell progenitors, B cells, B-cell progenitors, lymphoid stem cells, myeloid progenitor cells, lymphocytes, granulocytes, Natural Killer cells, plasma cells, memory cells, neutrophils, eosinophils, basophils, mast cells, monocytes, dendritic cells, and/or macrophages, or any combination thereof), undifferentiated human stem cells, human stem cells that have been induced to differentiate, rare cells (e.g., circulating tumor cells (CTCs), circulating epithelial cells, circulating endothelial cells, circulating endometrial cells, bone marrow cells, progenitor cells, foam cells, mesenchymal cells, or trophoblasts). Other cells are contemplated and consistent with the disclosure herein.

Nucleic acid extraction from cells or other biological samples may be performed using any of a number of techniques known to those of skill in the art. For example, a typical DNA extraction procedure comprises (i) collection of the cell sample or tissue sample from which DNA is to be extracted, (ii) disruption of cell membranes (i.e., cell lysis) to release DNA and other cytoplasmic components, (iii) treatment of the lysed sample with a concentrated salt solution to precipitate proteins, lipids, and RNA, followed by centrifugation to separate out the precipitated proteins, lipids, and RNA, and (iv) purification of DNA from the supernatant to remove detergents, proteins, salts, or other reagents used during the cell membrane lysis step.

A variety of suitable commercial nucleic acid extraction and purification kits are consistent with the disclosure herein. Examples include, but are not limited to, the QIAamp® kits (for isolation of genomic DNA from human samples) and DNAeasy kits (for isolation of genomic DNA from animal or plant samples) from Qiagen (Germantown, Md.), or the Maxwell® and ReliaPrep™ series of kits from Promega™ (Madison, Wis.).

Low Non-Specific Binding Supports for Solid-Phase Nucleic Acid Hybridization and Amplification:

Disclosed herein are solid supports comprising low non-specific binding surface compositions that enable improved nucleic acid hybridization and amplification performance. In general, the disclosed supports may comprise a substrate (or support structure), one or more layers of a covalently or non-covalently attached low-binding, chemical modification layers, e.g., silane layers, polymer films, and one or more covalently or non-covalently attached primer sequences that may be used for tethering single-stranded template oligonucleotides to the support surface (FIG. 1). In some instances, the formulation of the surface, e.g., the chemical composition of one or more layers, the coupling chemistry used to cross-link the one or more layers to the support surface and/or to each other, and the total number of layers, may be varied such that non-specific binding of proteins, nucleic acid molecules, and other hybridization and amplification reaction components to the support surface is minimized or reduced relative to a comparable monolayer. Often, the formulation of the surface may be varied such that non-specific hybridization on the support surface is minimized or reduced relative to a comparable monolayer. The formulation of the surface may be varied such that non-specific amplification on the support surface is minimized or reduced relative to a comparable monolayer. The formulation of the surface may be varied such that specific amplification rates and/or yields on the support surface are maximized. Amplification levels suitable for detection are achieved in no more than 2, 3, 4, 5, 6, 7, 8, 9, 10, 15, 20, 25, 30, or more than 30 amplification cycles in some cases disclosed herein.

Examples of materials from which the substrate or support structure may be fabricated include, but are not limited to, glass, fused-silica, silicon, a polymer (e.g., polystyrene (PS), macroporous polystyrene (MPPS), polymethylmethacrylate (PMMA), polycarbonate (PC), polypropylene (PP), polyethylene (PE), high density polyethylene (HDPE), cyclic olefin polymers (COP), cyclic olefin copolymers (COC), polyethylene terephthalate (PET)), or any combination thereof. Various compositions of both glass and plastic substrates are contemplated.

The substrate or support structure may be rendered in any of a variety of geometries and dimensions known to those of skill in the art, and may comprise any of a variety of materials known to those of skill in the art. For example, in some instances the substrate or support structure may be locally planar (e.g., comprising a microscope slide or the surface of a microscope slide). Globally, the substrate or support structure may be cylindrical (e.g., comprising a capillary or the interior surface of a capillary), spherical (e.g., comprising the outer surface of a non-porous bead), or irregular (e.g., comprising the outer surface of an irregularly-shaped, non-porous bead or particle). In some instances, the surface of the substrate or support structure used for nucleic acid hybridization and amplification may be a solid, non-porous surface. In some instances, the surface of the substrate or support structure used for nucleic acid hybridization and amplification may be porous, such that the coatings described herein penetrate the porous surface, and nucleic acid hybridization and amplification reactions performed thereon may occur within the pores.

The substrate or support structure that comprises the one or more chemically-modified layers, e.g., layers of a low non-specific binding polymer, may be independent or integrated into another structure or assembly. For example, in some instances, the substrate or support structure may comprise one or more surfaces within an integrated or assembled microfluidic flow cell. The substrate or support structure may comprise one or more surfaces within a microplate format, e.g., the bottom surface of the wells in a microplate. As noted above, in some preferred embodiments, the substrate or support structure comprises the interior surface (such as the lumen surface) of a capillary. In alternate preferred embodiments the substrate or support structure comprises the interior surface (such as the lumen surface) of a capillary etched into a planar chip.

The chemical modification layers may be applied uniformly across the surface of the substrate or support structure. Alternately, the surface of the substrate or support structure may be non-uniformly distributed or patterned, such that the chemical modification layers are confined to one or more discrete regions of the substrate. For example, the substrate surface may be patterned using photolithographic techniques to create an ordered array or random pattern of chemically-modified regions on the surface. Alternately or in combination, the substrate surface may be patterned using, e.g., contact printing and/or ink-jet printing techniques. In some instances, an ordered array or random pattern of chemically-modified discrete regions may comprise at least 1, 5, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000 or more discrete regions, or any intermediate number spanned by the range herein.

In order to achieve low nonspecific binding surfaces (also referred to herein as "low binding" or "passivated" surfaces), hydrophilic polymers may be nonspecifically adsorbed or covalently grafted to the substrate or support surface. Typically, passivation is performed utilizing poly (ethylene glycol) (PEG, also known as polyethylene oxide (PEO) or polyoxyethylene), poly(vinyl alcohol) (PVA), poly (vinyl pyridine), poly(vinyl pyrrolidone) (PVP), poly (acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, dextran, or other hydrophilic polymers with different molecular weights and end groups that are linked to a surface using, for example, silane chemistry. The end groups distal from the surface can include, but are not limited to, biotin, methoxy ether, carboxylate, amine, NHS ester, maleimide, and bis-silane. In some instances, two or more layers of a hydrophilic polymer, e.g., a linear polymer, branched polymer, or multi-branched polymer, may be deposited on the surface. In some instances, two or more layers may be covalently coupled to each other or internally cross-linked to improve the stability of the resulting surface. In some instances, oligonucleotide primers with different base sequences and base modifications (or other biomolecules, e.g., enzymes or antibodies) may be tethered to the resulting surface layer at various surface densities. In some instances, for example, both surface functional group density and oligonucleotide concentration may be varied to target a certain primer density range. Additionally, primer density can be controlled by diluting oligonucleotide with other molecules that carry the same functional group. For example, amine-labeled oligonucleotide can be diluted with amine-labeled polyethylene glycol in a reaction with an NHS-ester coated surface to reduce the final primer density. Primers with different lengths of linker between the hybridization region and the surface attachment functional group can also be applied to control surface density. Example of suitable linkers include poly-T and poly-A strands at the 5' end of the primer (e.g., 0 to 20 bases), PEG linkers (e.g., 3 to 20 monomer units), and carbon-chain (e.g., C6, C12, C18, etc.). To measure the primer density, fluorescently-labeled primers may be tethered to the surface and a fluorescence reading then compared with that for a dye solution of known concentration.

In some embodiments, the hydrophilic polymer can be a cross linked polymer. In some embodiments, the cross-linked polymer can include one type of polymer cross linked with another type of polymer. Examples of the crossed-linked polymer can include poly(ethylene glycol) cross-linked with another polymer selected from polyethylene oxide (PEO) or polyoxyethylene), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxylethyl methacrylate) (PHEMA), poly(oligo (ethylene glycol) methyl ether methacrylate) (POEGMA), polyglutamic acid (PGA), poly-lysine, poly-glucoside, streptavidin, dextran, or other hydrophilic polymers. In some embodiments, the cross-linked polymer can be a poly(ethylene glycol) cross-linked with polyacrylamide.

As a result of the surface passivation techniques disclosed herein, proteins, nucleic acids, and other biomolecules do not "stick" to the substrates, that is, they exhibit low nonspecific binding (NSB). Examples are shown below using standard monolayer surface preparations with varying glass preparation conditions. Hydrophilic surface that have been passivated to achieve ultra-low NSB for proteins and nucleic acids require novel reaction conditions to improve primer deposition reaction efficiencies, hybridization performance, and induce effective amplification. All of these processes require oligonucleotide attachment and subsequent protein binding and delivery to a low binding surface. As described below, the combination of a new primer surface conjugation formulation (Cy3 oligonucleotide graft titration) and resulting ultra-low non-specific background (NSB functional tests performed using red and green fluorescent dyes) yielded results that demonstrate the viability of the disclosed approaches. Some surfaces disclosed herein exhibit a ratio of specific (e.g., hybridization to a tethered primer or probe) to nonspecific binding (e.g., $B_{inter}$) of a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein. Some surfaces disclosed herein exhibit a ratio of specific to nonspecific fluorescence signal (e.g., for specifically-hybridized to nonspecifically bound labeled oligonucleotides, or for specifically-amplified to nonspecifically-bound ($B_{inter}$) or non-specifically amplified ($B_{intra}$) labeled oligonucleotides or a combination thereof ($B_{inter}+B_{intra}$)) for a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein.

In order to scale primer surface density and add additional dimensionality to hydrophilic or amphoteric surfaces, substrates comprising multi-layer coatings of PEG and other hydrophilic polymers have been developed. By using hydrophilic and amphoteric surface layering approaches that include, but are not limited to, the polymer/co-polymer materials described below, it is possible to increase primer loading density on the surface significantly. Traditional PEG coating approaches use monolayer primer deposition, which have been generally reported for single molecule applications, but do not yield high copy numbers for nucleic acid amplification applications. As described herein "layering" can be accomplished using traditional crosslinking approaches with any compatible polymer or monomer subunits such that a surface comprising two or more highly crosslinked layers can be built sequentially. Examples of suitable polymers include, but are not limited to, streptavidin, poly acrylamide, polyester, dextran, poly-lysine, and copolymers of poly-lysine and PEG. In some instances, the different layers may be attached to each other through any of a variety of conjugation reactions including, but not limited to, biotin-streptavidin binding, azide-alkyne click reaction, amine-NHS ester reaction, thiol-maleimide reaction, and ionic interactions between positively charged polymer and negatively charged polymer. In some instances, high primer density materials may be constructed in solution and subsequently layered onto the surface in multiple steps.

Figure 2:
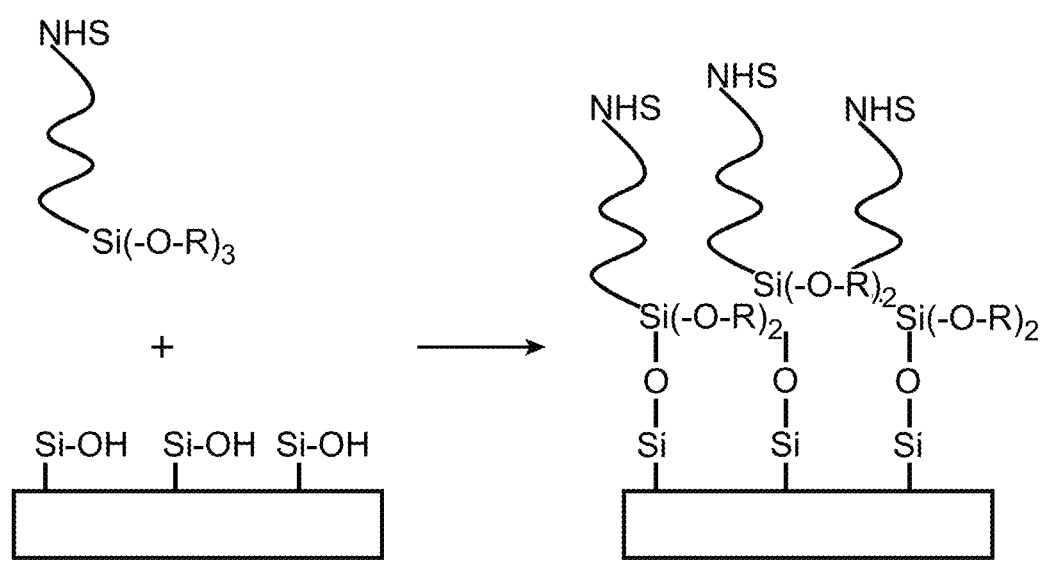
FIG. 2 provides a schematic illustration of the use of a silane reaction to covalently couple a first polymer to a substrate (e.g., glass) surface to create a first polymer layer.

FIG. 2 provides a schematic illustration of one non-limiting example of grafting a first hydrophilic polymer layer to a substrate, e.g., a glass substrate. Following cleaning of the glass surface using any of a variety of methods known to those of skill in the art (e.g., treatment with a Piranha solution, plasma cleaning, etc.), the substrate is treated with a silane solution (e.g., a silane PEG 5K solution), rinsed, dried, and cured at an elevated temperature to form a covalent bond with surface. The end of the polymer distal from the surface may comprise any of a variety of chemically-reactive functional groups or protected functional groups. An amine-reactive NHS group is illustrated in FIG. 2.

Figure 3:
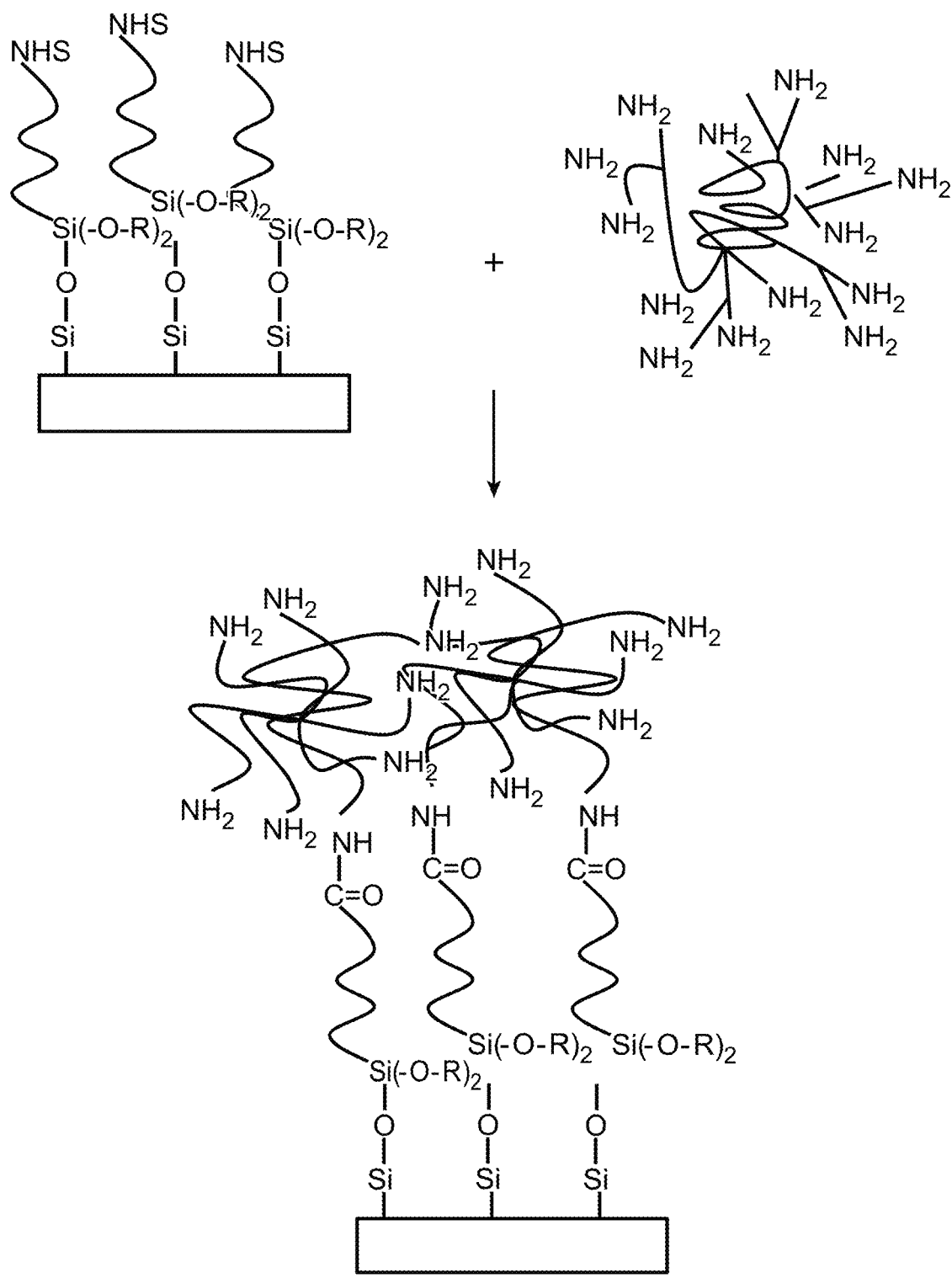
FIG. 3 provides a schematic illustration of the covalent coupling of a branched polymer to a surface such as that illustrated in FIG. 2 to form a second polymer layer on a substrate surface.

FIG. 3 provides a schematic illustration of one non-limiting example of coupling a derivatized substrate comprising a first polymer layer having an NHS-functional group such as that illustrated in FIG. 2 with a primary amine-functionalized branched polymer (e.g., a 16-branch or 32-branch PEG polymer (also referred to as 16-arm or 32-arm PEG, respectively)) to create a second hydrophilic polymer layer comprising an excess of unreacted functional groups.

Figure 4:
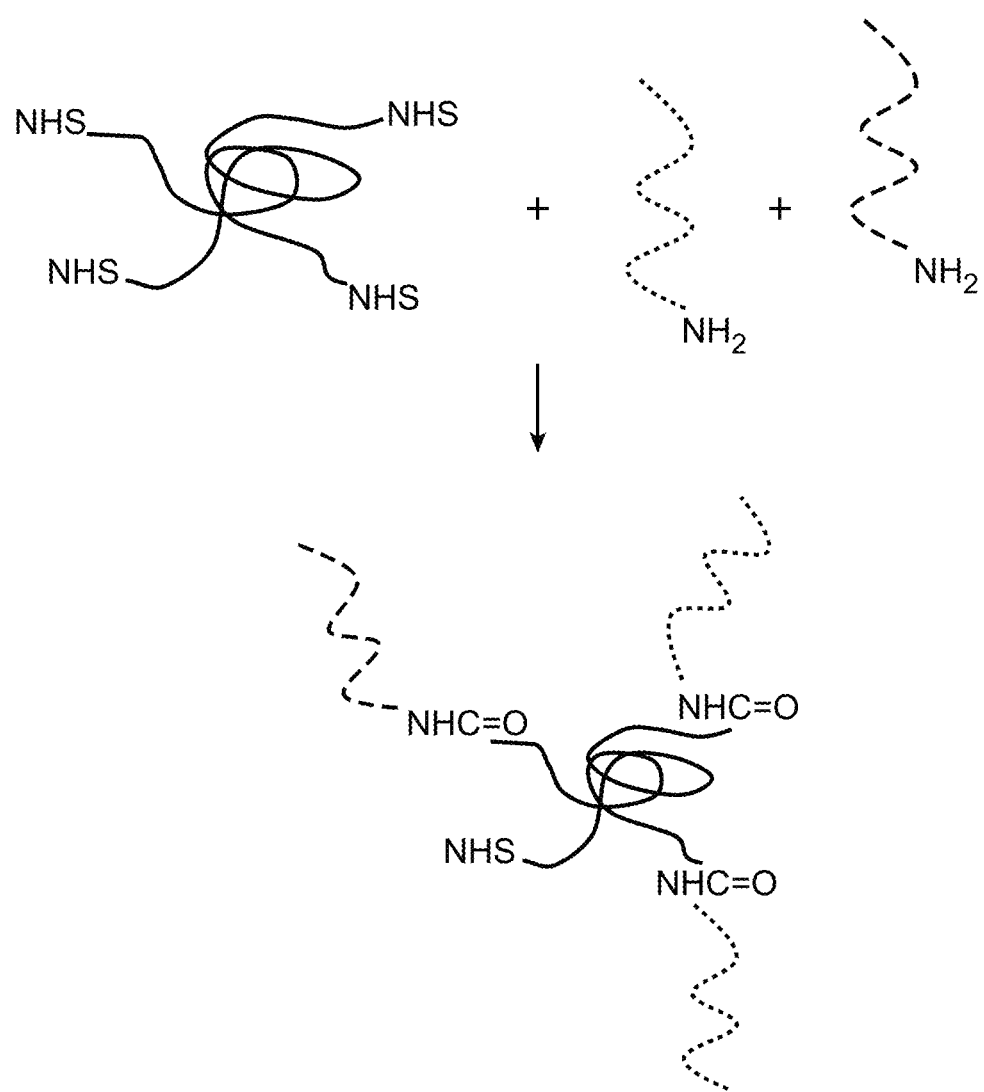
FIG. 4 provides a schematic illustration of a coupling reaction used to covalently attach one or more oligonucleotide adapter or primer sequences (e.g., sequence 1 (dotted line) and sequence 2 (dashed line)) to a branched polymer.

FIG. 4 provides a schematic illustration of one non-limiting example of reacting a branched polymer comprising reactive functional groups (e.g., a 4-branched NHS-PEG) with one or more oligonucleotide adapter or primer sequences in solution (e.g., oligonucleotides comprising a primary amine, as illustrated by the dotted and dashed lines) prior to depositing on a substrate surface to create a hydrophilic layer comprising covalently-attached oligonucleotide molecules. By varying the molar ratio of the oligonucleotide molecule(s) (or other biomolecules to be tethered, e.g., peptides, proteins, enzymes, antibodies, etc.) to that of the branched polymer, one may vary the resulting surface density of attached oligonucleotide sequences in a controlled manner. In some instances, one or more oligonucleotide molecules (or other biomolecules) may be covalently tethered to an existing polymer layer after the layer has been deposited on a surface.

Figure 5:
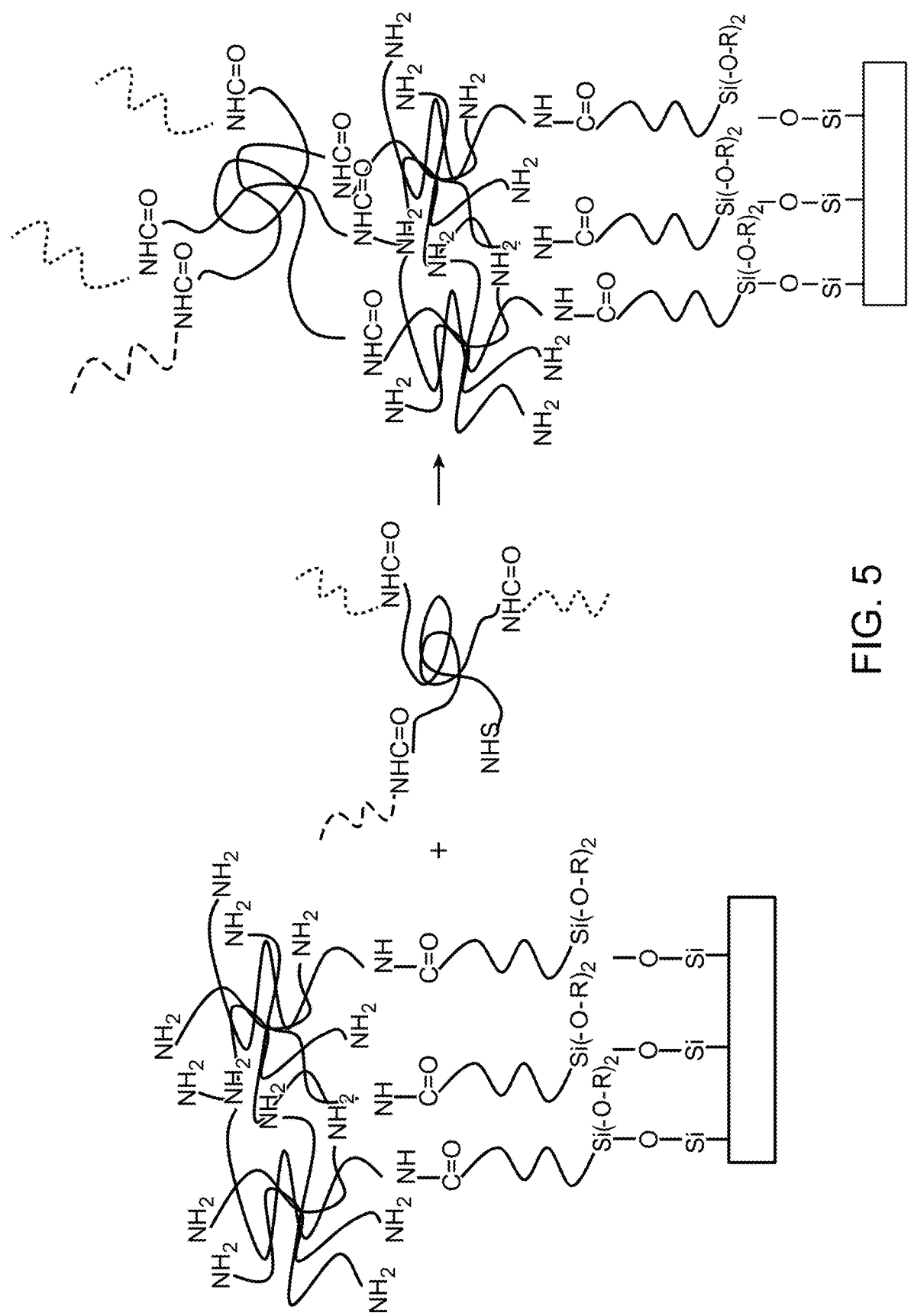
FIG. 5 provides a schematic illustration of the covalent coupling of a branched polymer comprising covalently-attached oligonucleotide adapter or primer sequences to a surface such as that illustrated in FIG. 3 to form a third polymer layer on a substrate surface.

FIG. 5 provides a schematic illustration of one non-limiting example of coupling a branched polymer comprising covalently-attached oligonucleotide primers to a layered hydrophilic surface such as the one illustrated in FIG. 3. In this example, a branched polymer comprising two different oligonucleotide primers (represented by dotted and dashed lines) and amine-reactive NHS groups is coupled to the primary amines of the previous layer to create a multilayered, three-dimensional hydrophilic surface comprising a controlled surface density of tethered oligonucleotide primers.

The attachment chemistry used to graft a first chemically-modified layer to a support surface will generally be dependent on both the material from which the support is fabricated and the chemical nature of the layer. In some instances, the first layer may be covalently attached to the support surface. In some instances, the first layer may be non-covalently attached, e.g., adsorbed to the surface through non-covalent interactions such as electrostatic interactions, hydrogen bonding, or van der Waals interactions between the surface and the molecular components of the first layer. In either case, the substrate surface may be treated prior to attachment or deposition of the first layer. Any of a variety of surface preparation techniques known to those of skill in the art may be used to clean or treat the support surface. For example, glass or silicon surfaces may be acid-washed using a Piranha solution (a mixture of sulfuric acid ($H_2SO_4$) and hydrogen peroxide ($H_2O_2$)) and/or cleaned using an oxygen plasma treatment method.

Silane chemistries constitute one non-limiting approach for covalently modifying the silanol groups on glass or silicon surfaces to attach more reactive functional groups (e.g., amines or carboxyl groups), which may then be used in coupling linker molecules (e.g., linear hydrocarbon molecules of various lengths, such as C6, C12, C18 hydrocarbons, or linear polyethylene glycol (PEG) molecules) or layer molecules (e.g., branched PEG molecules or other polymers) to the surface. Examples of suitable silanes that may be used in creating any of the disclosed low binding support surfaces include, but are not limited to, (3-Aminopropyl) trimethoxysilane (APTMS), (3-Aminopropyl) triethoxysilane (APTES), any of a variety of PEG-silanes (e.g., comprising molecular weights of 1K, 2K, 5K, 10K, 20K, etc.), amino-PEG silane (i.e., comprising a free amino functional group), maleimide-PEG silane, biotin-PEG silane, and the like.

Any of a variety of molecules known to those of skill in the art including, but not limited to, amino acids, peptides, nucleotides, oligonucleotides, other monomers or polymers, or combinations thereof may be used in creating the one or more chemically-modified layers on the support surface, where the choice of components used may be varied to alter one or more properties of the support surface, e.g., the surface density of functional groups and/or tethered oligonucleotide primers, the hydrophilicity/hydrophobicity of the support surface, or the three three-dimensional nature (i.e., "thickness") of the support surface. Examples of preferred polymers that may be used to create one or more layers of low non-specific binding material in any of the disclosed support surfaces include, but are not limited to, polyethylene glycol (PEG) of various molecular weights and branching structures, streptavidin, polyacrylamide, polyester, dextran, poly-lysine, and poly-lysine copolymers, or any combination thereof. Examples of conjugation chemistries that may be used to graft one or more layers of material (e.g. polymer layers) to the support surface and/or to cross-link the layers to each other include, but are not limited to, biotin-streptavidin interactions (or variations thereof), his tag—Ni/NTA conjugation chemistries, methoxy ether conjugation chemistries, carboxylate conjugation chemistries, amine conjugation chemistries, NHS esters, maleimides, thiol, epoxy, azide, hydrazide, alkyne, isocyanate, and silane.

One or more layers of a multi-layered surface may comprise a branched polymer or may be linear. Examples of suitable branched polymers include, but are not limited to, branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly (N-isopropylacrylamide) (branched PNIPAM), branched poly(methyl methacrylate) (branched PMA), branched poly (2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, and dextran.

In some instances, the branched polymers used to create one or more layers of any of the multi-layered surfaces disclosed herein may comprise at least 4 branches, at least 5 branches, at least 6 branches, at least 7 branches, at least 8 branches, at least 9 branches, at least 10 branches, at least 12 branches, at least 14 branches, at least 16 branches, at least 18 branches, at least 20 branches, at least 22 branches, at least 24 branches, at least 26 branches, at least 28 branches, at least 30 branches, at least 32 branches, at least 34 branches, at least 36 branches, at least 38 branches, or at least 40 branches. Molecules often exhibit a 'power of 2' number of branches, such as 2, 4, 8, 16, 32, 64, or 128 branches.

Exemplary PEG multilayers include PEG (8, 16, 8) (8 arm, 16 arm, 8 arm)? on PEG-amine-APTES. Similar concentrations were observed for 3-layer multi-arm PEG (8 arm, 16 arm, 8 arm) and (8 arm, 64 arm, 8 arm) on PEG-amine-APTES exposed to 8 uM primer, and 3-layer multi-arm PEG (8 arm, 8 arm, 8 arm) using star-shape PEG-amine to replace 16 arm and 64 arm PEG multilayers having comparable first, second and third PEG layers are also contemplated.

Linear, branched, or multi-branched polymers used to create one or more layers of any of the multi-layered surfaces disclosed herein may have a molecular weight of at least 500, at least 1,000, at least 1,500, at least 2,000, at least 2,500, at least 3,000, at least 3,500, at least 4,000, at least 4,500, at least 5,000, at least 7,500, at least 10,000, at least 12,500, at least 15,000, at least 17,500, at least 20,000, at least 25,000, at least 30,000, at least 35,000, at least 40,000, at least 45,000, or at least 50,000 Daltons. In some instances, the linear, branched, or multi-branched polymers used to create one or more layers of any of the multi-layered surfaces disclosed herein may have a molecular weight of at most 50,000, at most 45,000, at most 40,000, at most 35,000, at most 30,000, at most 25,000, at most 20,000, at most 17,500, at most 15,000, at most 12,500, at most 10,000, at most 7,500, at most 5,000, at most 4,500, at most 4,000, at most 3,500, at most 3,000, at most 2,500, at most 2,000, at most 1,500, at most 1,000, or at most 500 Daltons. Any of the lower and upper values described in this paragraph may be combined to form a range included within the present disclosure, for example, in some instances the molecular weight of linear, branched, or multi-branched polymers used to create one or more layers of any of the multi-layered surfaces disclosed herein may range from about 1,500 to about 20,000 Daltons. Those of skill in the art will recognize that the molecular weight of linear, branched, or multi-branched polymers used to create one or more layers of any of the multi-layered surfaces disclosed herein may have any value within this range, e.g., about 1,260 Daltons.

In some instances, e.g., wherein at least one layer of a multi-layered surface comprises a branched polymer, the number of covalent bonds between a branched polymer molecule of the layer being deposited and molecules of the previous layer may range from about one covalent linkage per molecule and about 32 covalent linkages per molecule. In some instances, the number of covalent bonds between a branched polymer molecule of the new layer and molecules of the previous layer may be at least 1, at least 2, at least 3, at least 4, at least 5, at least 6, at least 7, at least 8, at least 9, at least 10, at least 12, at least 14, at least 16, at least 18, at least 20, at least 22, at least 24, at least 26, at least 28, at least 30, or at least 32, or more than 32 covalent linkages per molecule. In some instances, the number of covalent bonds between a branched polymer molecule of the new layer and molecules of the previous layer may be at most 32, at most 30, at most 28, at most 26, at most 24, at most 22, at most 20, at most 18, at most 16, at most 14, at most 12, at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of covalent bonds between a branched polymer molecule of the new layer and molecules of the previous layer may range from about 4 to about 16. Those of skill in the art will recognize that the number of covalent bonds between a branched polymer molecule of the new layer and molecules of the previous layer may have any value within this range, e.g., about 11 in some instances, or an average number of about 4.6 in other instances.

Any reactive functional groups that remain following the coupling of a material layer to the support surface may optionally be blocked by coupling a small, inert molecule using a high yield coupling chemistry. For example, in the case that amine coupling chemistry is used to attach a new material layer to the previous one, any residual amine groups may subsequently be acetylated or deactivated by coupling with a small amino acid such as glycine.

The number of layers of low non-specific binding material, e.g., a hydrophilic polymer material, deposited on the surface of the disclosed low binding supports may range from 1 to about 10. In some instances, the number of layers is at least 1, at least 2, at least 3, at least 4, at least 5, at least 6, at least 7, at least 8, at least 9, or at least 10. In some instances, the number of layers may be at most 10, at most 9, at most 8, at most 7, at most 6, at most 5, at most 4, at most 3, at most 2, or at most 1. Any of the lower and upper values described in this paragraph may be combined to form a range included within the present disclosure, for example, in some instances the number of layers may range from about 2 to about 4. In some instances, all of the layers may comprise the same material. In some instances, each layer may comprise a different material. In some instances, the plurality of layers may comprise a plurality of materials. In some instances at least one layer may comprise a branched polymer. In some instance, all of the layers may comprise a branched polymer.

One or more layers of low non-specific binding material may in some cases be deposited on and/or conjugated to the substrate surface using a polar protic solvent, a polar aprotic solvent, a nonpolar solvent, or any combination thereof. In some instances the solvent used for layer deposition and/or coupling may comprise an alcohol (e.g., methanol, ethanol, propanol, etc.), another organic solvent (e.g., acetonitrile, dimethyl sulfoxide (DMSO), dimethyl formamide (DMF), etc.), water, an aqueous buffer solution (e.g., phosphate buffer, phosphate buffered saline, 3-(N-morpholino)propanesulfonic acid (MOPS), etc.), or any combination thereof. In some instances, an organic component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of water or an aqueous buffer solution. In some instances, an aqueous component of the solvent mixture used may comprise at least 1%, 5%, 10%, 15%, 20%, 25%, 30%, 35%, 40%, 45%, 50%, 55%, 60%, 70%, 75%, 80%, 85%, 90%, 95%, 98%, or 99% of the total, or any percentage spanned or adjacent to the range herein, with the balance made up of an organic solvent. The pH of the solvent mixture used may be less than 5, 5, 5, 5, 6, 6, 6.5, 7, 7.5, 8, 8.5, 9, 9.5, 10, or greater than 10, or any value spanned or adjacent to the range described herein.

In some instances, one or more layers of low non-specific binding material may be deposited on and/or conjugated to the substrate surface using a mixture of organic solvents, wherein the dielectric constant of at least once component is less than 40 and constitutes at least 50% of the total mixture by volume. In some instances, the dielectric constant of the at least one component may be less than 10, less than 20, less than 30, less than 40. In some instances, the at least one component constitutes at least 20%, at least 30%, at least 40%, at least 50%, at least 50%, at least 60%, at least 70%, or at least 80% of the total mixture by volume.

As noted, the low non-specific binding supports of the present disclosure exhibit reduced non-specific binding of proteins, nucleic acids, and other components of the hybridization and/or amplification formulation used for solid-phase nucleic acid amplification. The degree of non-specific binding exhibited by a given support surface may be assessed either qualitatively or quantitatively. For example, in some instances, exposure of the surface to fluorescent dyes (e.g., Cy3, Cy5, etc.), fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a qualitative tool for comparison of non-specific binding on supports comprising different surface formulations. In some instances, exposure of the surface to fluorescent dyes, fluorescently-labeled nucleotides, fluorescently-labeled oligonucleotides, and/or fluorescently-labeled proteins (e.g. polymerases) under a standardized set of conditions, followed by a specified rinse protocol and fluorescence imaging may be used as a quantitative tool for comparison of non-specific binding on supports comprising different surface formulations—provided that care has been taken to ensure that the fluorescence imaging is performed under conditions where fluorescence signal is linearly related (or related in a predictable manner) to the number of fluorophores on the support surface (e.g., under conditions where signal saturation and/or self-quenching of the fluorophore is not an issue) and suitable calibration standards are used. In some instances, other techniques known to those of skill in the art, for example, radioisotope labeling and counting methods may be used for quantitative assessment of the degree to which non-specific binding is exhibited by the different support surface formulations of the present disclosure.

Some surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. Some surfaces disclosed herein exhibit a ratio of specific to nonspecific fluorescence of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

As noted, in some instances, the degree of non-specific binding exhibited by the disclosed low-binding supports may be assessed using a standardized protocol for contacting the surface with a labeled protein (e.g., bovine serum albumin (BSA), streptavidin, a DNA polymerase, a reverse transcriptase, a helicase, a single-stranded binding protein (SSB), etc., or any combination thereof), a labeled nucleotide, a labeled oligonucleotide, etc., under a standardized set of incubation and rinse conditions, followed be detection of the amount of label remaining on the surface and comparison of the signal resulting therefrom to an appropriate calibration standard. In some instances, the label may comprise a fluorescent label. In some instances, the label may comprise a radioisotope. In some instances, the label may comprise any other detectable label known to one of skill in the art. In some instances, the degree of non-specific binding exhibited by a given support surface formulation may thus be assessed in terms of the number of non-specifically bound protein molecules (or other molecules) per unit area. In some instances, the low-binding supports of the present disclosure may exhibit non-specific protein binding (or non-specific binding of other specified molecules, e.g., Cy3 dye) of less than 0.001 molecule per $\mu m^2$, less than 0.01 molecule per $\mu m^2$, less than 0.1 molecule per $\mu m^2$, less than 0.25 molecule per $\mu m^2$, less than 0.5 molecule per $\mu m^2$, less than 1 molecule per $\mu m^2$, less than 10 molecules per $\mu m^2$, less than 100 molecules per $\mu m^2$, or less than 1,000 molecules per $\mu m^2$. Those of skill in the art will realize that a given support surface of the present disclosure may exhibit non-specific binding falling anywhere within this range, for example, of less than 86 molecules per $\mu m^2$. For example, some modified surfaces disclosed herein exhibit nonspecific protein binding of less than 0.5 molecule/$um^2$ following contact with a 1 uM solution of Cy3 labeled streptavidin (GE Amersham) in phosphate buffered saline (PBS) buffer for 15 minutes, followed by 3 rinses with deionized water. Some modified surfaces disclosed herein exhibit nonspecific binding of Cy3 dye molecules of less than 0.25 molecules per $um^2$. In independent nonspecific binding assays, 1 uM labeled Cy3 SA (ThermoFisher), 1 uM Cy5 SA dye (ThermoFisher), 10 uM Aminoallyl-dUTP-ATTO-647N (Jena Biosciences), 10 uM Aminoallyl-dUTP-ATTO-Rho11 (Jena Biosciences), 10 uM Aminoallyl-dUTP-ATTO-Rho11 (Jena Biosciences), 10 uM 7-Propargylamino-7-deaza-dGTP-Cy5 (Jena Biosciences), and 10 uM 7-Propargylamino-7-deaza-dGTP-Cy3 (Jena Biosciences) were incubated on the low binding substrates at 37° C. for 15 minutes in a 384 well plate format. Each well was rinsed 2-3× with 50 ul deionized RNase/DNase Free water and 2-3× with 25 mM ACES buffer pH 7.4. The 384 well plates were imaged on a GE Typhoon (GE Healthcare Lifesciences, Pittsburgh, Pa.) instrument using the Cy3, AF555, or Cy5 filter sets (according to dye test performed) as specified by the manufacturer at a PMT gain setting of 800 and resolution of 50-100 μm. For higher resolution imaging, images were collected on an Olympus IX83 microscope (Olympus Corp., Center Valley, Pa.) with a total internal reflectance fluorescence (TIRF) objective (20×, 0.75 NA or 100×, 1.5 NA, Olympus), an sCMOS Andor camera (Zyla 4.2), and excitation wavelengths of 532 nm or 635 nm. Dichroic mirrors were purchased from Semrock (IDEX Health & Science, LLC, Rochester, N.Y.), e.g., 405, 488, 532, or 633 nm dichroic reflectors/beamsplitters, and band pass filters were chosen as 532 LP or 645 LP concordant with the appropriate excitation wavelength. Some modified surfaces disclosed herein exhibit nonspecific binding of dye molecules of less than 0.25 molecules per $\mu m^2$.

In some instances, the surfaces disclosed herein exhibit a ratio of specific to nonspecific binding of a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein. In some instances, the surfaces disclosed herein exhibit a ratio of specific to nonspecific fluorescence signals for a fluorophore such as Cy3 of at least 2, 3, 4, 5, 6, 7, 8, 9, 10, 11, 12, 13, 14, 15, 16, 17, 18, 19, 20, 25, 30, 35, 40, 50, 75, 100, or greater than 100, or any intermediate value spanned by the range herein.

The low-background surfaces consistent with the disclosure herein may exhibit specific dye attachment (e.g., Cy3 attachment) to non-specific dye adsorption (e.g., Cy3 dye adsorption) ratios of at least 3:1, 4:1, 5:1, 6:1, 7:1, 8:1, 9:1, 10:1, 15:1, 20:1, 30:1, 40:1, 50:1, or more than 50 specific dye molecules attached per molecule nonspecifically adsorbed. Similarly, when subjected to an excitation energy, low-background surfaces consistent with the disclosure herein to which fluorophores, e.g., Cy3, have been attached may exhibit ratios of specific fluorescence signal (e.g., arising from Cy3-labeled oligonucleotides attached to the surface) to non-specific adsorbed dye fluorescence signals of at least 3:1, 4:1, 5:1, 6:1, 7:1, 8:1, 9:1, 10:1, 15:1, 20:1, 30:1, 40:1, 50:1, or more than 50:1.

In some instances, the degree of hydrophilicity (or "wettability" with aqueous solutions) of the disclosed support surfaces may be assessed, for example, through the measurement of water contact angles in which a small droplet of water is placed on the surface and its angle of contact with the surface is measured using, e.g., an optical tensiometer. In some instances, a static contact angle may be determined. In some instances, an advancing or receding contact angle may be determined. In some instances, the water contact angle for the hydrophilic, low-binding support surfaced disclosed herein may range from about 0 degrees to about 50 degrees. In some instances, the water contact angle for the hydrophilic, low-binding support surfaced disclosed herein may no more than 50 degrees, 45 degrees, 40 degrees, 35 degrees, 30 degrees, 25 degrees, 20 degrees, 18 degrees, 16 degrees, 14 degrees, 12 degrees, 10 degrees, 8 degrees, 6 degrees, 4 degrees, 2 degrees, or 1 degree. In many cases the contact angle is no more than any value within this range, e.g., no more than 40 degrees. Those of skill in the art will realize that a given hydrophilic, low-binding support surface of the present disclosure may exhibit a water contact angle having a value of anywhere within this range, e.g., about 27 degrees.

In some instances, the hydrophilic surfaces disclosed herein facilitate reduced wash times for bioassays, often due to reduced nonspecific binding of biomolecules to the low-binding surfaces. In some instances, adequate wash steps may be performed in less than 60, 50, 40, 30, 20, 15, 10, or less than 10 seconds. For example, in some instances adequate wash steps may be performed in less than 30 seconds.

Some low-binding surfaces of the present disclosure exhibit significant improvement in stability or durability to prolonged exposure to solvents and elevated temperatures, or to repeated cycles of solvent exposure or changes in temperature. For example, in some instances, the stability of the disclosed surfaces may be tested by fluorescently labeling a functional group on the surface, or a tethered biomolecule (e.g., an oligonucleotide primer) on the surface, and monitoring fluorescence signal before, during, and after prolonged exposure to solvents and elevated temperatures, or to repeated cycles of solvent exposure or changes in temperature. In some instances, the degree of change in the fluorescence used to assess the quality of the surface may be less than 1%, 2%, 3%, 4%, 5%, 10%, 15%, 20%, or 25% over a time period of 1 minute, 2 minutes, 3 minutes, 4 minutes, 5 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 15 hours, 20 hours, 25 hours, 30 hours, 35 hours, 40 hours, 45 hours, 50 hours, or 100 hours of exposure to solvents and/or elevated temperatures (or any combination of these percentages as measured over these time periods). In some instances, the degree of change in the fluorescence used to assess the quality of the surface may be less than 1%, 2%, 3%, 4%, 5%, 10%, 15%, 20%, or 25% over 5 cycles, 10 cycles, 20 cycles, 30 cycles, 40 cycles, 50 cycles, 60 cycles, 70 cycles, 80 cycles, 90 cycles, 100 cycles, 200 cycles, 300 cycles, 400 cycles, 500 cycles, 600 cycles, 700 cycles, 800 cycles, 900 cycles, or 1,000 cycles of repeated exposure to solvent changes and/or changes in temperature (or any combination of these percentages as measured over this range of cycles).

In some instances, the surfaces disclosed herein may exhibit a high ratio of specific signal to nonspecific signal or other background. For example, when used for nucleic acid amplification, some surfaces may exhibit an amplification signal that is at least 3, 4, 5, 6, 7, 8, 9, 10, 15, 20, 30, 40, 50, 75, 100, or greater than 100 fold greater than a signal of an adjacent unpopulated region of the surface. Similarly, some surfaces exhibit an amplification signal that is at least 3, 4, 5, 6, 7, 8, 9, 10, 15, 20, 30, 40, 50, 75, 100, or greater than 100 fold greater than a signal of an adjacent amplified nucleic acid population region of the surface.

Fluorescence excitation energies vary among particular fluorophores and protocols, and may range in excitation wavelength from less than 400 nm to over 800 nm, consistent with fluorophore selection or other parameters of use of a surface disclosed herein.

Accordingly, low background surfaces as disclosed herein exhibit low background fluorescence signals or high contrast to noise (CNR) ratios relative to known surfaces in the art. For example, in some instances, the background fluorescence of the surface at a location that is spatially distinct or removed from a labeled feature on the surface (e.g., a labeled spot, cluster, discrete region, sub-section, or subset of the surface) comprising a hybridized cluster of nucleic acid molecules, or a clonally-amplified cluster of nucleic acid molecules produced by, e.g., 20 cycles of nucleic acid amplification via thermocycling, may be no more than 20×, 10×, 5×, 2×, 1×, 0.5×, 0.1×, or less than 0.1× greater than the background fluorescence measured at that same location prior to performing said hybridization or said 20 cycles of nucleic acid amplification.

In some instances, fluorescence images of the disclosed low background surfaces when used in nucleic acid hybridization or amplification applications to create clusters of hybridized or clonally-amplified nucleic acid molecules (e.g., that have been directly or indirectly labeled with a fluorophore) exhibit contrast-to-noise ratios (CNRs) of at least 10, 20, 30, 40, 50, 60, 70, 80, 90, 100, 110, 120, 130, 140, 150, 160, 170, 180, 190, 20, 210, 220, 230, 240, 250, or greater than 250.

Oligonucleotide Primers and Adapter Sequences:

In general, at least one layer of the one or more layers of low non-specific binding material may comprise functional groups for covalently or non-covalently attaching oligonucleotide molecules, e.g., adapter or primer sequences, or the at least one layer may already comprise covalently or non-covalently attached oligonucleotide adapter or primer sequences at the time that it is deposited on the support surface. In some instances, the oligonucleotides tethered to the polymer molecules of at least one third layer may be distributed at a plurality of depths throughout the layer.

In some instances, the oligonucleotide adapter or primer molecules are covalently coupled to the polymer in solution, i.e., prior to coupling or depositing the polymer on the surface. In some instances, the oligonucleotide adapter or primer molecules are covalently coupled to the polymer after it has been coupled to or deposited on the surface. In some instances, at least one hydrophilic polymer layer comprises a plurality of covalently-attached oligonucleotide adapter or primer molecules. In some instances, at least two, at least three, at least four, or at least five layers of hydrophilic polymer comprise a plurality of covalently-attached adapter or primer molecules.

In some instances, the oligonucleotide adapter or primer molecules may be coupled to the one or more layers of hydrophilic polymer using any of a variety of suitable conjugation chemistries known to those of skill in the art. For example, the oligonucleotide adapter or primer sequences may comprise moieties that are reactive with amine groups, carboxyl groups, thiol groups, and the like. Examples of suitable amine-reactive conjugation chemistries that may be used include, but are not limited to, reactions involving isothiocyanate, isocyanate, acyl azide, NHS ester, sulfonyl chloride, aldehyde, glyoxal, epoxide, oxirane, carbonate, aryl halide, imidoester, carbodiimide, anhydride, and fluorophenyl ester groups. Examples of suitable carboxyl-reactive conjugation chemistries include, but are not limited to, reactions involving carbodiimide compounds, e.g., water soluble EDC (1-ethyl-3-(3-dimethylaminopropyl)carbodiimide.HCL). Examples of suitable sulfydryl-reactive conjugation chemistries include maleimides, haloacetyls and pyridyl disulfides.

One or more types of oligonucleotide molecules may be attached or tethered to the support surface. In some instances, the one or more types of oligonucleotide adapters or primers may comprise spacer sequences, adapter sequences for hybridization to adapter-ligated template library nucleic acid sequences, forward amplification primers, reverse amplification primers, sequencing primers, and/or molecular barcoding sequences, or any combination thereof. In some instances, 1 primer or adapter sequence may be tethered to at least one layer of the surface. In some instances, at least 2, 3, 4, 5, 6, 7, 8, 9, 10, or more than 10 different primer or adapter sequences may be tethered to at least one layer of the surface.

In some instances, the tethered oligonucleotide adapter and/or primer sequences may range in length from about 10 nucleotides to about 100 nucleotides. In some instances, the tethered oligonucleotide adapter and/or primer sequences may be at least 10, at least 20, at least 30, at least 40, at least 50, at least 60, at least 70, at least 80, at least 90, or at least 100 nucleotides in length. In some instances, the tethered oligonucleotide adapter and/or primer sequences may be at most 100, at most 90, at most 80, at most 70, at most 60, at most 50, at most 40, at most 30, at most 20, or at most 10 nucleotides in length. Any of the lower and upper values described in this paragraph may be combined to form a range included within the present disclosure, for example, in some instances the length of the tethered oligonucleotide adapter and/or primer sequences may range from about 20 nucleotides to about 80 nucleotides. Those of skill in the art will recognize that the length of the tethered oligonucleotide adapter and/or primer sequences may have any value within this range, e.g., about 24 nucleotides.

In some instances, the tethered adapter or primer sequences may comprise modifications designed to facilitate the specificity and efficiency of nucleic acid amplification as performed on the low-binding supports. For example, in some instances the primer may comprise polymerase stop points such that the stretch of primer sequence between the surface conjugation point and the modification site is always in single-stranded form and functions as a loading site for 5' to 3' helicases in some helicase-dependent isothermal amplification methods. Other examples of primer modifications that may be used to create polymerase stop points include, but are not limited to, an insertion of a PEG chain into the backbone of the primer between two nucleotides towards the 5' end, insertion of an abasic nucleotide (i.e., a nucleotide that has neither a purine nor a pyrimidine base), or a lesion site which can be bypassed by the helicase.

As will be discussed further in the examples below, it may be desirable to vary the surface density of tethered oligonucleotide adapters or primers on the support surface and/or the spacing of the tethered adapters or primers away from the support surface (e.g., by varying the length of a linker molecule used to tether the adaptors or primers to the surface) in order to "tune" the support for optimal performance when using a given amplification method. As noted below, adjusting the surface density of tethered oligonucleotide adapters or primers may impact the level of specific and/or non-specific amplification observed on the support in a manner that varies according to the amplification method selected. In some instances, the surface density of tethered oligonucleotide adapters or primers may be varied by adjusting the ratio of molecular components used to create the support surface. For example, in the case that an oligonucleotide primer—PEG conjugate is used to create the final layer of a low-binding support, the ratio of the oligonucleotide primer—PEG conjugate to a non-conjugated PEG molecule may be varied. The resulting surface density of tethered primer molecules may then be estimated or measured using any of a variety of techniques known to those of skill in the art. Examples include, but are not limited to, the use of radioisotope labeling and counting methods, covalent coupling of a cleavable molecule that comprises an optically-detectable tag (e.g., a fluorescent tag) that may be cleaved from a support surface of defined area, collected in a fixed volume of an appropriate solvent, and then quantified by comparison of fluorescence signals to that for a calibration solution of known optical tag concentration, or using fluorescence imaging techniques provided that care has been taken with the labeling reaction conditions and image acquisition settings to ensure that the fluorescence signals are linearly related to the number of fluorophores on the surface (e.g., that there is no significant self-quenching of the fluorophores on the surface).

In some instances, the resultant surface density of oligonucleotide adapters or primers on the low binding support surfaces of the present disclosure may range from about 100 primer molecules per $\mu m^2$ to about 1,000,000 primer molecules per $\mu m^2$. In some instances, the surface density of oligonucleotide adapters or primers may be at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per $\mu m^2$. In some instances, the surface density of oligonucleotide adapters or primers may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, or at most 100 molecules per $\mu m^2$. Any of the lower and upper values described in this paragraph may be combined to form a range included within the present disclosure, for example, in some instances the surface density of adapters or primers may range from about 10,000 molecules per $\mu m^2$ to about 100,000 molecules per $\mu m^2$. Those of skill in the art will recognize that the surface density of adapter or primer molecules may have any value within this range, e.g., about 3,800 molecules per $\mu m^2$ in some instances, or about 455,000 molecules per $\mu m^2$ in other instances. In some instances, as will be discussed further below, the surface density of template library nucleic acid sequences (e.g., sample DNA molecules) initially hybridized to adapter or primer sequences on the support surface may be less than or equal to that indicated for the surface density of tethered oligonucleotide primers. In some instances, as will also be discussed further below, the surface density of clonally-amplified template library nucleic acid sequences hybridized to adapter or primer sequences on the support surface may span the same range or a different range as that indicated for the surface density of tethered oligonucleotide adapters or primers.

Local surface densities of adapter or primer molecules as listed above do not preclude variation in density across a surface, such that a surface may comprise a region having an oligo density of, for example, 500,000/$um^2$, while also comprising at least a second region having a substantially different local density.

Hybridization of Nucleic Acid Molecules to Low-Binding Supports:

In some aspects of the present disclosure, hybridization buffer formulations are described which, in combination with the disclosed low-binding supports, provide for improved hybridization rates, hybridization specificity (or stringency), and hybridization efficiency (or yield). As used herein, hybridization specificity is a measure of the ability of tethered adapter sequences, primer sequences, or oligonucleotide sequences in general to correctly hybridize only to completely complementary sequences, while hybridization efficiency is a measure of the percentage of total available tethered adapter sequences, primer sequences, or oligonucleotide sequences in general that are hybridized to complementary sequences.

Improved hybridization specificity and/or efficiency may be achieved through optimization of the hybridization buffer formulation used with the disclosed low-binding surfaces, and will be discussed in more detail in the examples below. Examples of hybridization buffer components that may be adjusted to achieve improved performance include, but are not limited to, buffer type, organic solvent mixtures, buffer pH, buffer viscosity, detergents and zwitterionic components, ionic strength (including adjustment of both monovalent and divalent ion concentrations), antioxidants and reducing agents, carbohydrates, BSA, polyethylene glycol, dextran sulfate, betaine, other additives, and the like.

By way of non-limiting example, suitable buffers for use in formulating a hybridization buffer may include, but are not limited to, phosphate buffered saline (PBS), succinate, citrate, histidine, acetate, Tris, TAPS, MOPS, PIPES, HEPES, MES, and the like. The choice of appropriate buffer will generally be dependent on the target pH of the hybridization buffer solution. In general, the desired pH of the buffer solution will range from about pH 4 to about pH 8.4. In some embodiments, the buffer pH may be at least 4.0, at least 4.5, at least 5.0, at least 5.5, at least 6.0, at least 6.2, at least 6.4, at least 6.6, at least 6.8, at least 7.0, at least 7.2, at least 7.4, at least 7.6, at least 7.8, at least 8.0, at least 8.2, or at least 8.4. In some embodiments, the buffer pH may be at most 8.4, at most 8.2, at most 8.0, at most 7.8, at most 7.6, at most 7.4, at most 7.2, at most 7.0, at most 6.8, at most 6.6, at most 6.4, at most 6.2, at most 6.0, at most 5.5, at most 5.0, at most 4.5, or at most 4.0. Any of the lower and upper values described in this paragraph may be combined to form a range included within the present disclosure, for example, in some instances, the desired pH may range from about 6.4 to about 7.2. Those of skill in the art will recognize that the buffer pH may have any value within this range, for example, about 7.25.

Suitable detergents for use in hybridization buffer formulation include, but are not limited to, zitterionic detergents (e.g., 1-Dodecanoyl-sn-glycero-3-phosphocholine, 3-(4-tert-Butyl-1-pyridinio)-1-propanesulfonate, 3-(N,N-Dimethylmyristylammonio)propanesulfonate, 3-(N,NDimethylmyristylammonio) propanesulfonate, ASB-C80, C7BzO, CHAPS, CHAPS hydrate, CHAPSO, DDMAB, Dimethylethylammoniumpropane sulfonate, N,N-Dimethyldodecylamine Noxide, N-Dodecyl-N,N-dimethyl-3-ammonio-1-propanesulfonate, or N-Dodecyl-N,N-dimethyl-3-ammonio-1-propanesulfonate) and anionic, cationic, and non-ionic detergents. Examples of nonionic detergents include poly(oxyethylene) ethers and related polymers (e.g. Brij®, TWEEN®, TRITON®, TRITON X-100 and IGEPAL® CA-630), bile salts, and glycosidic detergents.

The use of the disclosed low-binding supports either alone or in combination with optimized buffer formulations may yield relative hybridization rates that range from about 2× to about 20× faster than that for a conventional hybridization protocol. In some instances, the relative hybridization rate may be at least 2×, at least 3×, at least 4×, at least 5×, at least 6×, at least 7×, at least 8×, at least 9×, at least 10×, at least 12×, at least 14×, at least 16×, at least 18×, at least 20×, at least 25×, at least 30×, or at least 40× that for a conventional hybridization protocol.

In some instances, the use of the disclosed low-binding supports alone or in combination with optimized buffer formulations may yield total hybridization reaction times (i.e., the time required to reach 90%, 95%, 98%, or 99% completion of the hybridization reaction) of less than 60 minutes, 50 minutes, 40 minutes, 30 minutes, 20 minutes, 15 minutes, 10 minutes, or 5 minutes for any of these completion metrics.

In some instances, the use of the disclosed low-binding supports alone or in combination with optimized buffer formulations may yield improved hybridization specificity compared to that for a conventional hybridization protocol. In some instances, the hybridization specificity that may be achieved is better than 1 base mismatch in 10 hybridization events, 1 base mismatch in 20 hybridization events, 1 base mismatch in 30 hybridization events, 1 base mismatch in 40 hybridization events, 1 base mismatch in 50 hybridization events, 1 base mismatch in 75 hybridization events, 1 base mismatch in 100 hybridization events, 1 base mismatch in 200 hybridization events, 1 base mismatch in 300 hybridization events, 1 base mismatch in 400 hybridization events, 1 base mismatch in 500 hybridization events, 1 base mismatch in 600 hybridization events, 1 base mismatch in 700 hybridization events, 1 base mismatch in 800 hybridization events, 1 base mismatch in 900 hybridization events, 1 base mismatch in 1,000 hybridization events, 1 base mismatch in 2,000 hybridization events, 1 base mismatch in 3,000 hybridization events, 1 base mismatch in 4,000 hybridization events, 1 base mismatch in 5,000 hybridization events, 1 base mismatch in 6,000 hybridization events, 1 base mismatch in 7,000 hybridization events, 1 base mismatch in 8,000 hybridization events, 1 base mismatch in 9,000 hybridization events, or 1 base mismatch in 10,000 hybridization events.

In some instances, the use of the disclosed low-binding supports alone or in combination with optimized buffer formulations may yield improved hybridization efficiency (e.g., the fraction of available oligonucleotide primers on the support surface that are successfully hybridized with target oligonucleotide sequences) compared to that for a conventional hybridization protocol. In some instances, the hybridization efficiency that may be achieved is better than 50%, 60%, 70%, 80%, 85%, 90%, 95%, 98%, or 99% for any of the input target oligonucleotide concentrations specified below and in any of the hybridization reaction times specified above. In some instances, e.g., wherein the hybridization efficiency is less than 100%, the resulting surface density of target nucleic acid sequences hybridized to the support surface may be less than the surface density of oligonucleotide adapter or primer sequences on the surface.

In some instances, use of the disclosed low-binding supports for nucleic acid hybridization (or amplification) applications using conventional hybridization (or amplification) protocols, or optimized hybridization (or amplification) protocols may lead to a reduced requirement for the input concentration of target (or sample) nucleic acid molecules contacted with the support surface. For example, in some instances, the target (or sample) nucleic acid molecules may be contacted with the support surface at a concentration ranging from about 10 pM to about 1 µM (i.e., prior to annealing or amplification). In some instances, the target (or sample) nucleic acid molecules may be administered at a concentration of at least 10 pM, at least 20 pM, at least 30 pM, at least 40 pM, at least 50 pM, at least 100 pM, at least 200 pM, at least 300 pM, at least 400 pM, at least 500 pM, at least 600 pM, at least 700 pM, at least 800 pM, at least 900 pM, at least 1 nM, at least 10 nM, at least 20 nM, at least 30 nM, at least 40 nM, at least 50 nM, at least 60 nM, at least 70 nM, at least 80 nM, at least 90 nM, at least 100 nM, at least 200 nM, at least 300 nM, at least 400 nM, at least 500 nM, at least 600 nM, at least 700 nM, at least 800 nM, at least 900 nM, or at least 1 µM. In some instances, the target (or sample) nucleic acid molecules may be administered at a concentration of at most 1 µM, at most 900 nM, at most 800 nm, at most 700 nM, at most 600 nM, at most 500 nM, at most 400 nM, at most 300 nM, at most 200 nM, at most 100 nM, at most 90 nM, at most 80 nM, at most 70 nM, at most 60 nM, at most 50 nM, at most 40 nM, at most 30 nM, at most 20 nM, at most 10 nM, at most 1 nM, at most 900 pM, at most 800 pM, at most 700 pM, at most 600 pM, at most 500 pM, at most 400 pM, at most 300 pM, at most 200 pM, at most 100 pM, at most 90 pM, at most 80 pM, at most 70 pM, at most 60 pM, at most 50 pM, at most 40 pM, at most 30 pM, at most 20 pM, or at most 10 pM. Any of the lower and upper values described in this paragraph may be combined to form a range included within the present disclosure, for example, in some instances the target (or sample) nucleic acid molecules may be administered at a concentration ranging from about 90 pM to about 200 nM. Those of skill in the art will recognize that the target (or sample) nucleic acid molecules may be administered at a concentration having any value within this range, e.g., about 855 nM.

In some instances, the use of the disclosed low-binding supports alone or in combination with optimized hybridization buffer formulations may result in a surface density of hybridized target (or sample) oligonucleotide molecules (i.e., prior to performing any subsequent solid-phase or clonal amplification reaction) ranging from about from about 0.0001 target oligonucleotide molecules per $\mu m^2$ to about 1,000,000 target oligonucleotide molecules per $\mu m^2$. In some instances, the surface density of hybridized target oligonucleotide molecules may be at least 0.0001, at least 0.0005, at least 0.001, at least 0.005, at least 0.01, at least 0.05, at least 0.1, at least 0.5, at least 1, at least 5, at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1,000, at least 1,500, at least 2,000, at least 2,500, at least 3,000, at least 3,500, at least 4,000, at least 4,500, at least 5,000, at least 5,500, at least 6,000, at least 6,500, at least 7,000, at least 7,500, at least 8,000, at least 8,500, at least 9,000, at least 9,500, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, or at least 1,000,000 molecules per $\mu m^2$. In some instances, the surface density of hybridized target oligonucleotide molecules may be at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,500, at most 9,000, at most 8,500, at most 8,000, at most 7,500, at most 7,000, at most 6,500, at most 6,000, at most 5,500, at most 5,000, at most 4,500, at most 4,000, at most 3,500, at most 3,000, at most 2,500, at most 2,000, at most 1,500, at most 1,000, at most 900, at most 800, at most 700, at most 600, at most 500, at most 400, at most 300, at most 200, at most 100, at most 90, at most 80, at most 70, at most 60, at most 50, at most 40, at most 30, at most 20, at most 10, at most 5, at most 1, at most 0.5, at most 0.1, at most 0.05, at most 0.01, at most 0.005, at most 0.001, at most 0.0005, or at most 0.0001 molecules per $\mu m^2$. Any of the lower and upper values described in this paragraph may be combined to form a range included within the present disclosure, for example, in some instances the surface density of hybridized target oligonucleotide molecules may range from about 3,000 molecules per $\mu m^2$ to about 20,000 molecules per $\mu m^2$. Those of skill in the art will recognize that the surface density of hybridized target oligonucleotide molecules may have any value within this range, e.g., about 2,700 molecules per $\mu m^2$.

Stated differently, in some instances the use of the disclosed low-binding supports alone or in combination with optimized hybridization buffer formulations may result in a surface density of hybridized target (or sample) oligonucleotide molecules (i.e., prior to performing any subsequent solid-phase or clonal amplification reaction) ranging from about 100 hybridized target oligonucleotide molecules per $mm^2$ to about $1 \times 10^7$ oligonucleotide molecules per $mm^2$ or from about 100 hybridized target oligonucleotide molecules per $mm^2$ to about $1 \times 10^{12}$ hybridized target oligonucleotide molecules per $mm^2$. In some instances, the surface density of hybridized target oligonucleotide molecules may be at least 100, at least 500, at least 1,000, at least 4,000, at least 5,000, at least 6,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ molecules per $mm^2$. In some instances, the surface density of hybridized target oligonucleotide molecules may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per $mm^2$. Any of the lower and upper values described in this paragraph may be combined to form a range included within the present disclosure, for example, in some instances the surface density of hybridized target oligonucleotide molecules may range from about 5,000 molecules per $mm^2$ to about 50,000 molecules per $mm^2$. Those of skill in the art will recognize that the surface density of hybridized target oligonucleotide molecules may have any value within this range, e.g., about 50,700 molecules per $mm^2$.

In some instances, the target (or sample) oligonucleotide molecules (or nucleic acid molecules) hybridized to the oligonucleotide adapter or primer molecules attached to the low-binding support surface may range in length from about 0.02 kilobases (kb) to about 20 kb or from about 0.1 kilobases (kb) to about 20 kb. In some instances, the target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 0.6 kb in length, at least 0.7 kb in length, at least 0.8 kb in length, at least 0.9 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, at least 20 kb in length, at least 30 kb in length, or at least 40 kb in length, or any intermediate value spanned by the range described herein, e.g., at least 0.85 kb in length.

In some instances, the target (or sample) oligonucleotide molecules (or nucleic acid molecules) may comprise single-stranded or double-stranded, multimeric nucleic acid molecules further comprising repeats of a regularly occurring monomer unit. In some instances, the single-stranded or double-stranded, multimeric nucleic acid molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, at least 30 kb in length, or at least 40 kb in length, or any intermediate value spanned by the range described herein, e.g., about 2.45 kb in length.

In some instances, the target (or sample) oligonucleotide molecules (or nucleic acid molecules) may comprise single-stranded or double-stranded multimeric nucleic acid molecules comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 17. Thus, in some instances, the surface density of hybridized target sequences in terms of the number of copies of a target sequence per unit area of the support surface may exceed the surface density of oligonucleotide primers even if the hybridization efficiency is less than 100%.

Nucleic Acid Surface Amplification (NASA):

As used herein, the phrase "nucleic acid surface amplification" (NASA) is used interchangeably with the phrase "solid-phase nucleic acid amplification" (or simply "solid-phase amplification"). In some aspects of the present disclosure, nucleic acid amplification formulations are described which, in combination with the disclosed low-binding supports, provide for improved amplification rates, amplification specificity, and amplification efficiency. As used herein, specific amplification refers to amplification of template library oligonucleotide strands that have been tethered to the solid support either covalently or non-covalently. As used herein, non-specific amplification refers to amplification of primer-dimers or other non-template nucleic acids. As used herein, amplification efficiency is a measure of the percentage of tethered oligonucleotides on the support surface that are successfully amplified during a given amplification cycle or amplification reaction. Nucleic acid amplification performed on surfaces disclosed herein may obtain amplification efficiencies of at least 50%, 60%, 70%, 80%, 90%, 95%, or greater than 95%, such as 98% or 99%.

Any of a variety of thermal cycling or isothermal nucleic acid amplification schemes may be used with the disclosed low-binding supports. Examples of nucleic acid amplification methods that may be utilized with the disclosed low-binding supports include, but are not limited to, polymerase chain reaction (PCR), multiple displacement amplification (MDA), transcription-mediated amplification (TMA), nucleic acid sequence-based amplification (NASBA), strand displacement amplification (SDA), real-time SDA, bridge amplification, isothermal bridge amplification, rolling circle amplification, circle-to-circle amplification, helicase-dependent amplification, recombinase-dependent amplification, or single-stranded binding (SSB) protein-dependent amplification.

Often, improvements in amplification rate, amplification specificity, and amplification efficiency may be achieved using the disclosed low-binding supports alone or in combination with formulations of the amplification reaction components. In addition to inclusion of nucleotides, one or more polymerases, helicases, single-stranded binding proteins, etc. (or any combination thereof), the amplification reaction mixture may be adjusted in a variety of ways to achieve improved performance including, but are not limited to, choice of buffer type, buffer pH, organic solvent mixtures, buffer viscosity, detergents and zwitterionic components, ionic strength (including adjustment of both monovalent and divalent ion concentrations), antioxidants and reducing agents, carbohydrates, BSA, polyethylene glycol, dextran sulfate, betaine, other additives, and the like.

The use of the disclosed low-binding supports alone or in combination with optimized amplification reaction formulations may yield increased amplification rates compared to those obtained using conventional supports and amplification protocols. In some instances, the relative amplification rates that may be achieved may be at least 2×, at least 3×, at least 4×, at least 5×, at least 6×, at least 7×, at least 8×, at least 9×, at least 10×, at least 12×, at least 14×, at least 16×, at least 18×, or at least 20× that for use of conventional supports and amplification protocols for any of the amplification methods described above.

In some instances, the use of the disclosed low-binding supports alone or in combination with optimized buffer formulations may yield total amplification reaction times (i.e., the time required to reach 90%, 95%, 98%, or 99% completion of the amplification reaction) of less than 180 mins, 120 mins, 90 min, 60 minutes, 50 minutes, 40 minutes, 30 minutes, 20 minutes, 15 minutes, 10 minutes, 5 minutes, 3 minutes, 1 minute, 50 s, 40 s, 30 s, 20 s, or 10 s for any of these completion metrics.

Some low-binding support surfaces disclosed herein exhibit a ratio of specific binding to nonspecific binding of a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein. Some surfaces disclosed herein exhibit a ratio of specific to nonspecific fluorescence signal for a fluorophore such as Cy3 of at least 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, 20:1, 25:1, 30:1, 35:1, 40:1, 50:1, 75:1, 100:1, or greater than 100:1, or any intermediate value spanned by the range herein.

In some instances, the use of the disclosed low-binding supports alone or in combination with optimized amplification buffer formulations may enable faster amplification reaction times (i.e., the times required to reach 90%, 95%, 98%, or 99% completion of the amplification reaction) of no more than 60 minutes, 50 minutes, 40 minutes, 30 minutes, 20 minutes, or 10 minutes. Similarly, use of the disclosed low-binding supports alone or in combination with optimized buffer formulations may enable amplification reactions to be completed in some cases in no more than 2, 3, 4, 5, 6, 7, 8, 9, 10, 15, or no more than 30 cycles.

In some instances, the use of the disclosed low-binding supports alone or in combination with optimized amplification reaction formulations may yield increased specific amplification and/or decreased non-specific amplification compared to that obtained using conventional supports and amplification protocols. In some instances, the resulting ratio of specific amplification-to-non-specific amplification that may be achieved is at least 4:1 5:1, 6:1, 7:1, 8:1, 9:1, 10:1, 20:1, 30:1, 40:1, 50:1, 60:1, 70:1, 80:1, 90:1, 100:1, 200:1, 300:1, 400:1, 500:1, 600:1, 700:1, 800:1, 900:1, or 1,000:1.

In some instances, the use of the low-binding supports alone or in combination with optimized amplification reaction formulations may yield increased amplification efficiency compared to that obtained using conventional supports and amplification protocols. In some instances, the amplification efficiency that may be achieved is better than 50%, 60%, 70% 80%, 85%, 90%, 95%, 98%, or 99% in any of the amplification reaction times specified above.

In some instances, the clonally-amplified target (or sample) oligonucleotide molecules (or nucleic acid molecules) hybridized to the oligonucleotide adapter or primer molecules attached to the low-binding support surface may range in length from about 0.02 kilobases (kb) to about 20 kb or from about 0.1 kilobases (kb) to about 20 kb. In some instances, the clonally-amplified target oligonucleotide molecules may be at least 0.001 kb, at least 0.005 kb, at least 0.01 kb, at least 0.02 kb, at least 0.05 kb, at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., at least 0.85 kb in length.

In some instances, the clonally-amplified target (or sample) oligonucleotide molecules (or nucleic acid molecules) may comprise single-stranded or double-stranded, multimeric nucleic acid molecules further comprising repeats of a regularly occurring monomer unit. In some instances, the clonally-amplified single-stranded or double-stranded, multimeric nucleic acid molecules may be at least 0.1 kb in length, at least 0.2 kb in length, at least 0.3 kb in length, at least 0.4 kb in length, at least 0.5 kb in length, at least 1 kb in length, at least 2 kb in length, at least 3 kb in length, at least 4 kb in length, at least 5 kb in length, at least 6 kb in length, at least 7 kb in length, at least 8 kb in length, at least 9 kb in length, at least 10 kb in length, at least 15 kb in length, or at least 20 kb in length, or any intermediate value spanned by the range described herein, e.g., about 2.45 kb in length.

In some instances, the clonally-amplified target (or sample) oligonucleotide molecules (or nucleic acid molecules) may comprise single-stranded or double-stranded multimeric nucleic acid molecules comprising from about 2 to about 100 copies of a regularly repeating monomer unit. In some instances, the number of copies of the regularly repeating monomer unit may be at least 2, at least 3, at least 4, at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, and at least 100. In some instances, the number of copies of the regularly repeating monomer unit may be at most 100, at most 95, at most 90, at most 85, at most 80, at most 75, at most 70, at most 65, at most 60, at most 55, at most 50, at most 45, at most 40, at most 35, at most 30, at most 25, at most 20, at most 15, at most 10, at most 5, at most 4, at most 3, or at most 2. Any of the lower and upper values described in this paragraph may be combined to form a range included within the present disclosure, for example, in some instances the number of copies of the regularly repeating monomer unit may range from about 4 to about 60. Those of skill in the art will recognize that the number of copies of the regularly repeating monomer unit may have any value within this range, e.g., about 12. Thus, in some instances, the surface density of clonally-amplified target sequences in terms of the number of copies of a target sequence per unit area of the support surface may exceed the surface density of oligonucleotide primers even if the hybridization and/or amplification efficiencies are less than 100%.

In some instances, the use of the disclosed low-binding supports alone or in combination with optimized amplification reaction formulations may yield increased clonal copy number compared to that obtained using conventional supports and amplification protocols. In some instances, e.g., wherein the clonally-amplified target (or sample) oligonucleotide molecules comprise concatenated, multimeric repeats of a monomeric target sequence, the clonal copy number may be substantially smaller than compared to that obtained using conventional supports and amplification protocols. Thus, in some instances, the clonal copy number may range from about 1 molecule to about 100,000 molecules (e.g., target sequence molecules) per amplified colony. In some instances, the clonal copy number may be at least 1, at least 5, at least 10, at least 50, at least 100, at least 500, at least 1,000, at least 2,000, at least 3,000, at least 4,000, at least 5,000, at least 6,000, at least 7,000, at least 8,000, at least 9,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, or at least 100,000 molecules per amplified colony. In some instances, the clonal copy number may be at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 9,000, at most 8,000, at most 7,000, at most 6,000, at most 5,000, at most 4,000, at most 3,000, at most 2,000, at most 1,000, at most 500, at most 100, at most 50, at most 10, at most 5, or at most 1 molecule per amplified colony. Any of the lower and upper values described in this paragraph may be combined to form a range included within the present disclosure, for example, in some instances the clonal copy number may range from about 2,000 molecules to about 9,000 molecules. Those of skill in the art will recognize that the clonal copy number may have any value within this range, e.g., about 2,220 molecules in some instances, or about 2 molecules in others.

As noted above, in some instances the amplified target (or sample) oligonucleotide molecules (or nucleic acid molecules) may comprise concatenated, multimeric repeats of a monomeric target sequence. In some instances, the amplified target (or sample) oligonucleotide molecules (or nucleic acid molecules) may comprise a plurality of molecules each of which comprises a single monomeric target sequence. Thus, the use of the disclosed low-binding supports alone or in combination with optimized amplification reaction formulations may result in a surface density of target sequence copies that ranges from about 100 target sequence copies per $mm^2$ to about $1 \times 10^{12}$ target sequence copies per $mm^2$. In some instances, the surface density of target sequence copies may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ of clonally amplified target sequence molecules per $mm^2$. In some instances, the surface density of target sequence copies may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 target sequence copies per $mm^2$. Any of the lower and upper values described in this paragraph may be combined to form a range included within the present disclosure, for example, in some instances the surface density of target sequence copies may range from about 1,000 target sequence copies per $mm^2$ to about 65,000 target sequence copies $mm^2$. Those of skill in the art will recognize that the surface density of target sequence copies may have any value within this range, e.g., about 49,600 target sequence copies per $mm^2$.

In some instances, the use of the disclosed low-binding supports alone or in combination with optimized amplification buffer formulations may result in a surface density of clonally-amplified target (or sample) oligonucleotide molecules (or clusters) ranging from about from about 100 molecules per $mm^2$ to about $1 \times 10^{12}$ colonies per $mm^2$. In some instances, the surface density of clonally-amplified molecules may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ molecules per $mm^2$. In some instances, the surface density of clonally-amplified molecules may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per $mm^2$. Any of the lower and upper values described in this paragraph may be combined to form a range included within the present disclosure, for example, in some instances the surface density of clonally-amplified molecules may range from about 5,000 molecules per $mm^2$ to about 50,000 molecules per $mm^2$. Those of skill in the art will recognize that the surface density of clonally-amplified colonies may have any value within this range, e.g., about 48,800 molecules per $mm^2$.

In some instances, the use of the disclosed low-binding supports alone or in combination with optimized amplification buffer formulations may result in a surface density of clonally-amplified target (or sample) oligonucleotide molecules (or clusters) ranging from about from about 100 molecules per $mm^2$ to about $1 \times 10^{12}$ colonies per $mm^2$. In some instances, the surface density of clonally-amplified molecules may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ molecules per $mm^2$. In some instances, the surface density of clonally-amplified molecules may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 molecules per mm$^2$. Any of the lower and upper values described in this paragraph may be combined to form a range included within the present disclosure, for example, in some instances the surface density of clonally-amplified molecules may range from about 5,000 molecules per mm$^2$ to about 50,000 molecules per mm$^2$. Those of skill in the art will recognize that the surface density of clonally-amplified colonies may have any value within this range, e.g., about 48,800 molecules per mm$^2$.

In some instances, the use of the disclosed low-binding supports alone or in combination with optimized amplification buffer formulations may result in a surface density of clonally-amplified target (or sample) oligonucleotide colonies (or clusters) ranging from about from about 100 colonies per mm$^2$ to about $1 \times 10^{12}$ colonies per mm$^2$. In some instances, the surface density of clonally-amplified colonies may be at least 100, at least 500, at least 1,000, at least 5,000, at least 10,000, at least 15,000, at least 20,000, at least 25,000, at least 30,000, at least 35,000, at least 40,000, at least 45,000, at least 50,000, at least 55,000, at least 60,000, at least 65,000, at least 70,000, at least 75,000, at least 80,000, at least 85,000, at least 90,000, at least 95,000, at least 100,000, at least 150,000, at least 200,000, at least 250,000, at least 300,000, at least 350,000, at least 400,000, at least 450,000, at least 500,000, at least 550,000, at least 600,000, at least 650,000, at least 700,000, at least 750,000, at least 800,000, at least 850,000, at least 900,000, at least 950,000, at least 1,000,000, at least 5,000,000, at least $1 \times 10^7$, at least $5 \times 10^7$, at least $1 \times 10^8$, at least $5 \times 10^8$, at least $1 \times 10^9$, at least $5 \times 10^9$, at least $1 \times 10^{10}$, at least $5 \times 10^{10}$, at least $1 \times 10^{11}$, at least $5 \times 10^{11}$, or at least $1 \times 10^{12}$ colonies per mm$^2$. In some instances, the surface density of clonally-amplified colonies may be at most $1 \times 10^{12}$, at most $5 \times 10^{11}$, at most $1 \times 10^{11}$, at most $5 \times 10^{10}$, at most $1 \times 10^{10}$, at most $5 \times 10^9$, at most $1 \times 10^9$, at most $5 \times 10^8$, at most $1 \times 10^8$, at most $5 \times 10^7$, at most $1 \times 10^7$, at most 5,000,000, at most 1,000,000, at most 950,000, at most 900,000, at most 850,000, at most 800,000, at most 750,000, at most 700,000, at most 650,000, at most 600,000, at most 550,000, at most 500,000, at most 450,000, at most 400,000, at most 350,000, at most 300,000, at most 250,000, at most 200,000, at most 150,000, at most 100,000, at most 95,000, at most 90,000, at most 85,000, at most 80,000, at most 75,000, at most 70,000, at most 65,000, at most 60,000, at most 55,000, at most 50,000, at most 45,000, at most 40,000, at most 35,000, at most 30,000, at most 25,000, at most 20,000, at most 15,000, at most 10,000, at most 5,000, at most 1,000, at most 500, or at most 100 colonies per mm$^2$. Any of the lower and upper values described in this paragraph may be combined to form a range included within the present disclosure, for example, in some instances the surface density of clonally-amplified colonies may range from about 5,000 colonies per mm$^2$ to about 50,000 colonies per mm$^2$. Those of skill in the art will recognize that the surface density of clonally-amplified colonies may have any value within this range, e.g., about 48,800 colonies per mm$^2$.

In some cases the use of the disclosed low-binding supports alone or in combination with optimized amplification reaction formulations may yield signal from the amplified and labeled nucleic acid populations (e.g., a fluorescence signal) that has a coefficient of variance of no greater than 50%, such as 50%, 40%, 30%, 20%, 15%, 10%, 5%, or less than 5%.

In some cases, the support surfaces and methods as disclosed herein allow amplification at elevated extension temperatures, such as at 15 C, 20 C, 25 C, 30 C, 40 C, or greater, or for example at about 21 C or 23 C.

In some cases, the use of the support surfaces and methods as disclosed herein enable simplified amplification reactions. For example, in some cases amplification reactions are performed using no more than 1, 2, 3, 4, or 5 discrete reagents.

In some cases, the use of the support surfaces and methods as disclosed herein enable the use of simplified temperature profiles during amplification, such that reactions are executed at temperatures ranging from a low temperature of 15 C, 20 C, 25 C, 30 C, or 40 C, to a high temperature of 40 C, 45 C, 50 C, 60 C, 65 C, 70 C, 75 C, 80 C, or greater than 80 C, for example, such as a range of 20 C to 65 C.

Amplification reactions are also improved such that lower amounts of template (e.g., target or sample molecules) are sufficient to lead to discernable signals on a surface, such as 1 pM, 2 pM, 5 pM, 10 pM, 15 pM, 20 pM, 30 pM, 40 pM, 50 pM, 60 pM, 70 pM, 80 pM, 90 pM, 100 pM, 200 pM, 300 pM, 400 pM, 500 pM, 600 pM, 700 pM, 800 pM, 900 pM, 1,000 pM, 2,000 pM, 3,000 pM, 4,000 pM, 5,000 pM, 6,000 pM, 7,000 pM, 8,000 pM, 9,000 pM, 10,000 pM or greater than 10,000 pM of a sample, such as 500 nM. In exemplary embodiments, inputs of about 100 pM are sufficient to generate signals for reliable signal determination.

Fluorescence Imaging of Support Surfaces:

The disclosed solid-phase nucleic acid amplification reaction formulations and low-binding supports may be used in any of a variety of nucleic acid analysis applications, e.g., nucleic acid base discrimination, nucleic acid base classification, nucleic acid base calling, nucleic acid detection applications, nucleic acid sequencing applications, and nucleic acid-based (genetic and genomic) diagnostic applications. In many of these applications, fluorescence imaging techniques may be used to monitor hybridization, amplification, and/or sequencing reactions performed on the low-binding supports.

Fluorescence imaging may be performed using any of a variety of fluorophores, fluorescence imaging techniques, and fluorescence imaging instruments known to those of skill in the art. Examples of suitable fluorescence dyes that may be used (e.g., by conjugation to nucleotides, oligonucleotides, or proteins) include, but are not limited to, fluorescein, rhodamine, coumarin, cyanine, and derivatives thereof, including the cyanine derivatives Cyanine dye-3 (Cy3), Cyanine dye-5 (Cy5), Cyanine dye-7 (Cy7), etc. Examples of fluorescence imaging techniques that may be used include, but are not limited to, fluorescence microscopy imaging, fluorescence confocal imaging, two-photon fluorescence, and the like. Examples of fluorescence imaging instruments that may be used include, but are not limited to, fluorescence microscopes equipped with an image sensor or camera, confocal fluorescence microscopes, two-photon fluorescence microscopes, or custom instruments that comprise a suitable selection of light sources, lenses, mirrors, prisms, dichroic reflectors, apertures, and image sensors or cameras, etc. A non-limiting example of a fluorescence microscope equipped for acquiring images of the disclosed low-binding support surfaces and clonally-amplified colonies (or clusters) of target nucleic acid sequences hybridized thereon is the Olympus IX83 inverted fluorescence microscope equipped with) 20×, 0.75 NA, a 532 nm light source, a bandpass and dichroic mirror filter set optimized for 532 nm long-pass excitation and Cy3 fluorescence emission filter, a Semrock 532 nm dichroic reflector, and a camera (Andor sCMOS, Zyla 4.2) where the excitation light intensity is adjusted to avoid signal saturation. Often, the support surface may be immersed in a buffer (e.g., 25 mM ACES, pH 7.4 buffer) while the image is acquired.

Figure 6A:
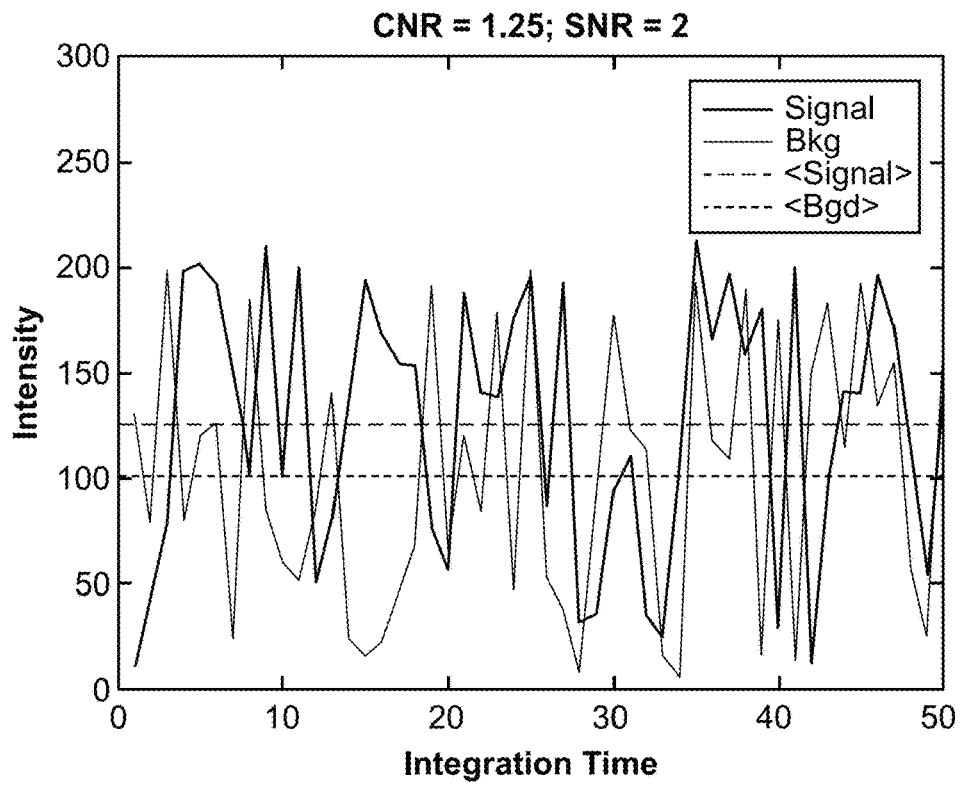
FIGS. 6A-B provide examples of simulated fluorescence intensity data that illustrate the difference between using signal-to-noise ratio (SNR) and contrast-to-noise ratio (CNR) as metrics of data quality in nucleic acid sequencing and base-calling applications.
Figure 6B:
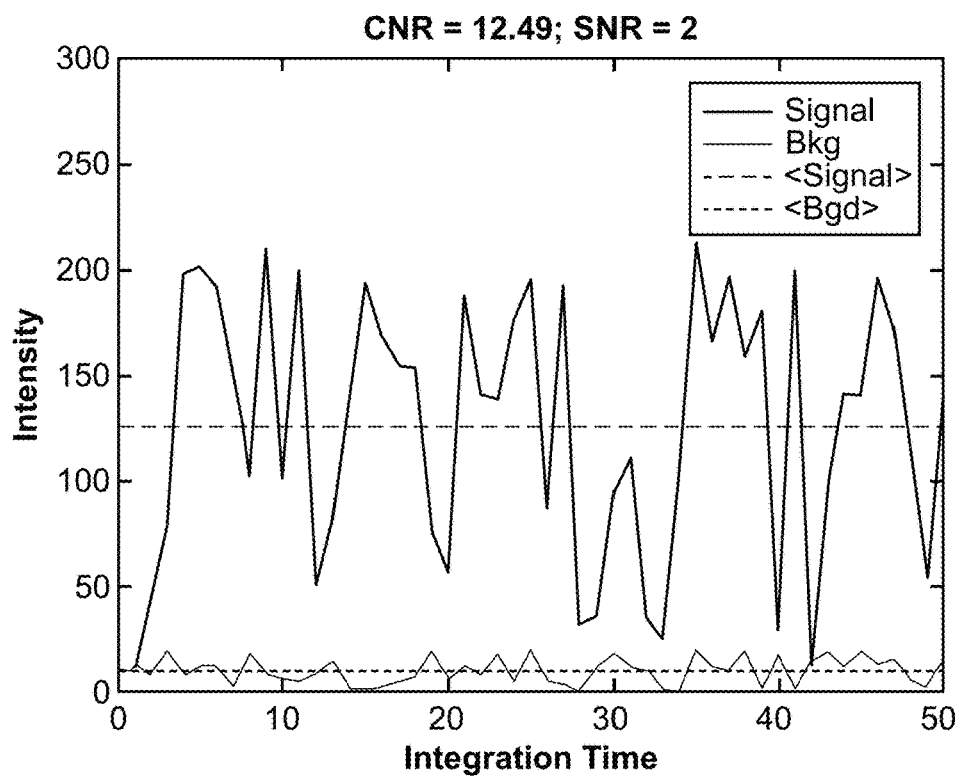
Figure 7:
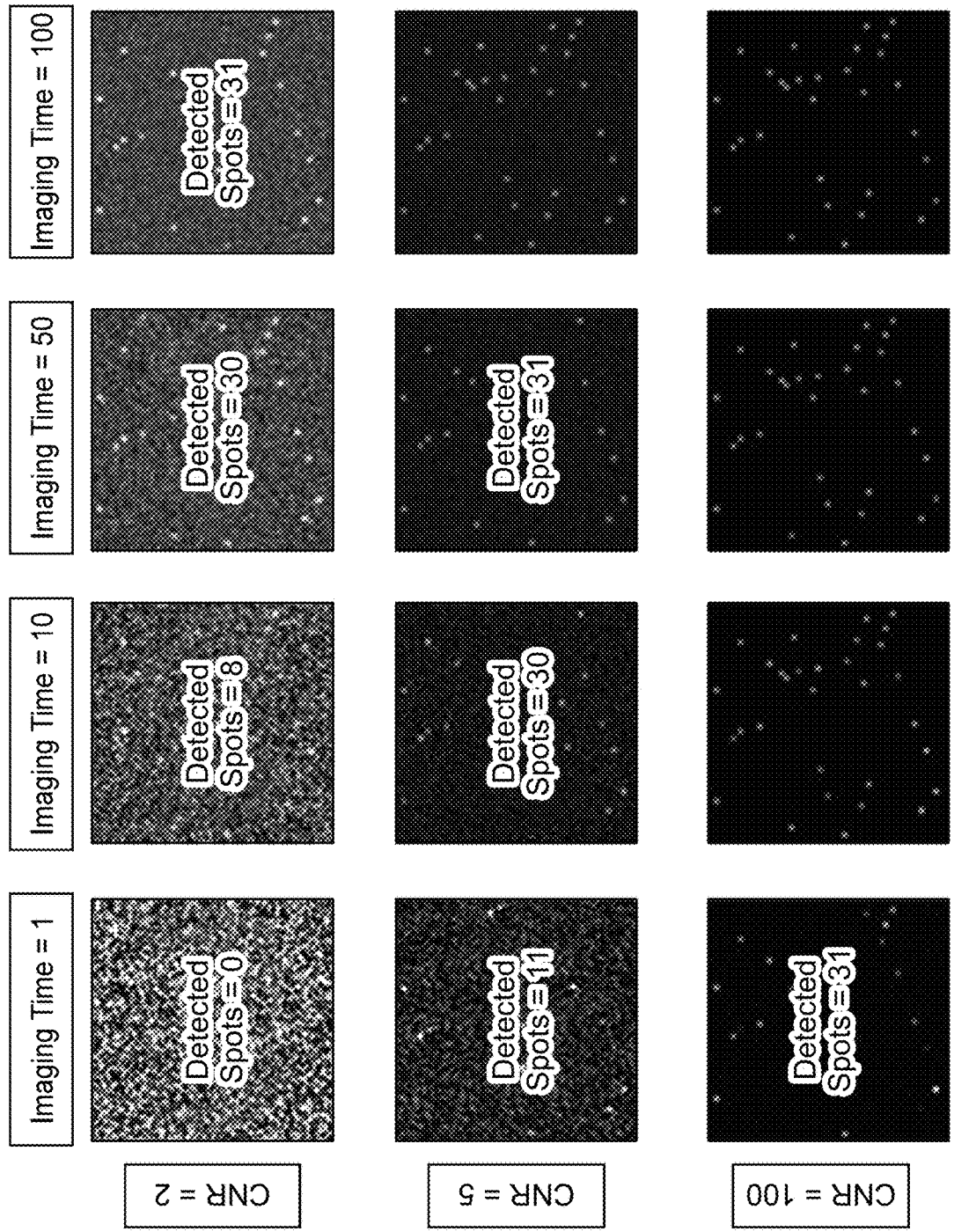
FIG. 7 provides an example of how improved CNR impacts the imaging times required for accurate detection of and signal classification (base-calling) for clonally-amplified nucleic acid colonies on a solid support.
Figure 12:
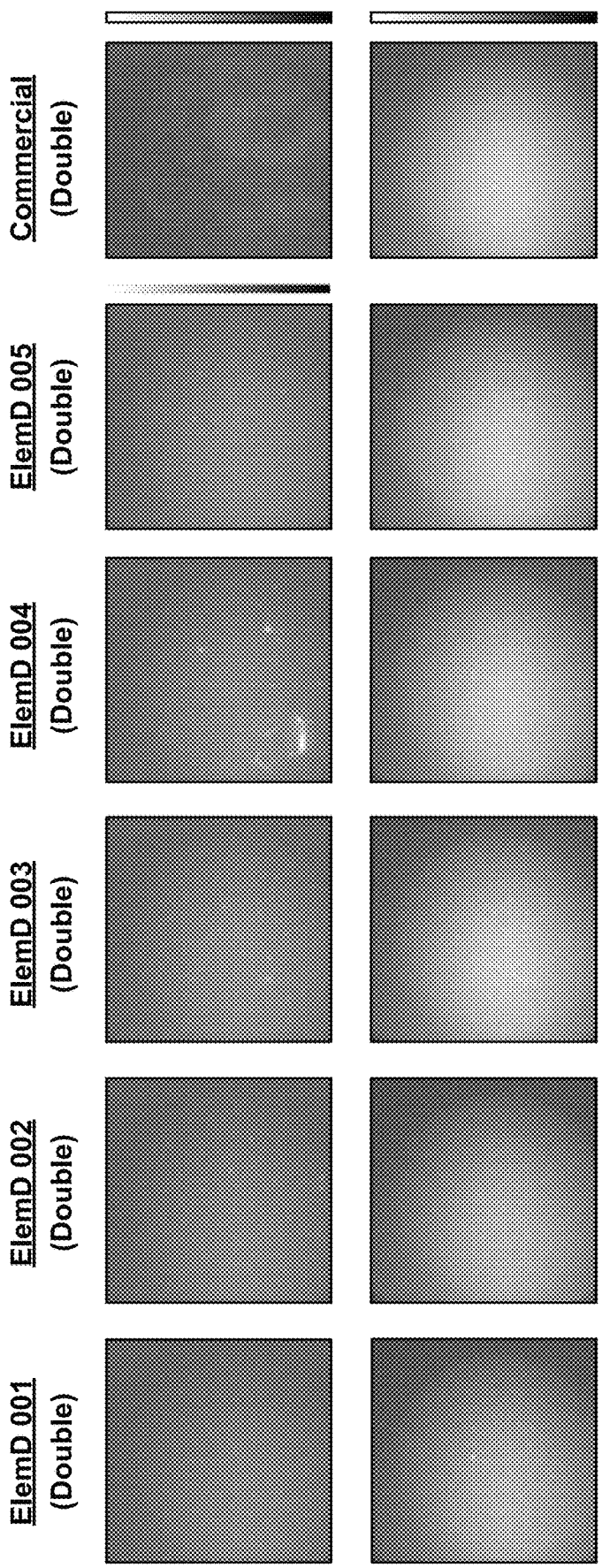
FIG. 12 provides examples of replicate images acquired during a non-specific binding test of substrate surfaces treated according to different surface modification protocols.
Figure 13:
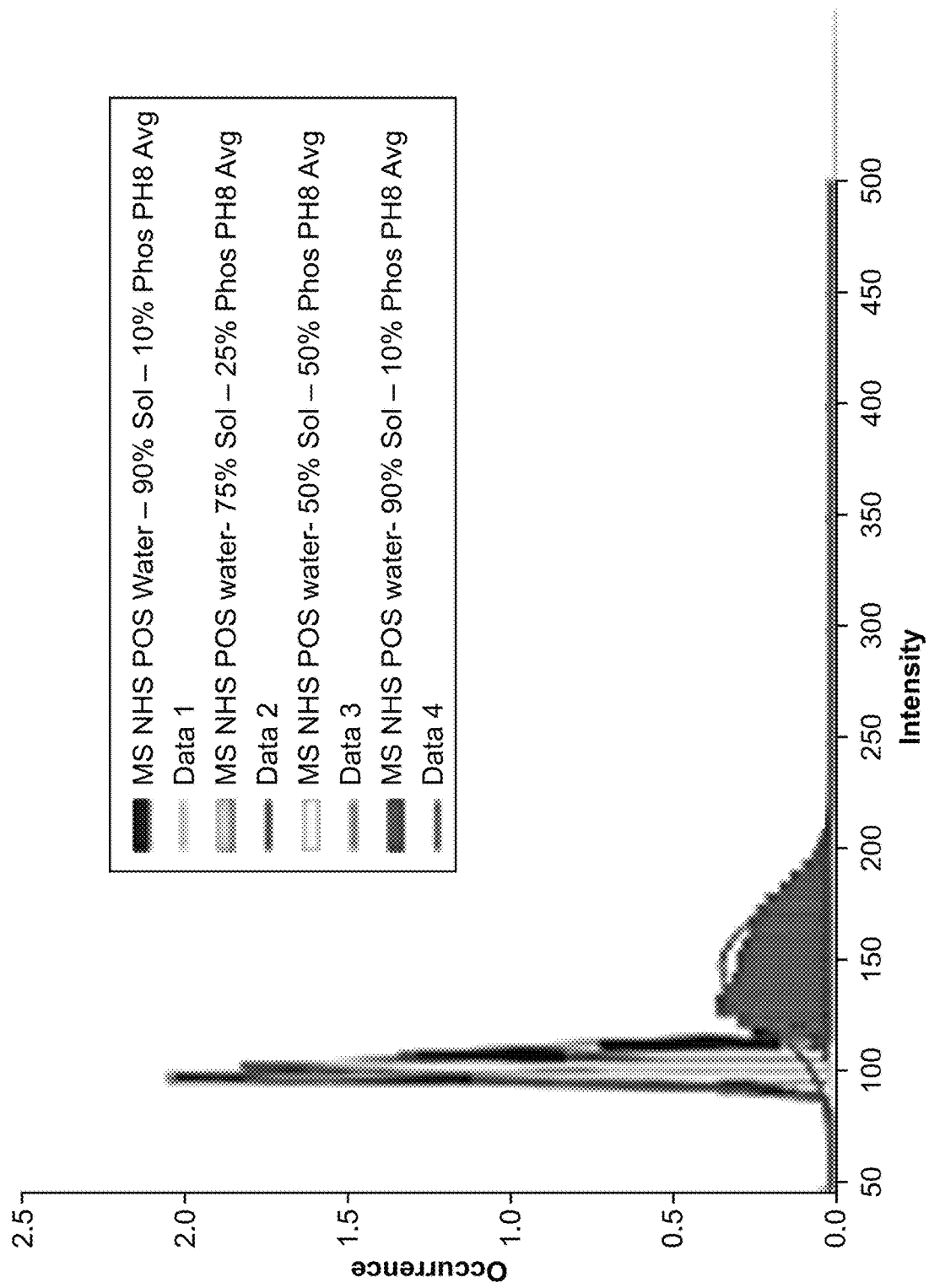
FIG. 13 provides an example of data for non-specific binding of a sequencing dye mixture to substrate surfaces treated according to different surface modification protocols. For comparison purposes, the fluorescence intensity measured under the same set of experimental conditions for non-specific binding of the sequencing dye mixture to a single bead grafted with Cy3 labeled oligonucleotides is about 1,500 counts.

In some instances, the performance of nucleic acid hybridization and/or amplification reactions using the disclosed reaction formulations and low-binding supports may be assessed using fluorescence imaging techniques, where the contrast-to-noise ratio (CNR) of the images provides a key metric in assessing amplification specificity and non-specific binding on the support. CNR is commonly defined as: CNR=(Signal−Background)/Noise. The background term is commonly taken to be the signal measured for the interstitial regions surrounding a particular feature (diffraction limited spot, DLS) in a specified region of interest (ROI). While signal-to-noise ratio (SNR) is often considered to be a benchmark of overall signal quality, it can be shown that improved CNR can provide a significant advantage over SNR as a benchmark for signal quality in applications that require rapid image capture (e.g., sequencing applications for which cycle times must be minimized), as shown in the example below. As illustrated in FIGS. 6A and 6B, at high CNR the imaging time required to reach accurate discrimination (and thus accurate base-calling in the case of sequencing applications) can be drastically reduced even with moderate improvements in CNR. FIGS. 6A and 6B provide simulation data for signal and background intensities (solid lines) and integrated average values (dashed lines) measured as a function of CNR (CNR=1.25 in FIG. 6A and 12.49 in FIG. 6B) and integration time (SNR=2 in both figures), which illustrate the improved discrimination that may be achieved by using CNR as the signal quality metric. FIG. 7 provides examples of the impact of improved CNR in image data on the imaging integration time required to accurately detect features such as clonally-amplified nucleic acid colonies on the support surface.

Figure 8:
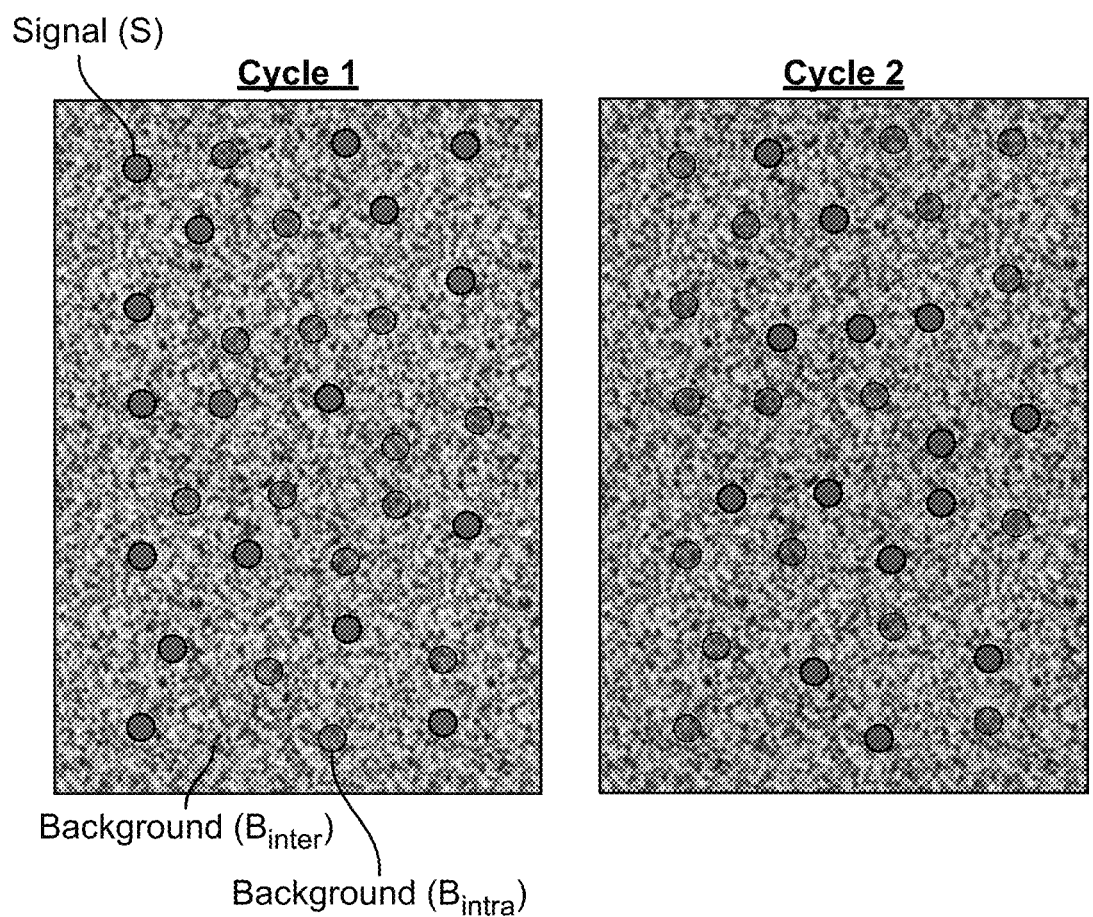
FIG. 8 illustrates the different images acquired for different cycles of a nucleic acid sequencing reaction performed on a solid support due to the different labeled nucleotides incorporated into the complementary strands for each clonally-amplified template molecule. The figure also illustrates the different background contributions to the overall detection signal for detection platforms that require iterative spot detection through distinguishing nucleotide-specific signal from noisy interstitial background and intrastitial background images.

In most ensemble-based sequencing approaches, the background term is typically measured as the signal associated with 'interstitial' regions (see FIG. 8). In addition to "interstitial" background ($B_{inter}$), "intrastitial" background ($B_{intra}$) exists within the region occupied by an amplified inter, intra, DNA colony. The combination of these two background signals dictates the achievable CNR, and subsequently directly impacts the optical instrument requirements, architecture costs, reagent costs, run-times, cost/genome, and ultimately the accuracy and data quality for cyclic array-based sequencing applications. The $B_{inter}$ background signal arises from a variety of sources; a few examples include auto-fluorescence from consumable flow cells, non-specific adsorption of detection molecules that yield spurious fluorescence signals that may obscure the signal from the ROI, the presence of non-specific DNA amplification products (e.g., those arising from primer dimers). In typical next generation sequencing (NGS) applications, this background signal in the current field-of-view (FOV) is averaged over time and subtracted. The signal arising from individual DNA colonies (i.e., (S)−$B_{inter}$ in the FOV) yields a discernable feature that can be classified. In some instances, the intrastitial background ($B_{intra}$) can contribute a confounding fluorescence signal that is not specific to the target of interest, but is present in the same ROI thus making it far more difficult to average and subtract.

As will be demonstrated in the examples below, the implementation of nucleic acid amplification on the low-binding substrates of the present disclosure may decrease the $B_{inter}$ background signal by reducing non-specific binding, may lead to improvements in specific nucleic acid amplification, and may lead to a decrease in non-specific amplification that can impact the background signal arising from both the interstitial and intrastitial regions. In some instances, the disclosed low-binding support surfaces, optionally used in combination with the disclosed hybridization and/or amplification reaction formulations, may lead to improvements in CNR by a factor of 2, 5, 10, 100, or 1000-fold over those achieved using conventional supports and hybridization, amplification, and/or sequencing protocols. Although described here in the context of using fluorescence imaging as the read-out or detection mode, the same principles apply to the use of the disclosed low-binding supports and nucleic acid hybridization and amplification formulations for other detection modes as well, including both optical and non-optical detection modes.

The disclosed low-binding supports, optionally used in combination with the disclosed hybridization and/or amplification protocols, yield solid-phase reactions that exhibit: (i) negligible non-specific binding of protein and other reaction components (thus minimizing substrate background), (ii) negligible non-specific nucleic acid amplification product, and (iii) provide tunable nucleic acid amplification reactions. Although described herein primarily in the context of nucleic acid hybridization, amplification, and sequencing assays, it will be understood by those of skill in the art that the disclosed low-binding supports may be used in any of a variety of other bioassay formats including, but not limited to, sandwich immunoassays, enzyme-linked immunosorbent assays (ELISAs), etc.

System:

Provided herein are systems for performing base discrimination or base classification reactions using the surface described herein. Also provided is a system for performing one or more steps of any sequencing method disclosed herein. Optionally, the system includes components and reagents necessary to coupling the oligonucleotide molecules, hybridizing sample or target nucleic acids to the attached oligonucleotide molecules, and detecting or imaging the signal on the surface.

Also provided is a system for performing one or more steps of any sequencing method disclosed herein. Optionally, the system includes components and reagents necessary to analyze the sequence of the nucleic acids in such sequencing techniques based on the detection of fluorescent nucleotides or oligonucleotides. The detection instrumentation used to read the fluorescence signals on such arrays may be based on either epifluorescence or total internal reflection microscopy. One detection instrument has been proposed that use an optical sequencing-by-synthesis reader. The reader can include a laser that induces fluorescence from a sample within water channels of a flow cell. The fluorescence is emitted and collected by imaging optics which comprises one or more objective lens and tube lens. Optical imagers include, among other things, a light source to illuminate a sample in the region of interest, one or more detectors, and optical components to direct light from the region of interest to the detector(s). The optical imagers may also include a focus mechanism that maintains focus of the optical components on the region of interest in order that light received at the detectors is received in focus.

Method of Base Pair Classification:

Provided herein are methods of performing nucleic acid base pair discrimination or base pair classification, the method comprising: a) providing a surface; wherein the surface comprises: i) a substrate; ii) at least one hydrophilic polymer coating layer; iii) a plurality of oligonucleotide molecules attached to at least one hydrophilic polymer coating layer; and iv) at least one discrete region of the surface that comprises a plurality of clonally-amplified sample nucleic acid molecules annealed to the plurality of attached oligonucleotide molecules, wherein the plurality of annealed clonally-amplified sample nucleic acid molecules are present with a surface density of at least 10,000 molecules/mm$^2$, b) performing a nucleic acid amplification reaction on sample nucleic acid molecules prior to or after annealing them to the plurality of oligonucleotide molecules; and c) performing a cyclic series of single nucleotide binding or incorporation reactions, wherein the nucleotides are labeled with a detectable tag.

Provided herein also includes method of performing nucleic acid sequencing by utilizing the surfaces or system described herein. In some embodiments, the detectable tag is a fluorophore. In some embodiments, the detectable tag is Cyanine dye-3 (Cy3), and wherein a fluorescence image of the surface acquired using an Olympus IX83 inverted fluorescence microscope equipped with) 20×, 0.75 NA, a 532 nm light source, a bandpass and dichroic mirror filter set optimized for 532 nm long-pass excitation and Cy3 fluorescence emission filter, a Semrock 532 nm dichroic reflector, and a camera (Andor sCMOS, Zyla 4.2) under non-signal saturating conditions while the surface is immersed in a buffer following the binding or incorporation of a first Cy3-labeled nucleotide exhibits a contrast-to-noise (CNR) ratio of at least 20.

In some embodiments, the nucleic acid amplification reaction comprises a bridge amplification reaction. In some embodiments, the nucleic acid amplification reaction comprises an isothermal bridge amplification reaction. In some embodiments, the nucleic acid amplification reaction comprises a rolling circle amplification (RCA) reaction. In some embodiments, the nucleic acid amplification reaction comprises a helicase-dependent amplification reaction. In some embodiments, the nucleic acid amplification reaction comprises a recombinase-dependent amplification reaction. In some embodiments, the at least one hydrophilic polymer coating layer exhibits a water contact angle of less than 50 degrees.

Binding Between Target Nucleic Acid and Multivalent Binding Composition

Some embodiments relate to a method of determining the identity of a nucleotide in a target nucleic acid comprising: (a) providing a composition comprising: (i) a target nucleic acid comprising two or more repeats of an identical sequence; (ii) two or more primer nucleic acids complementary to one or more regions of said target nucleic acid; and (iii) two or more polymerase molecules; (b) contacting said composition with a multivalent binding composition comprising a polymer-nucleotide conjugate under conditions sufficient to allow a binding complex to be formed between said polymer-nucleotide conjugate and the composition of step (a), wherein the polymer-nucleotide conjugate comprises two or more copies of a nucleotide and optionally one or more detectable labels; and (c) detecting said binding complex, thereby establishing the identity of said nucleotide in the target nucleic acid.

In some embodiments, the target nucleic acid is DNA. In some embodiments, the detection of the binding complex is performed in the absence of unbound or solution-borne polymer nucleotide conjugates. In some embodiments, the target nucleic acid has been replicated or amplified or has been produced by replication or amplification. In some embodiments, the detectable label is a fluorescent label. In some embodiments, detecting the complex comprises a fluorescence measurement. In some embodiments, the multivalent binding composition comprises one type of polymer-nucleotide conjugate. In some embodiments, the multivalent binding composition comprises two or more types of polymer-nucleotide conjugates. In some embodiments, each type of the two or more types of polymer-nucleotide conjugates comprises a different type of nucleotide. In some embodiments, the multivalent binding composition consists of three types of polymer-nucleotide conjugates and wherein each type of the three types of polymer-nucleotide conjugates comprises a different type of nucleotide.

In some embodiments, the binding complex further comprises a blocked nucleotide. In some embodiments, the blocked nucleotide is a 3'-O-azidomethyl, 3'-O-methyl nucleotide, or 3'-O-alkyl hydroxylamine. In some embodiments, said contacting occurs in the presence of an ion that stabilizes said binding complex, said complex comprising a polymer nucleotide conjugate, two or more polymerase molecules, and two or more binding sites within the target nucleic acid. In some embodiments, the contacting is done in the presence of strontium, magnesium, calcium ions, or any combination thereof. In some embodiments, the polymerase molecule is catalytically inactive. In some embodiments, the polymerase molecule has been rendered catalytically inactive by mutation or chemical modification. In some embodiments, the polymerase molecule has been rendered catalytically inactive by the absence of a necessary ion or cofactor. In some embodiments, the polymerase molecule is catalytically active. In some embodiments, the binding complex does not comprise a blocked nucleotide. In some embodiments, the binding complex has a persistence time of greater than 2 seconds.

When the multivalent binding composition is used in replacement of single unconjugated or untethered nucleotide to form a complex with the polymerase and the target nucleic acid, the local concentration of the nucleotide is increased many folds, which in turn enhances the signal intensity, particularly the correct signal versus mismatch. The present disclosure contemplates contacting the multivalent binding composition with a polymerase and a primed target nucleic acid to determine the formation of a ternary binding complex.

EXAMPLES

These examples are provided for illustrative purposes only and not to limit the scope of the claims provided herein.

Example 1—Hydrophilic Substrates

Studies were performed to prepare and evaluate low non-specific binding support surfaces using poly(ethylene glycol) (PEG) molecules of different molecular weight and functional end groups. One or more layers of PEG were linked to a glass surface via silane coupling to the functional end groups. Examples of functional groups that may be used for coupling include, but not limited to, biotin, methoxy ether, carboxylate, amine, NHS ester, maleimide, and bis-silane. Oligonucleotide primers with different base sequences and base modifications were then tethered to the surface layer at various densities. Both surface functional group density and oligonucleotide concentration were varied to target certain primer density ranges. Additionally, primer density can be controlled by diluting oligonucleotide with other molecules that carry the same functional group. For example, amine-labeled oligonucleotide can be diluted with amine-labeled polyethylene glycol in a reaction with NHS-ester coated surface to reduce the final primer density. Primers comprising different lengths of a linker positioned between the hybridization region and the surface attachment functional group can also be applied to control density. Example linkers include poly-T and poly-A strands (0 to 20 bases in length) at the 5' end of the primer, PEG linkers (3 to 20 units in length), and hydrocarbon-chain linkers of various lengths (e.g., C6, C12, C18, etc.). To measure the primer density, fluorescence-labeled primers were immobilized to the surface and the fluorescence reading was compared with that for a dye solution of known concentration.

Low non-specific binding (also referred to herein as "passivated") substrate surfaces are desirable so that biomolecules, such as protein and nucleic acids, do not "stick" to the surfaces. Examples of low non-specific binding (low NSB) surfaces prepared using standard monolayer surface preparations and various glass surface treatments are provided below. Performing nucleic acid amplification successfully on passivated surfaces creates a unique challenge. Since passivated, hydrophilic surfaces exhibit ultra-low NSB of proteins and nucleic acids, novel conditions must be utilized to achieve high passivation, improved primer deposition reaction efficiencies, hybridization conditions, and induce effective nucleic acid amplification. Solid-phase nucleic acid hybridization and amplification processes require nucleic acid template attachment to the low binding or passivated surface, and subsequent protein delivery and binding to the surface. A combination of a new primer surface conjugation formulation (identified through Cy3 oligonucleotide graft titration) and the resulting ultra-low non-specific background (as evaluated using NSB functional test results for red and green dyes) demonstrate the viability of these approaches.

Figure 9:
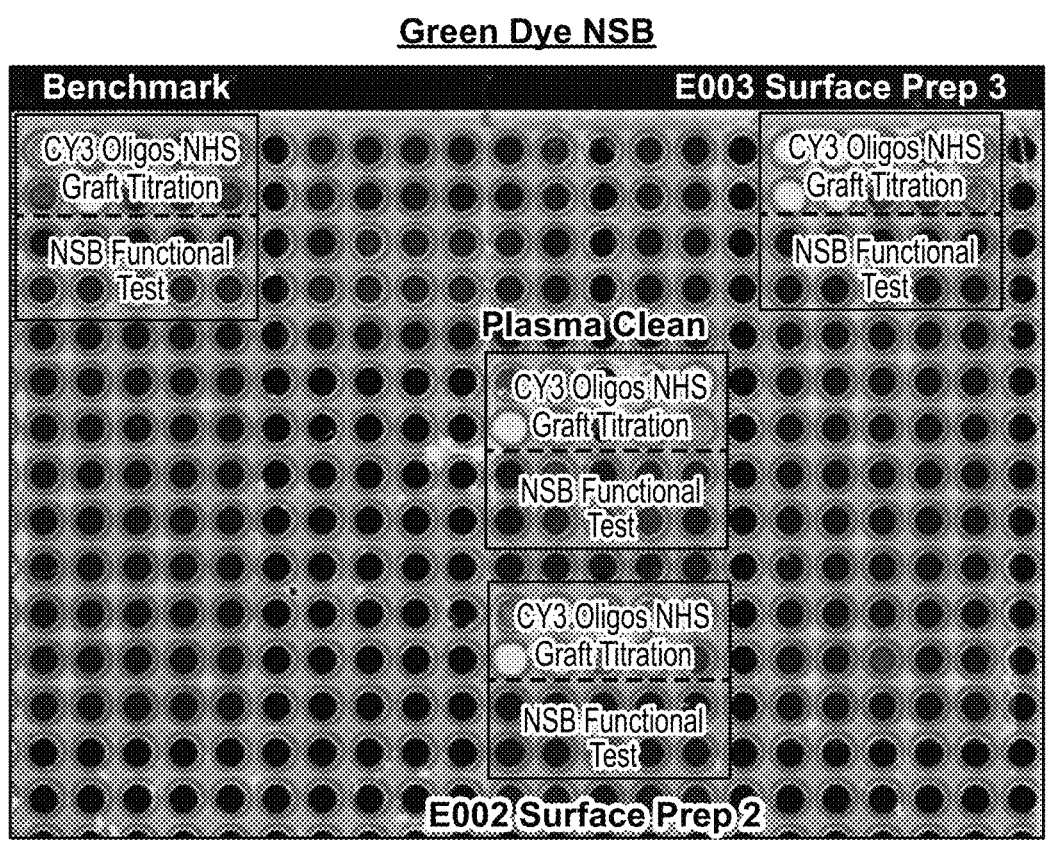
FIG. 9 provides an example of image data from a study to determine the relative levels of non-specific binding of a green fluorescent dye to glass substrate surfaces treated according to different surface modification protocols.
Figure 10:
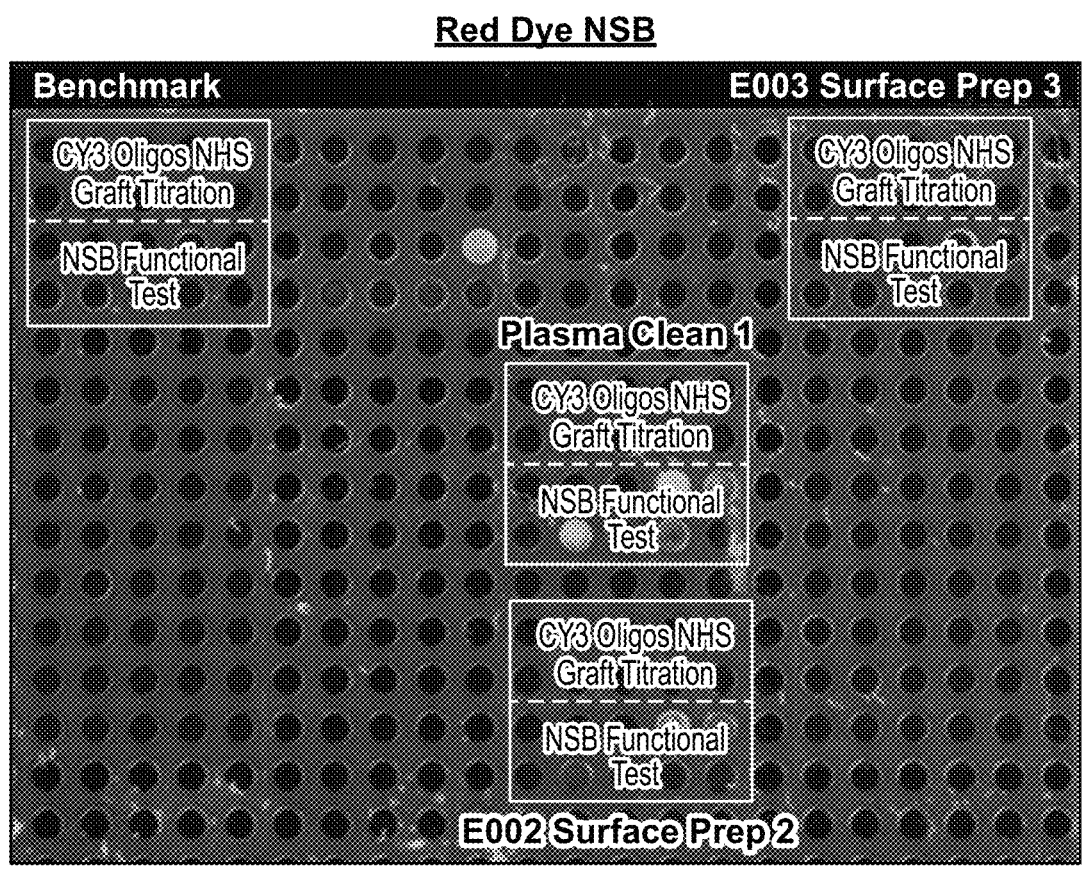
FIG. 10 provides an example of image data from a study to determine the relative levels of non-specific binding of a red fluorescent dye to glass substrate surfaces treated according to different surface modification protocols.
Figure 11:
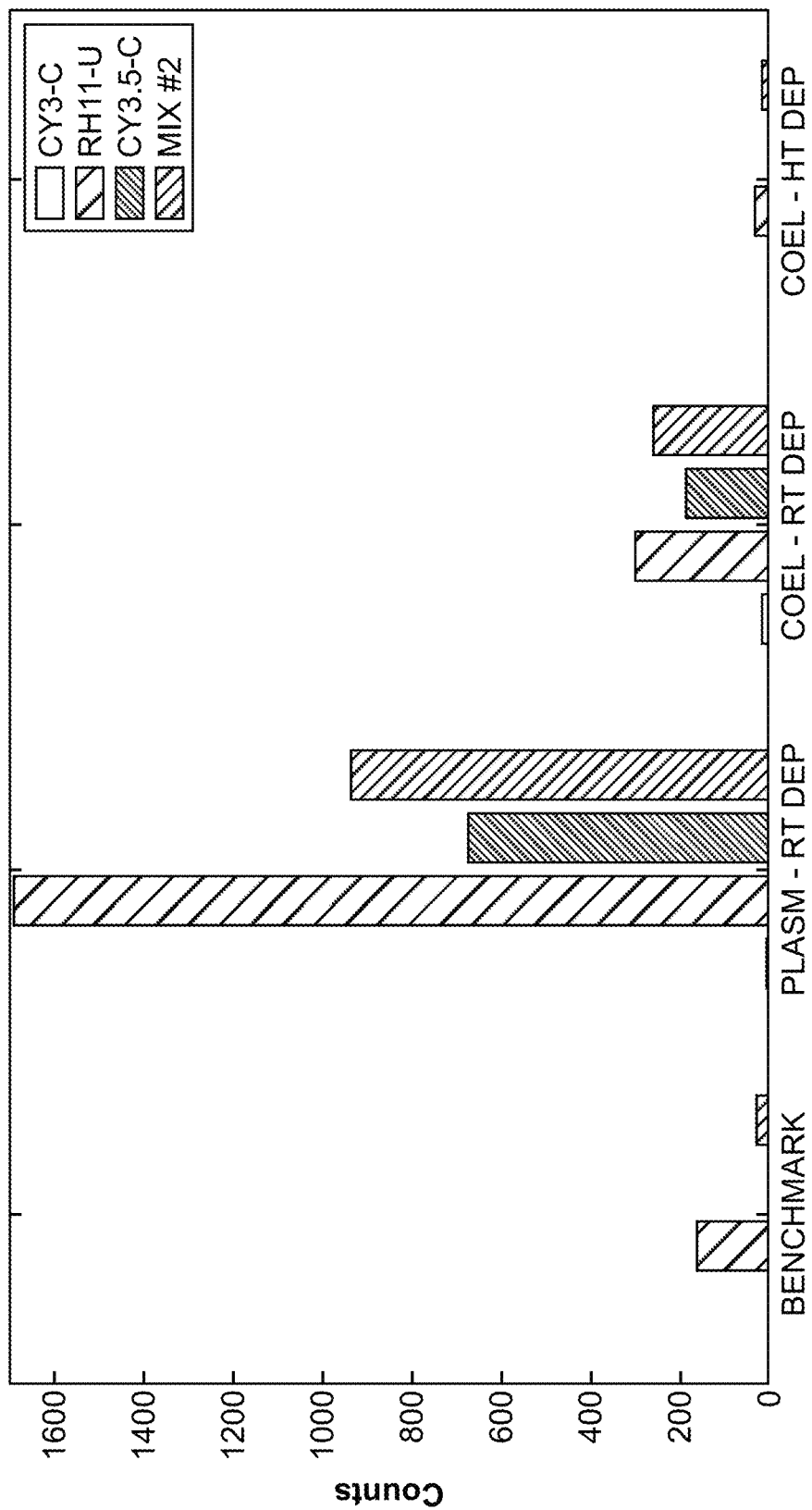
FIG. 11 provides an example of oligonucleotide primer grafting data for substrate surfaces treated according to different surface modification protocols.
Figure 14:
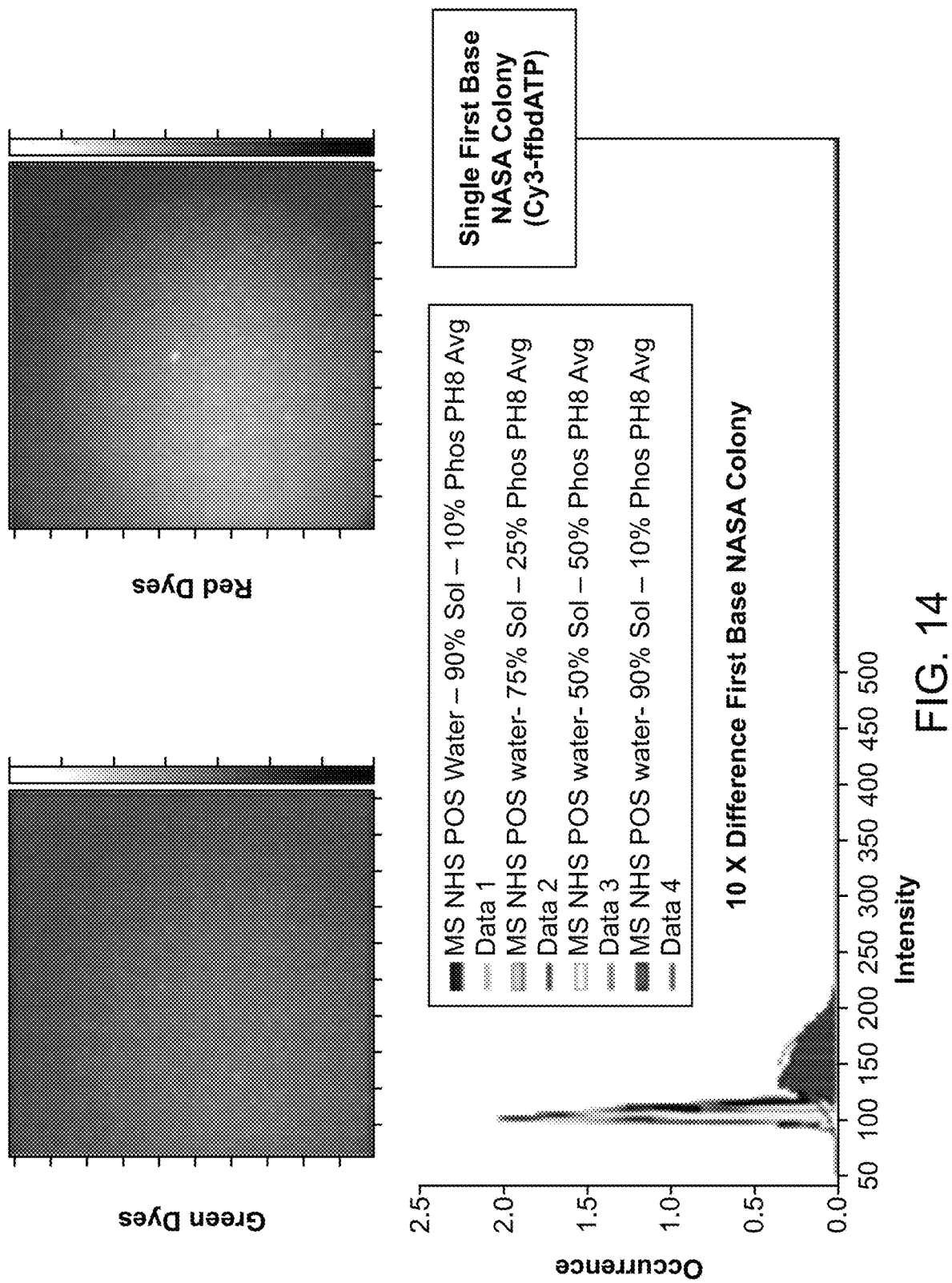
FIG. 14 provides an example of images and data for non-specific binding of green and red fluorescent dyes to substrate surfaces treated according to different surface modification protocols. For comparison purposes, the fluorescence intensity of a clonally-amplified template colony measured under the same set of experimental conditions after coupling a single Cy3-labeled nucleotide base is about 1,500 counts.
Figure 15:
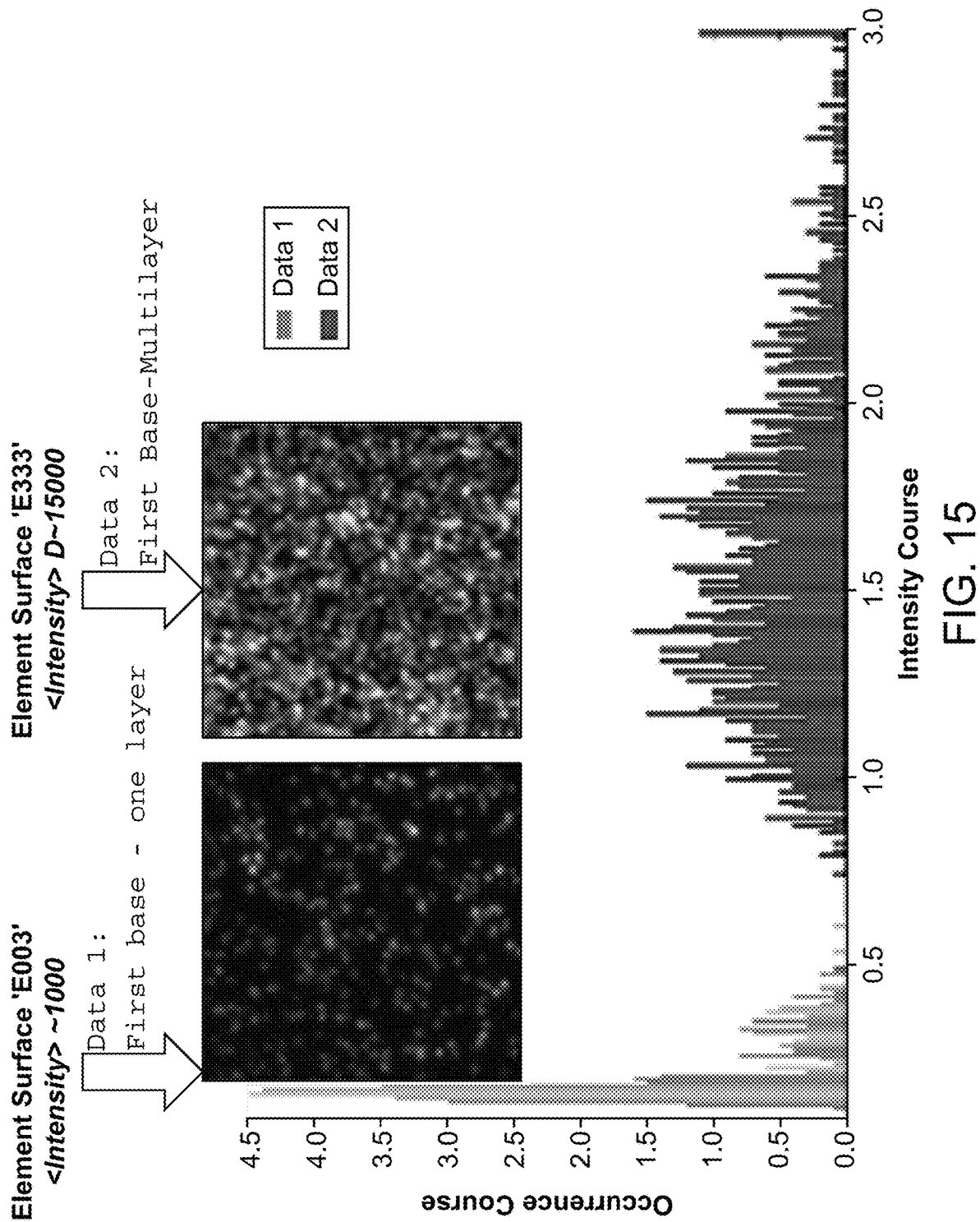
FIG. 15 provides an example of images and data demonstrating "tunable" nucleic acid amplification on a low binding solid support by varying the oligonucleotide primer density on the substrate. Blue histogram: low primer density. Red histogram: high primer density. The combination of low non-specific binding and tunable nucleic acid amplification efficiency through adjustment of oligonucleotide primer density yields high CNRs and subsequent improvements in nucleic acid sequencing performance.

In order to scale primer density and add additional dimensionality to hydrophilic or amphoteric surfaces, multi-layer coatings have been applied and tested using PEG and other hydrophilic polymers. By using hydrophilic and amphoteric surface layering approaches that include, but are not limited to, the polymer/co-polymer materials described here, it is possible to increase primer loading on the support surface significantly. Conventional PEG coated supports that use a monolayer primer deposition process have been reported for single molecule sequencing applications, but they do not yield high copy numbers for nucleic acid amplification. Here, we disclose that "layering" can be accomplished using traditional crosslinking approaches and chemistry-compatible monomer or polymer subunits such that one or more highly-crosslinked layers can be built sequentially. Non-limiting examples of polymers that are suitable for use include of streptavidin, poly acrilamide, polyester, dextram, poly-lysine, polyethylene glycol, and poly-lysine copolymers poly acrylamide, poly (N-isopropylacrylamide) (PNI-PAM), poly(2-hydroxyethyl methacrylate), (PHEMA), poly (oligo(ethylene glycol) methyl ether methacrylate (POEGMA), polyester, dextran, poly-lysine, polyethylene glycol (PEG), polyacrylic acid (PAA), poly(vinylpyridine), poly(vinylimidazole) and poly-lysine copolymers. The different layers may be attached to each other using any of a variety of covalent or non-covalent reactions including, but not limited to, biotin-streptavidin binding, azide-alkyne click reactions, amine-NHS ester reactions, thiol-maleimide reactions, and ionic interactions between positively charged polymers and negatively charged polymers. It is also conceivable that these high primer density materials can be constructed in solution and subsequently layered onto the surface in multiple steps. With this approach, it is possible to generate low NSB/low background substrate surfaces (FIGS. 9-13) for performing solid-phase nucleic acid amplification and sequencing chemistries that provide significantly improved nucleic acid amplification, such that the signal-to-background ratios can be tuned to meet the needs of a specific sequencing application (FIG. 14 and FIG. 15). FIG. 9 provides an example of image data from a study to determine the relative levels of non-specific binding of a green fluorescent dye to glass substrate surfaces treated according to different surface modification protocols. FIG. 10 provides an example of image data from a study to determine the relative levels of non-specific binding of a red fluorescent dye to glass substrate surfaces treated according to different surface modification protocols. FIG. 11 provides an example of oligonucleotide primer grafting data for substrate surfaces treated according to different surface modification protocols.

Method for Preparing a 2-Layer PEG Surface with Thiol-Maleimide Chemistry:

A glass slide was cleaned using a 2M KOH treatment of 30 minutes at room temperature, washed, and then surface silanol groups were activated using an oxygen plasma. Silane-PEG5K-Thiol (Creative PEGWorks, Inc., Durham, N.C.) was applied at a concentration of 0.1% in ethanol. After a 2-hour coating reaction, the slide was washed thoroughly with ethanol and water, and then reacted with 2.5 mM of Maleimide-PEG-Succinimidyl Valerate (MW=20K) in dimethylformamide (DMF) for 30 minutes. The resulting surface was washed and promptly reacted with 5'-amine-labeled oligonucleotide primer at room temperature for 2 hours. Excess succinimidyl esters on the surface were deactivated by reacting with 100 mM glycine at pH9 following the primer immobilization.

Method for Preparing a Multi-Layer PEG Surface with NHS Ester-Amine Chemistry:

A glass slide is cleaned by 2M KOH treatment of 30 minutes at room temperature, washed, and then surface silanol groups are activated using an oxygen plasma. Silane-PEG2K-amine (Nanocs, Inc., New York, N.Y.) is applied at a concentration of 0.5% in ethanol solution. After a 2-hour coating reaction, the slide was washed thoroughly with ethanol and water. 100 uM of 8-arm PEG NHS (MW=10K, Creative PEGWorks, Inc., Durham, N.C.) was introduced at room temperature for 20 minute in a solvent composition that can include 5, 10, 20, 30, 40, 50, 60, 70, 80 or 90 percent organic solvent and 5, 10, 20, 30, 40, 50, 60, 70, 80 or 90 percent low ionic strength buffer. The resulting surface was washed and reacted with 20 μM multi-arm PEG amine (MW=10K, Creative PEGWorks, Inc., Durham, N.C.) for 2 hours. The resulting amine-PEG surface was then reacted with a mixture of multi-arm PEG-NHS and amine-labeled oligonucleotide primer at varying concentrations. This process can be repeated to generate additional PEG layers on the surface.

Figure 16:
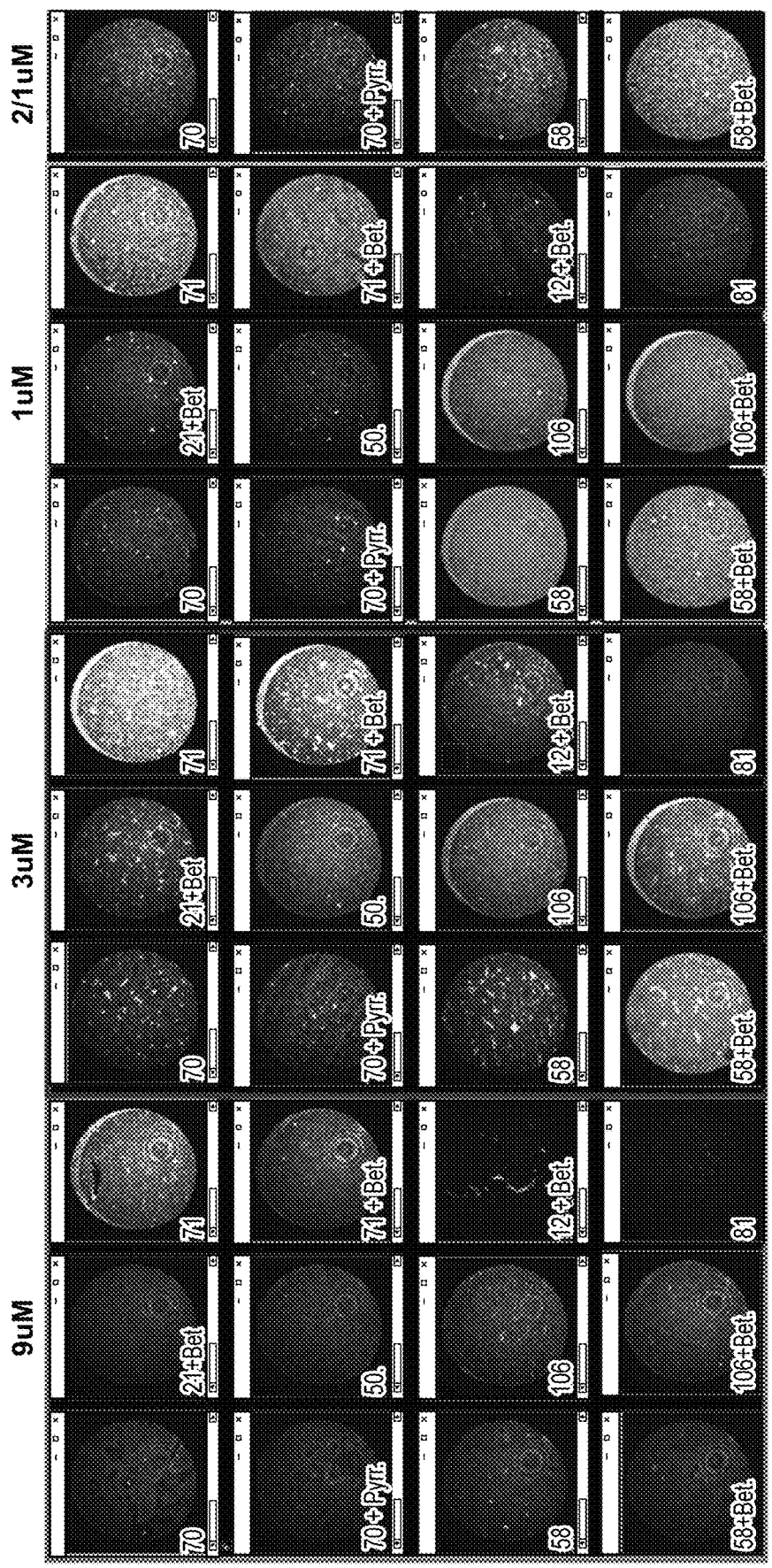
FIG. 16 provides examples of fluorescence images of the low binding solid supports of the present disclosure on which tethered oligonucleotides have been amplified using different primer densities, isothermal amplification methods, and amplification buffer additives.

Solid-Phase Isothermal Amplification:

In considering various isothermal amplification methods, it can be shown that each isothermal amplification method has a unique optimum primer density range, which requires tunable surface coatings to maximize the amplification efficiency. In some cases higher primer surface density scales with larger template copy numbers (FIG. 15). In some cases, although higher surface densities of primers may yield high foreground signals (i.e., sequence-specific signals) for some amplification approaches, they may lead to high background signals and thus prove detrimental for other amplification approaches. In FIG. 16, primer deposition concentrations are shown at the top of the figure, while the various helicase isothermal amplification formulations tested are indicated in the images acquired of the resulting surface following the isothermal amplification reaction. The image for each surface was expected to appear red if specific amplification had occurred. As is evident from the series of images for formulation "58" in FIG. 16, as the primer density was increased the color fades from red to green, thus indicating a reduction in specific amplification. In addition, it can be seen that including Betaine (a common buffer additive) in the amplification reaction formulation decreases the degree of nonspecific amplification in favor of specific amplification, thereby resulting in brighter signals and improved CNR. The combination of low-binding, layered support surfaces, tunable surface densities of primers, improvements in hybridization and/or amplification reaction formulations (including adjustments in buffer components and additives (e.g., choice of buffer, pH, solvent, ionic strength, detergents, formamide, betaine, crowding agents and other additives, etc.), and resulting improvements in amplification rates and specificity should lead to unprecedented improvements in next-generation sequencing of nucleic acids.

The present disclosure addresses the challenges of achieving highly monoclonal amplification of library nucleic acid strands on hydrophilic substrates for a variety of applications that require signal enhancement, such as nucleic acid detection, sequencing, and diagnostics applications. Conventional isothermal methods for nucleic acid amplification for generating monoclonal clusters of a library nucleic acid strand are limited and have flaws. Examples of their performance limitations include long clustering times (e.g., 2+ hours), the requirement for high temperature (e.g., 60 C or above), the inability to amplify/cluster efficiently on certain surfaces, high cost, polyclonality issues, reagent stability issues, etc. Despite the wealth of isothermal amplification methods described in the literature, there are only one or two methods which have been successfully applied to commercial sequencing applications. Here, we propose isothermal amplification strategies that successfully generate clusters of monoclonal copies of a library DNA fragment (or other nucleic acid) for applications such as DNA sequencing and eliminate or alleviate the aforementioned problems.

The design criteria for developing ensemble DNA amplification/DNA sequencing composition changes to decrease background signals ($B_{inter}$ and $B_{intra}$) and facilitate controlled DNA amplification on low binding substrates included: (i) decreased nonspecific DNA amplification (e.g., due to amplification of primer dimers) in interstitial regions ($B_{inter}$) as compared to traditional/prior art approaches, (ii) decreased amounts of non-specific DNA amplification product (e.g., primer dimers) within specific DNA colonies ($B_{intra}$) as compared to traditional/prior art approaches, (iii) increased control of specific DNA amplification (e.g., reaction times, cycle times, primer surface density titration, primer surface density, primer sequence, etc.) on low binding substrates, such that signal-to-background (S/B) ratio is reduced even in the absence of hybridization and amplification formulation improvements.

Example 2—Helicase-Dependent Amplification on Low Binding Surfaces with Improved Specificity It is well known that helicase-dependent amplification is highly prone to non-specific amplification, such as primer dimer formation. We may reduce this non-specific amplification on the surface through any combination of following methods: (i) designing oligonucleotide primers that produces less primer dimer, (ii) adjust primer surface density on the multilayered support surface, (iii) performing the reaction at higher temperatures using thermophilic enzymes, (iv) using amplification buffer additives such as those mentioned above and non-self-priming primer sequences in combination, and (v) introducing one or more full nucleic acid denaturation and primer hybridization steps.

Specific Helicase-Dependent Amplification on Low NSB Surfaces in the Absence of SSB Protein:

Helicase-dependent amplification of linear template strands can be achieved with reduced non-specific amplification and highly-efficient clonal amplification on low binding surfaces. A forward primer on the surface gets extended on a single-stranded template library strand using a polymerase and helicase-containing amplification reaction mixture. Then, optionally, the template strand is denatured and washed away. Alternatively, the duplex may be unwound by the helicase activity. Either method leaves the forward strand extended from the surface conjugated primer, partially or fully in single-stranded form. Subsequently, a surface-tethered reverse primer hybridizes to this forward strand and is also extended, thereby creating a double-stranded bridge structure. The helicase present in the reaction mixture unwinds the intermediate double-stranded amplicon strands which are then available to re-hybridize to other free surface-tethered primers for subsequent amplification rounds. For this to happen, the degree of unwinding doesn't need to be extensive—just sufficient to convert primer hybridization regions into single stranded components (end fraying) to allow hybridization of subsequent surface-conjugated primers. The helicase used in this reaction should be capable of initiating unwinding from the ends of the bridge structure, and may be either a 3' to 5' helicase or a 5' to 3' helicase. In some cases, it may be a superfamily 1, 2, 3 4, 5 or 6 helicase. In some cases, it may be a highly processive helicase (i.e., able to unwind many consecutive base pairs without releasing the single-stranded or double-stranded structure) or a helicase with limited processivity. Certain mutants of superfamily 1 helicases that exhibit higher processivity, such as the UvrD303 mutant of helicase UvrD, may be used in this amplification scheme.

In order to facilitate unwinding by 5' to 3' helicases, all or a portion of one or both surface-tethered primers may include modifications to create specific loading sites for the 5' to 3' helicase. On a template nucleic acid extended from such a primer, the modification site would act as a polymerase stop point thereby leaving the stretch of primer sequence between the surface conjugation point and the modification site always in single-stranded form. This stretch would act as loading site for helicases with 5' to 3' directionality, as many helicases have much better single stranded nucleic acid binding affinity, directing and enhancing the 5' to 3' helicase unwinding activity where it is needed for helicase-dependent amplification on the support surface. Examples of primer modifications that may be used include, but are not limited to, an insertion of a PEG chain into the backbone of the primer between two nucleotides towards the 5' end, insertion of an abasic nucleotide (i.e., a nucleotide that has neither a purine nor a pyrimidine base), or a lesion site which can be bypassed by the helicase.

Many helicases have co-factor proteins and specific conformations that activate or enhance the helicase activity. Examples include, but are not limited to, the RepD protein for the PcrA helicase from Bst, the phi X gene protein A for the *E. coli* Rep helicase, and the MutL protein for the UvrD helicase. Addition of these accessory proteins may enable the desired unwinding activity more effectively and thus further facilitate helicase-dependent isothermal amplification. Some of these co-factors have specific binding sequences or moieties which may be added to the primers to direct the unwinding activity.

Helicase amplification formulations showed diminished non-specific amplification when using a mesophilic helicase and a strand displacing polymerase formulation that lacked single stranded binding (SSB) protein (e.g., internal reference formulation #58). Unlike the case for most helicase-dependent amplification approaches, the exclusion of single stranded binding protein (which typically is used to disrupt transient non-specific hybridization) from the formulation was observed to reduce non-specific amplification. A variety of formulation changes were shown to mitigate the increase in non-specific hybridization on low binding surfaces.

Figure 17:
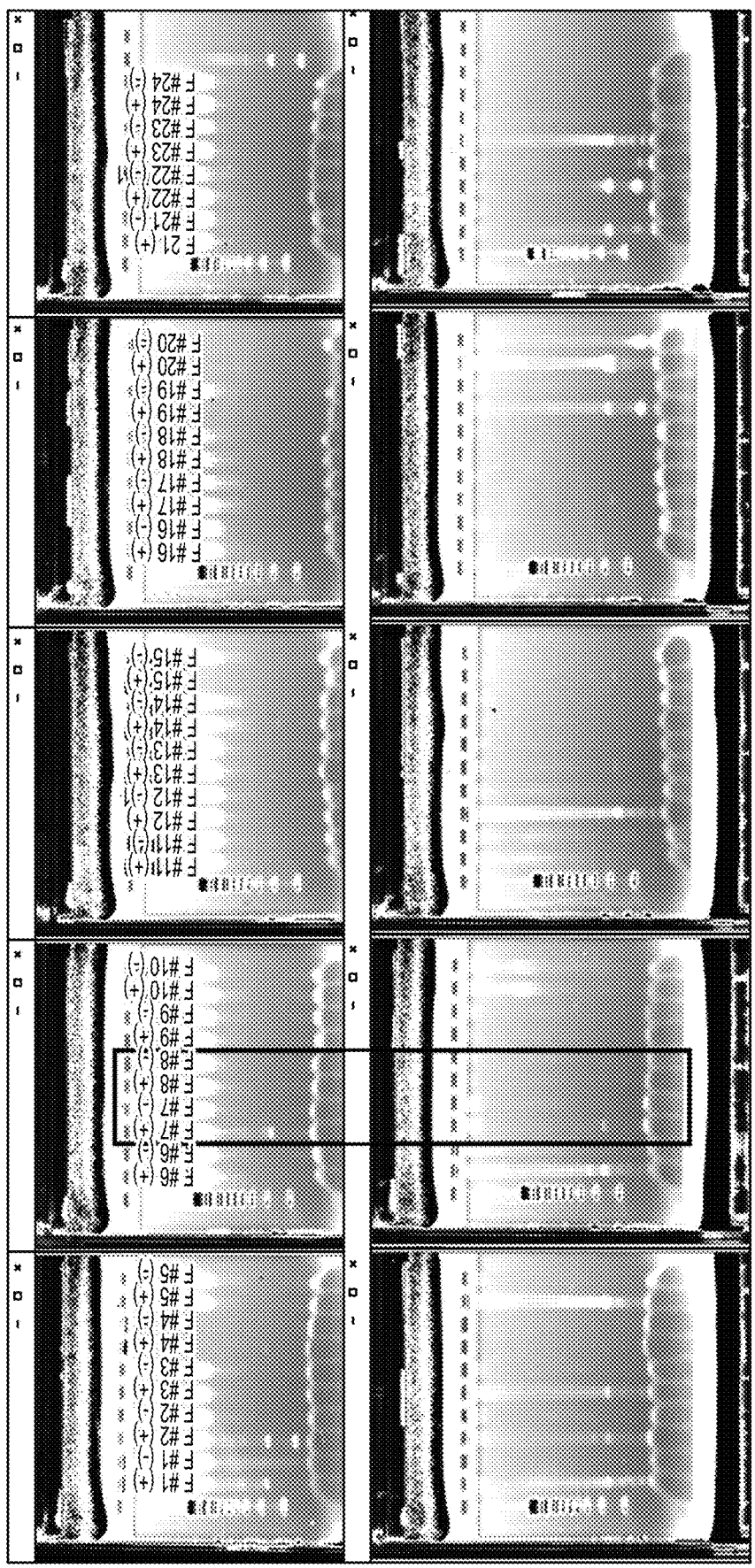
FIG. 17 provides examples of gel images that demonstrate reduction of non-specific nucleic acid amplification through the use of amplification buffer additives while maintaining specific amplification of the target sequence. The gel images reveal a band corresponding to specific amplification of the target (arrow) and other gel quantified amplification products.
Figure 18:
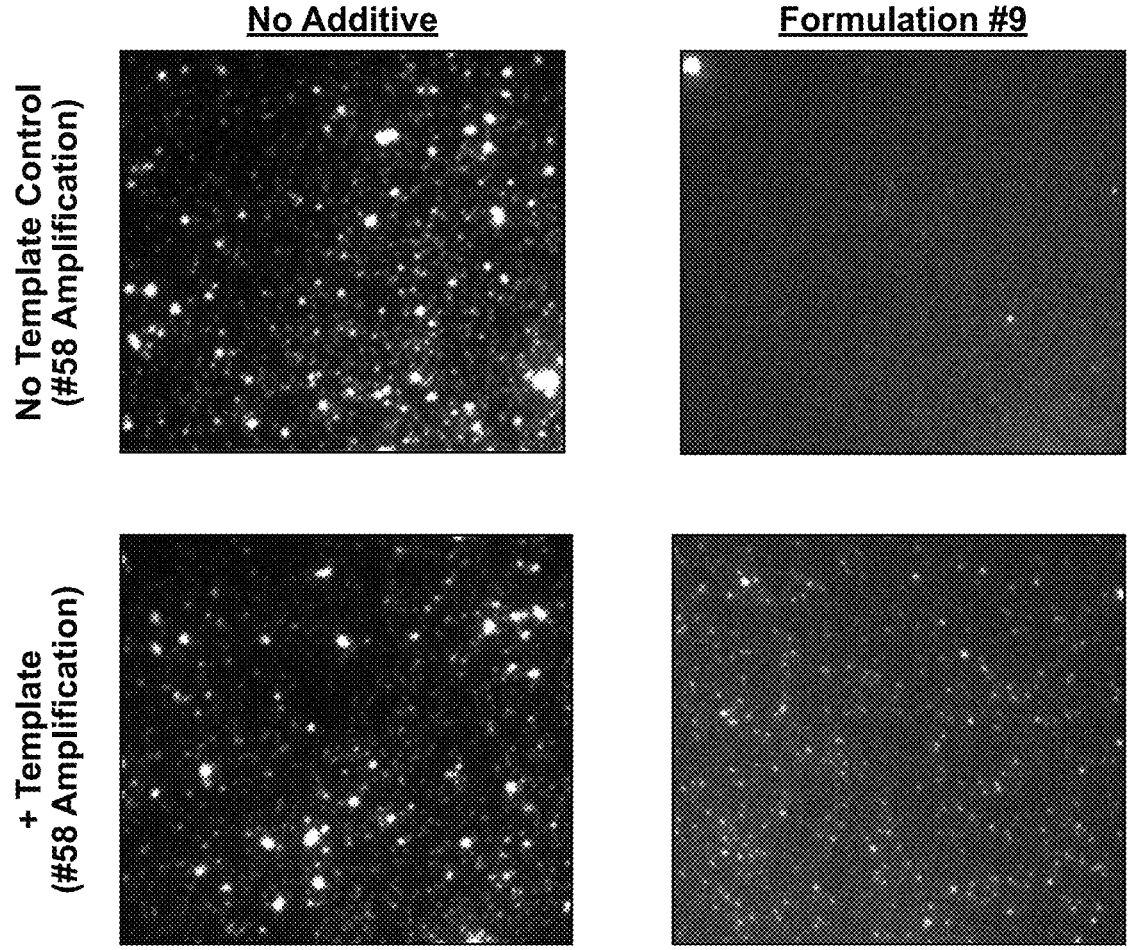
FIG. 18 provides examples of fluorescent images that demonstrate the impact of formulation changes to improve amplification specificity on a low binding support surface.

Formulation Composition Change for Improved Helicase-Dependent Amplification:

Additives such as Betaine are commonly known to decrease the non-specific amplification for isothermal amplification reactions performed in solution. The criteria become more restrictive as high primer surface densities are required to support tunable amplification and high copy number in template nucleic acid colonies. At high primer density, non-specific amplification begins to abet the benefits of high template copy number in the resulting colonies (FIG. 16). As a result, additional additive formulations have been discovered which abet the non-specific amplification within a template nucleic acid colony. In the example shown in FIG. 16, it can be clearly seen that the addition of Betaine to formulation #58 creates more specific amplification (indicated by the red color) on higher primer density surfaces. In addition to betaine, it is possible to combine many different reaction formulation components to achieve higher amplification specificity in solution and on a low binding surface (FIG. 17 and FIG. 18).

Organic solvents such as acetonitrile, DMSO, DMF, ethanol, methanol and similar compounds alter the structure of single stranded and double stranded nucleic acids through a process of oligonucleotide dehydration. Compounds such as 2-pyrrolidone and formamide are known to reduce the melting temperature of nucleic acids, and reduce secondary structure from high GC content oligonucleotides. Crowding agents are also known to stabilize nucleic acid structure. In low pH buffers, hybridization and hydrogen bonding in base pairing become more favorable. When combining the different attributes of each of these respective formulations, it is possible to increase specific annealing of oligonucleotide sequences by more than 2 orders-of-magnitude over traditional approaches. By combining these compounds and adding them to the amplification formulations described below, non-specific amplification, such as arising from primer dimers, is drastically abated, and good yields of specific amplification product are still observed in solution (FIG. 17) and on the disclosed low NSB surfaces (FIG. 18).

Example 3—Modified Rolling Circle Multiple Displacement Amplification (Modified RCA-MDA)

Nucleic acid library fragments are ligated to adapter sequences (that contain forward, reverse, and sequencing primers, and any identification/barcode sequences) and circularized either in the solution, or on the low binding surface.

Circularized ssDNA is then captured by or hybridized to a forward surface primer either in solution or on the surface and extended in a RCA reaction by a strand displacing polymerase which makes single-stranded concatemeric copies of the library nucleic acid and adapter sequences. Reverse primers hybridize to this concatemeric forward template at multiple positions and are extended by the RCA reaction mix, thereby making concatemeric reverse copies. During this process reverse strands are displaced by each other. An upstream reverse strand extension would displace the downstream extension, thus creating single-stranded concatemeric reverse strands. The addition of helicases can generate single-stranded regions of nucleic acid that last long enough to restart the hybridization and trigger displacement cascades, which can increase the amplification copy number in a relatively controlled fashion. Alternatively, the addition of recombinases and accessory proteins can hybridize primers into the homologous regions of duplexed DNA in a process called strand invasion. This will restart displacement and hybridization cascades, and increases the copy number in the colony.

Copy number in the RCA-MDA colonies is determined by the primer surface density, which dictates how frequently and successfully the initial concatemers or displaced concatemers are hybridized with the forward and the reverse primers. Increased primer density on low binding surfaces has proven to generate higher amplification copy numbers in these clusters (FIG. 15). In summary, it is possible to increase the copy number or specific amplification, and decrease the non-specific amplification on low binding surfaces, using one or a combination of the following methods: (i) specific copy number may be increased by increasing the efficiency of primer template hybridizations through formulation changes (FIG. 16), (ii) specific copy number may be increased by increasing the primer density on low binding substrates (FIG. 14 and FIG. 15), (iii) non-specific amplification of primer dimers or chimeric DNA generation may be decreased by using the additives described above, (iv) amplification incubation temperatures may be increased using thermostable enzymes combined with formulation changes as previously described to reduce the non-specific amplification, (v) primer compositions that comprise non-self-hybridizing primer sequences may be used in combination with additives and/or increased amplification incubation temperatures to decrease non-specific primer dimer amplification.

Example 4—Single-Stranded DNA Binding (SSB) Protein Mediated Isothermal Amplification SSB proteins can resolve secondary structures in nucleic acid strands, stabilize the single-stranded DNA after unwinding, prevent or disrupt transient non-extensive hybridization of two nucleic acid strands (a precursor to primer dimer amplification), facilitate specific hybridization of short oligonucleotides to the correct complementary regions in a target oligonucleotide, and interact and direct enzymes to the forked junctions of single-stranded and double-stranded nucleic acids. C-terminal truncation mutations in SSB were reported to remove the cooperative binding to ssDNA while its monomers exhibit stronger binding to ssDNA and reduce the melting temperature of dsDNA. For example, a C-terminal truncation mutation of a phage SSB protein, T4 gp32, yields a protein (gp32ΔC) that reduces the melting temperature of dsDNA by tens of degrees compared to the performance of the wild type protein.

In this amplification scheme, we use these proteins in a formulation that comprises both truncated and wild type SSB proteins (and strand displacing polymerase) to transiently melt the ends of the double-stranded nucleic acid bridge intermediates and allow surface primer hybridization and primer extension. Even though SSB slows down nucleic acid hybridization, it is known to facilitate specific hybridization in general. Hence, the use of truncated SSB proteins such as T4 gp32ΔC, for example, could enable more efficient hybridization of the 3' ends in the bridged nucleic acid structures to other free surface-tethered primers. While this would also disrupt the freshly formed primer template complexes, an optimized formulation should allow extension of such complexes by a strand displacing polymerase. SSB proteins are found in a variety of phages (for example, T4 gp32), bacteria, archaea, fungi, and eukaryotic organisms. Some are thermostable SSB proteins, of which the C-terminal truncated forms could enable more efficient nucleic acid end melting at optimized higher temperatures, thus enable SSB-dependent thermophilic amplification while taking advantage of lower non-specific amplification at higher temperature.

Through the use of additives such as those mentioned above, primer sequence design and specific hybridization and/or amplification formulations, and optimized temperatures for use with appropriate temperature- and chemically-resistant enzymes and proteins, this amplification method can be tailored to drive highly-specific amplification, while eliminating non-specific amplification.

This scheme can be used to amplify circular DNA as well as linear DNA, where each initiation of extension by a strand displacing polymerase can lead to multiple subsequent multiple displacement amplification events that yield concatemeric copies of the circular DNA template (see the section on modified RCA-MDA above).

We have found that SSB-mediated amplification (using, for example, phi29 SSB) of circular library DNA is much faster than traditional RCA (e.g., requiring amplification times of only 30 min to 1 hour vs 2 to 3 hours for traditional RCA). Products of SSB-mediated amplification performed in solution ran as discrete concatemeric ladders on gels.

Example 5—Low-Temperature Thermal Cycling Bridge Amplification on Low Binding Surfaces By using combinations of additives for improved hybridization and/or amplification formulations, thermostable SSB proteins, and/or truncated SSB proteins, PCR formulations have been developed that can be thermally cycled at lower temperatures than the traditional methods outlined in Mullis' original PCR disclosure. In this scheme, it is possible to use additives to drive nucleic acid hybridization and de-hybridization temperatures below their traditional values. For example, formamide is commonly used to reduce the melt temperature ($T_m$) of DNA and subsequent DNA de-hybridization can be performed at a temperature of around 60 degrees. On the other hand, re-annealing temperatures typically also require temperature ramps from high temperatures (95 degrees C.) to close to room temperature. It is possible to create formulations such that the re-annealing temperature stringencies can be drastically reduced. Using such a formulation would constitute a significant improvement over traditional bridge amplification methods, such that temperature ramps can be performed between 20 and 60 degrees. Decreases in temperature ramp requirements and improved hybridization stringency on low binding substrates could yield the following advantages over traditional bridge amplification: (i) decreased amplification times; (ii) simplified instrumentation design, (iii) decreased reagent usage through faster and more specific hybridization resulting in more efficient amplification rates, and (iv) reduced reagent costs. It is also possible to show that the stringency of the improved hybridization would decrease the number of amplification cycles required for amplification on the support surface.

Figure 19A:
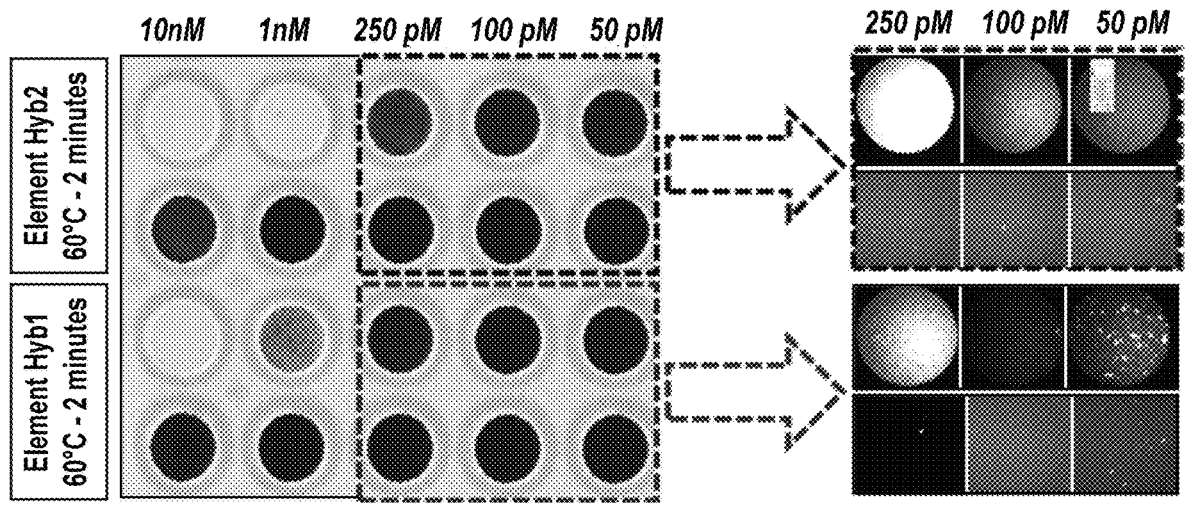
FIGS. 19A-B provide non-limiting examples of image data that demonstrate the improvements in hybridization stringency, speed, and efficacy that may be achieved through the reformulation of the hybridization buffer used for solid-phase nucleic acid amplification, as described herein.
Figure 19B:
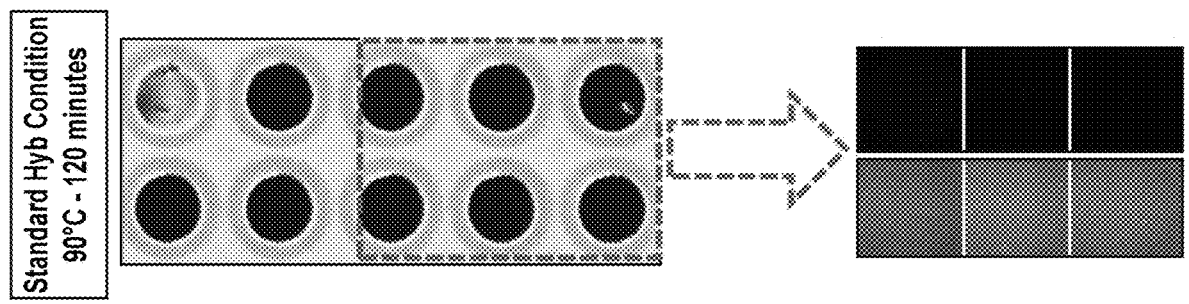

FIGS. 19A-B provide examples of data that illustrate the improvements in hybridization efficiency that may be obtained using the low non-specific binding supports and improved hybridization formulations of the present disclosure (FIG. 19A) as compared to those for a conventional hybridization formulation (FIG. 19B).

Figure 20:
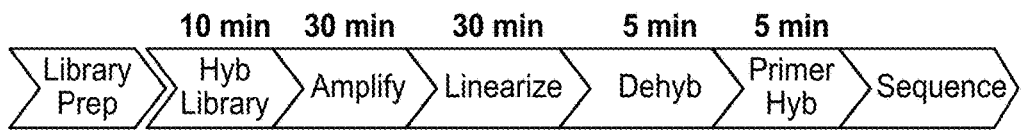
FIG. 20 illustrates a workflow for nucleic acid sequencing using the disclosed low binding supports and amplification reaction formulations of the present disclosure, and non-limiting examples of the processing times that may be achieved.

FIG. 20 illustrates a workflow for nucleic acid sequencing using the disclosed low binding supports and hybridization/amplification reaction formulations of the present disclosure, and non-limiting examples of the processing times that may be achieved thereby.

Example 6—Preparation of 2-Layer PEG Surface with Thiol-Maleimide Chemistry

A glass slide is chemically treated to remove organics and activate hydroxyl groups for silane coupling (various methods include plasma treatment, piranha etching, base wash, base baths, high temperature glass annealing and any combination thereof. Silane-PEGSK-Thiol (Creative PEG-Works, Inc) is applied at concentration of 0.1% in Ethanol solution. After 2-hour of coating reaction, the slide is washed thoroughly with Ethanol and water and then reacted with 2.5 mM of Maleimide-PEG-Succinimidyl Valerate (MW 20K) in DMF for 30 minutes. The resulted surface is washed and promptly reacted with 5'-amine-labeled oligonucleotide primer at room temperature for 2 hours. The excess succinimidyl esters on surface are deactivated with 100 mM of glycine at PH9 after the primer immobilization. This approach confers negligible low binding solid support surfaces through and efficient primer and polymer iterative coupling that exceeds traditional methodologies for by almost 2 orders of magnitude.

Example 7—Preparation of Multi-Layer PEG Surface with NHS Ester-Amine Chemistry

A glass slide is chemically treated to remove organics and activate hydroxyl groups for silane coupling (various methods include plasma treatment, piranha etching, base wash, base baths, high temperature glass annealing and any combination thereof. Silane-PEG-amine (Nanocs, Inc) is applied at concentration of 0.1%-2% in clean Ethanol solution. After 2-hour of coating reaction, the slide is washed thoroughly with Ethanol and water. Multi-arm PEG NHS is introduced at room temperature for 5-30 minute in a solvent composition that can include 5, 10, 20, 30, 40, 50, 60, 70, 80 or 90 percent organic solvent and 5, 10, 20, 30, 40, 50, 60, 70, 80 or 90 percent low ionic strength buffer. The resulted surface is washed and reacted with multi-arm PEG amine (MW 10k, Creative PEGWorks, Inc). The resulted amine-PEG surface is then reacted with a mixture of multi-arm PEG NHS and amine-labeled oligonucleotide primer at varying concentrations. This process can be repeated to generate additional PEG layers on surface. This approach confers negligible low binding solid support surfaces through and efficient primer and polymer iterative coupling that exceeds traditional methodologies for by almost 2 orders of magnitude.

Example 8—Calculation of CNR on Cluster Data

Typically, when fluorescence detection is used for solid-phase assays, signals are generated by tethering and/or amplifying molecules, coupled with or followed by attachment of reporter dye molecules. This process produces both specific and non-specific signals. The non-specific components are commonly referred to as non-specific noise or background (arising from either inter- or intra-stitial contributions) which interferes with the measurement of the specific signal and reduces contrast-to-noise ratio (CNR).

Non-specific background can be generated either from dye molecules adsorbed non-specifically to the support surface, or from non-specific amplification of, for example, primer-dimer pairing on the surface. Both mechanisms produce substantial fluorescence background when fluorescent reporters are used to label the specific molecules of interest.

The disclosed low-binding support surfaces and associated methods for use demonstrate significant improvement in minimizing the non-specific background. As shown in the examples described below, estimated non-specific background is well below 10% of the total signal using the specified amplification method and support surface. On the other hand, conventional amplification methods and support surfaces often produce background signals that are 30% to 50% of the total signal.

Note that, as used herein, the non-specific background or noise is only one component of the total system noise, which may also include other contributions from the detection system, such as photon shot noise, auto-fluorescence background, image sensor noise, illumination noise (e.g., arising from fluctuations in illumination intensity), etc. In this regard, it may be possible to extend the disclosed approaches for CNR improvement through novel support surfaces and associated hybridization and amplification methods to achieve even larger improvements for NGS and other bioassay technologies by, for example, correcting for signal impurities that may arise from traditional sequencing-by-synthesis, such as through the use of pre phasing and phasing, and also correcting for errors incurred through the loss of DNA strands and/or DNA damage arising from stringent wash conditions or de-blocking (reversible terminator removal) over multiple assay reaction cycles.

In general, the assay for measuring CNR for a solid-phase bioassay includes the steps of:

(1) preparing the disclosed low binding substrates to be functionalized with receptor, target, and/or capture oligonucleotides of interest.

(2) capturing the receptor, target, and/or capture oligonucleotides, which may be directly labeled or may be a precursor to a subsequent labeling reaction. If no amplification or additional probe-labeling step is required, one proceeds to step 5. If a probe labeling step is required to create a reporter, one proceeds to step 4. Otherwise, one proceeds to step 3.

(3) perform amplification of the receptor, target, and/or capture oligonucleotides via traditional immunoassay signal amplification, oligonucleotide replication amplification (e.g., using bridge, isothermal, RCA, HDA, or RCA-MDA amplification strategies).

(4) probe the amplified target with a reporter label (e.g., through the use of a fluorescent species or other type of reporter). This step is applicable to any surface-based bioassay including, but is not limited to, genotyping, nucleic acid sequencing, or surface-based target/receptor identification.

(5) perform an appropriate detection methodology. For fluorescence imaging, the detection methodology can be configured in various ways. For example, traditional optical microscopy methods would include all or a subset of the following components: illumination or excitation light source, objective, sample, other optical components (such as a tube lens, optical filters, dichroic reflectors, etc.), and a detection modality (e.g., using an EMCCD camera, CCD camera, sCMOS, CMOS, PMT, APD or other traditional method for measuring light levels). For non-light-based detection, electrical signals can be measured using various means including, but not limited to, field effect transistor (FET) detection, electrode-based measurement of electrical signals (direct or alternating), tunneling currents, measurement of magnetic signals, etc.

The use of imaging and signal processing from a specified field-of-view (FOV) to calculate the CNR is illustrated in FIG. 8, where CNR=(Signal−Background)/(Noise), and where Background=($B_{intrastitial}+B_{interstitial}$) as illustrated in the figure.

For the following examples of the calculation of CNR for clonally-amplified clusters of nucleic acid sequences on the low-binding supports of the present disclosure, an image analysis program was used to find representative foreground bright spots ("clusters"). Typically, spots are defined as a small connected region of image pixels that exhibit a light intensity above a certain intensity threshold. Only connected regions that comprise a total pixel count that falls within a specified range are counted as spots or clusters. Regions that are too big or too small in terms of the number of pixels are disregarded.

Once a number of spots or clusters have been identified, the average spot or foreground intensity and other signal statistics are calculated, for example, the maximum, average, and/or interpolated maximum intensities may be calculated. The median or average value of all spot intensities is used to represent spot foreground intensity.

A representative estimate of the background region intensity may be determined using one of several different methods. One method is to divide images into multiple small "tiles" which each include, e.g., 25×25 pixels. Within each tiled region, a certain percentage of the brightest pixels (e.g., 25%) are discarded, and intensity statistics are calculated for the remaining pixels. Another method for determining background intensity is to select a region of at least 500 pixels, or larger, which is free of any foreground "spots" (as defined in the previous step), and then to calculate intensity statistics. For either of these methods, a representative background intensity (median or average value) and standard deviation are then calculated. The standard deviation of the intensity in the selected regions is used as the representative background variation.

Contrast-to-noise ratio (CNR) is then calculated as (foreground intensity−background intensity)/(background standard deviation).

Figure 21:
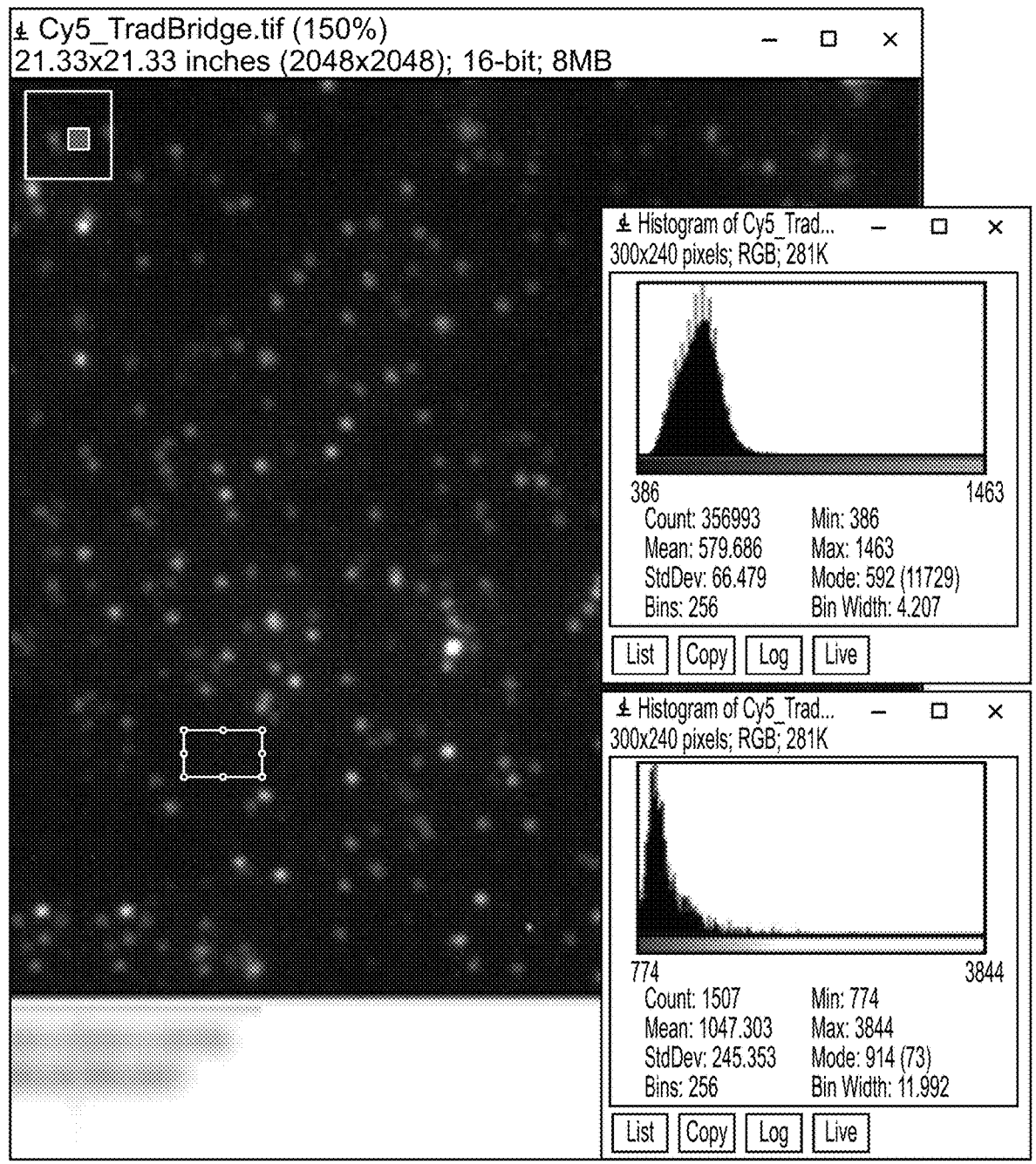
FIG. 21 provides an example of fluorescence image and intensity data for a low-binding support of the present disclosure on which solid-phase nucleic acid amplification was performed to create clonally-amplified clusters of a template oligonucleotide sequence.
Figure 22:
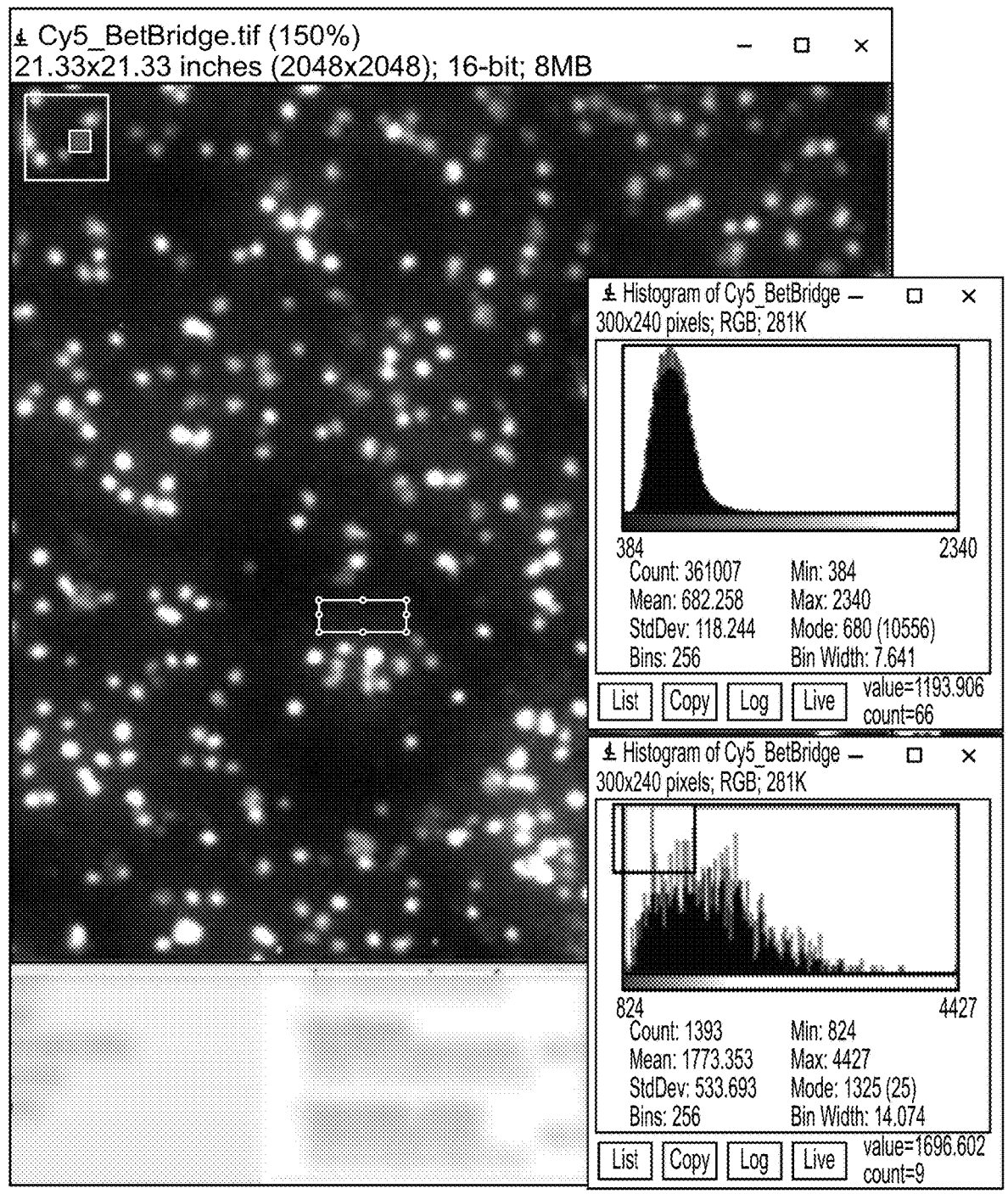
FIG. 22 provides a second example of fluorescence image and intensity data for a low-binding support of the present disclosure on which solid-phase nucleic acid amplification was performed to create clonally-amplified clusters of a template oligonucleotide sequence.
Figure 23:
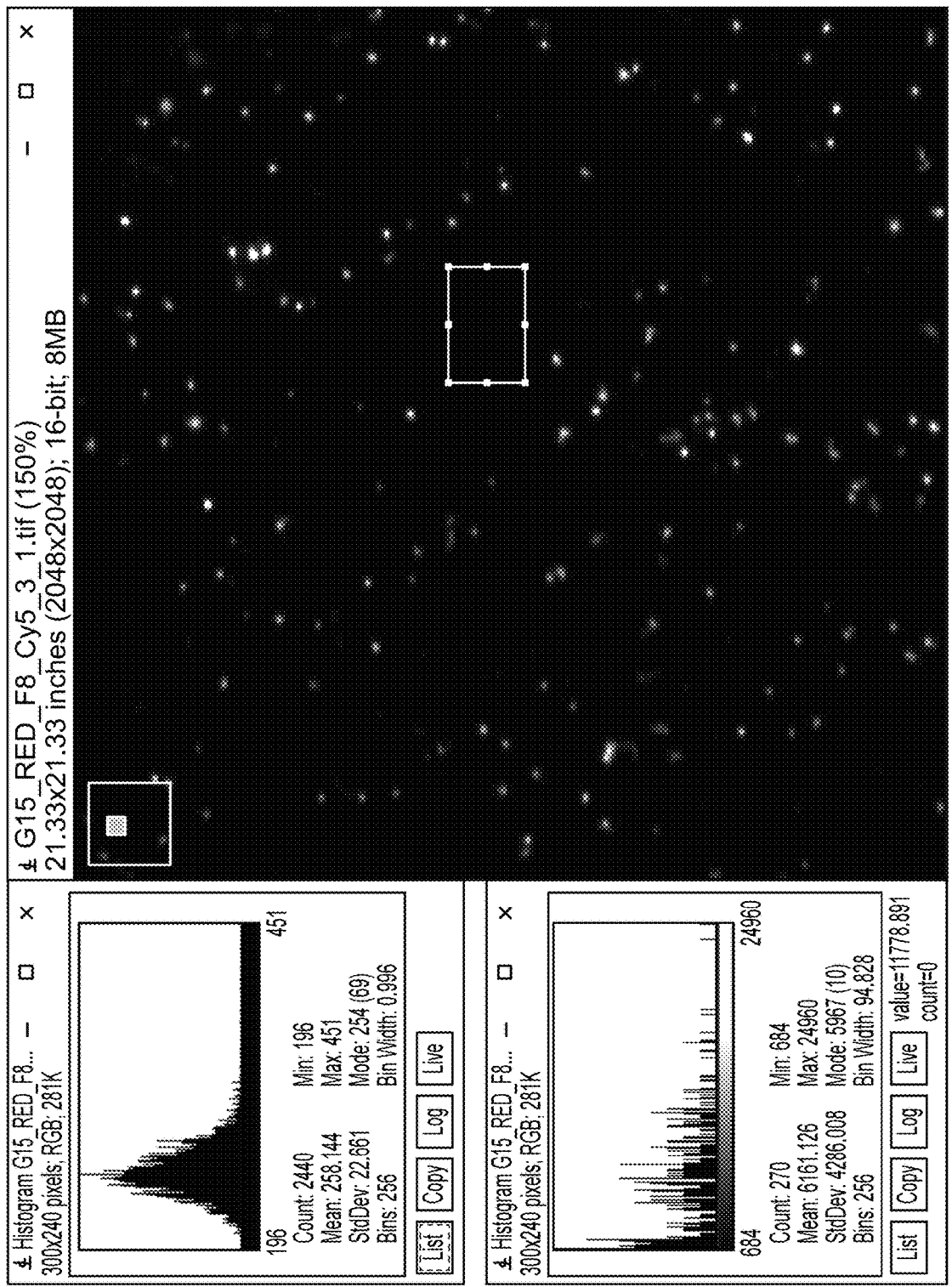
FIG. 23 provides an example of fluorescence image and intensity data for a low-binding support of the present disclosure on which solid-phase nucleic acid amplification was performed to create clonally-amplified clusters of a template oligonucleotide sequence.
Figure 24:
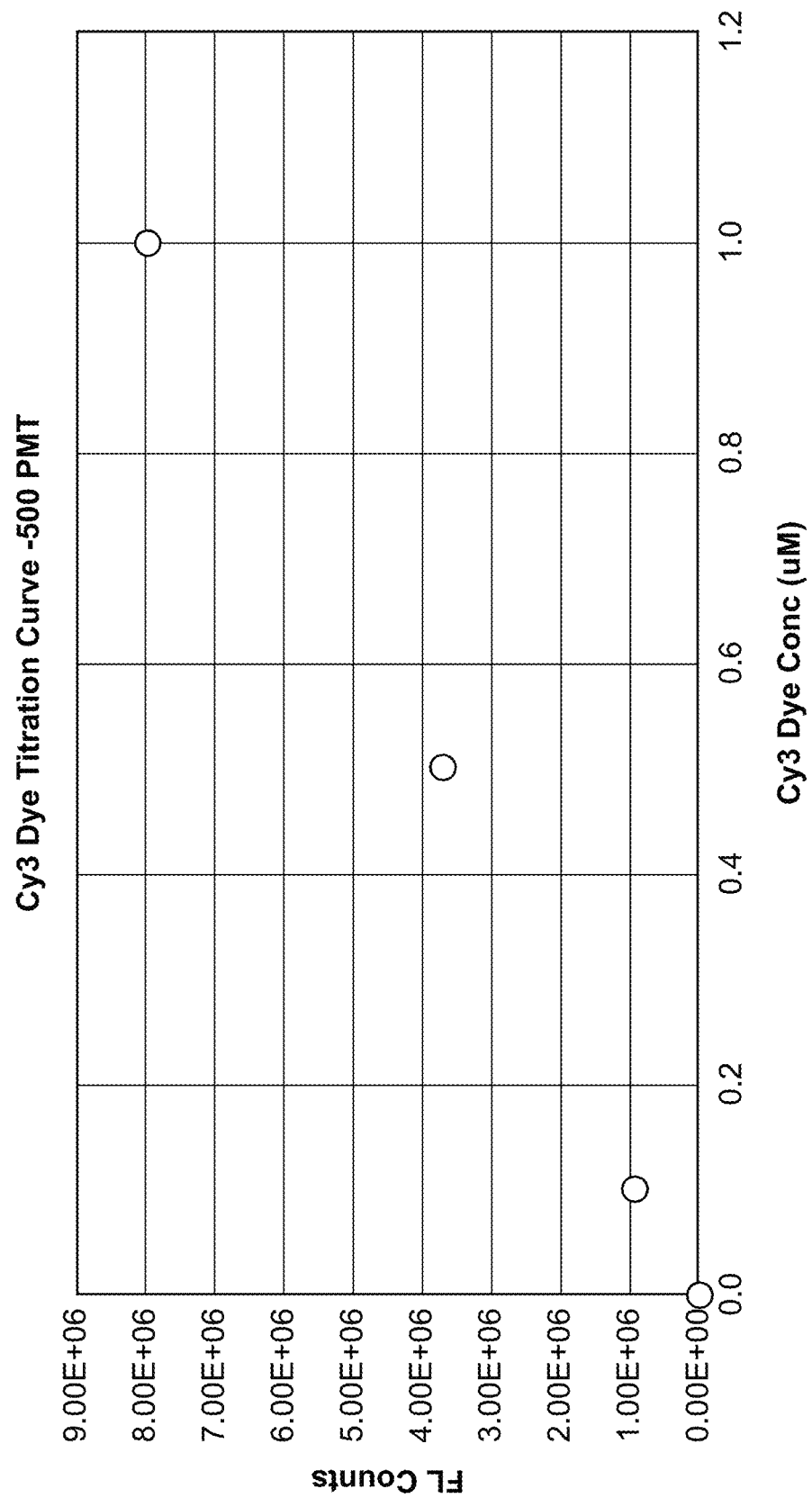
FIG. 24 provides an example of a fluorescence calibration curve used to estimate the surface density of primer oligonucleotides tethered to a support surface.

FIGS. 21-23 provide examples of raw image data and intensity data histograms used to calculate CNR for difference combinations of nucleic acid amplification methodology and the low-binding supports described here. In each of these examples, the upper histogram is the background pixel intensity histogram, the lower histogram is the foreground spot intensity histogram, and a portion of the original image is also included. Note that the images are not on the same intensity scale, so visual brightness perception does not indicate actual intensity.

For these examples, low binding solid supports were created using the methods previously discussed. Oligonucleotide primers (one or two primer sequences depending on the amplification scheme used) were grafted using the disclosed methods at varying densities. Surface densities for each of these experiments were estimated to be approximately 100K primers/$\mu m^2$. Primer surface density was estimated using the following methodology: (i) a fluorescence titration curve was prepared using a GE Typhoon (GE Healthcare Lifesciences, Pittsburgh, Pa.) and a capillary flow cell of known area (40 $mm^2$), height (0.5 mm), and volume (200 µl) containing known concentrations of Cy3-dCTP, (ii) the primers grafted to the low-binding support were hybridized to Cy3-labeled complementary oligonucleotides using a conventional hybridization protocol (3× saline sodium citrate (SSC) at 37 degrees C. or at room temperature (RT); hybridization conditions should be characterized for completeness), fluorescence intensity for the resulting signal on the surface was measured using the same GE Typhoon instrument used to generate the calibration curve, (iii) and the number of primer molecules tethered per unit area of surface was calculated based on a comparison of the measured surface signal to the calibration curve.

DNA library sequences were then hybridized to the tethered primers. The hybridization protocols used for the library hybridization step can vary depending on surface properties, but controlled library input is required to create resolvable DNA amplified colonies.

DNA amplification was performed for this example using the following protocols: (i) bridge amplification @ 28 cycles with primer density of approximately 1K primers/$um^2$, (ii) bridge amplification @ 28 cycles with higher primer density>5K primers/$um^2$, and (iii) rolling circle amplification (RCA) for 90 minutes with primer density of approximately 2-4 K primers/$um^2$.

Post amplification, the amplified DNA was hybridized with a complementary "sequencing" primer and a sequencing reaction mix comprising a Cy3-labeled dNTP was added ("first base" assay) to determine the first base CNR for each of the respective methodologies. The sequencing reaction mixture used for the "first base assay" can include any combination of labeled nucleotides, such that 4 bases can be discriminated, an enzyme that incorporates the modified nucleotide triphosphate (dNTP), and a relevant incorporation buffer, metal cations and cofactors, etc.

Following first base incorporation, the sequencing reaction mixture was exchanged with buffer, imaging was performed using the same GE Typhoon instrument, and CNR was calculated on the resulting images.

FIG. 21 provides an example of fluorescence image and intensity data for a low-binding support of the present disclosure on which solid-phase nucleic acid amplification was performed using bridge amplification @ 28 cycles with primer density of approximately 2K primers/$um^2$ to create clonally-amplified clusters of a template oligonucleotide sequence. In this example, the background intensity was 592 counts (with a standard deviation of 66.5 counts), the foreground intensity was 1047.3 counts, and the calculated CNR=(1047.3−592)/66.5=455.3/66.5=6.8. The estimated non-specific noise=(592−100)/(1047−100)=52%.

FIG. 22 provides a second example of fluorescence image and intensity data for a low-binding support of the present disclosure on which solid-phase nucleic acid amplification was performed using bridge amplification @ 28 cycles with higher primer density>5K primers/$um^2$ to create clonally-amplified clusters of a template oligonucleotide sequence. In this example, the background intensity was 680 counts (with a standard deviation of 118.2 counts), the foreground intensity was 1773 counts, and the calculated CNR=(1773−680)/118.2=1093/118.2=9.2. The estimated non-specific noise=(680−100)/(1773−100)=35%.

FIG. 23 provides an example of fluorescence image and intensity data for a low-binding support of the present disclosure on which solid-phase nucleic acid amplification was performed using rolling circle amplification (RCA) for 90 minutes with primer density of approximately 100 K primers/$um^2$ to create clonally-amplified clusters of a template oligonucleotide sequence. In this example, the background intensity was 254 counts (with a standard deviation of 22.7 counts), the foreground intensity was 6161 counts, and the calculated CNR=(6161−254)/22.7=5907/22.7=260. Note the dramatic improvement in CNR achieved through the use of this combination of low-binding surface and amplification protocol. The estimated non-specific noise=(254-100)/(6161-100)=3%.

Example 9—Modification of Polymer Support Surfaces

Modification of a surface for the purposes disclosed herein involves making surfaces reactive against many chemical groups (—R), including amines. When prepared on an appropriate substrate, these reactive surfaces can be stored long term at room temperature for example for at least 3 months or more. Such surfaces can be further grafted with R-PEG and R-primer oligomer for on-surface amplification of nucleic acids, as described elsewhere herein. Plastic surfaces, such as cyclic olefin polymer (COP), may be modified using any of a large number of methods known in the art. For example, they can be treated with Ti:Sapphire laser ablation, UV-mediated ethylene glycol methacrylate photografting, plasma treatment, or mechanical agitation (e.g., sand blasting, or polishing, etc.) to create hydrophilic surfaces that can stay reactive for months against many chemical groups, such as amines. These groups may then allow conjugation of passivation polymers such as PEG, or biomolecules such as DNA or proteins, without loss of biochemical activity. For example, attachment of DNA primer oligomers allows DNA amplification on a passivated plastic surface while minimizing the non-specific adsorption of proteins, fluorophore molecules, or other hydrophobic molecules.

Additionally, surface modification can be combined with, e.g., laser printing or UV masking, to create patterned surfaces. This allows patterned attachment of DNA oligomers, proteins, or other moieties, providing for surface-based enzymatic activity, binding, detection, or processing. For example, DNA oligomers may be used to amplify DNA only within patterned features, or to capture amplified long DNA concatemers in a patterned fashion. In some embodiments, enzyme islands may be generated in the patterned areas that are capable of reacting with solution-based substrates. Because plastic surfaces are especially amenable to these processing modes, in some embodiments as contemplated herein, plastic surfaces may be recognized as being particularly advantageous.

Furthermore, plastic can be injection molded, embossed, or 3D printed to form any shape, including microfluidic devices, much more easily than glass substrates, and thus can be used to create surfaces for the binding and analysis of biological samples in multiple configurations, e.g., sample-to-result microfluidic chips for biomarker detection or DNA sequencing.

Specific localized DNA amplification on modified plastic surfaces have been achieved that produced spots with an ultra-high contrast to noise ratio and very low background when probed with fluorescent labels.

We have grafted a representative hydrophilized and amine reactive cyclic olefin polymer surface with amine-primer and amine-PEG and found that it supports rolling circle amplification. We then discovered that when probed with fluorophore labeled primers, or when labeled dNTPs added to the hybridized primers by a polymerase, bright spots of DNA amplicons were observed that exhibited signal to noise ratios greater than 100 with backgrounds that are extremely low, indicating highly specific amplification, and ultra-low levels of protein and hydrophobic fluorophore binding which are hallmarks of the high accuracy detection systems such as fluorescence-based DNA sequencers.

Figures 25A, 25B:
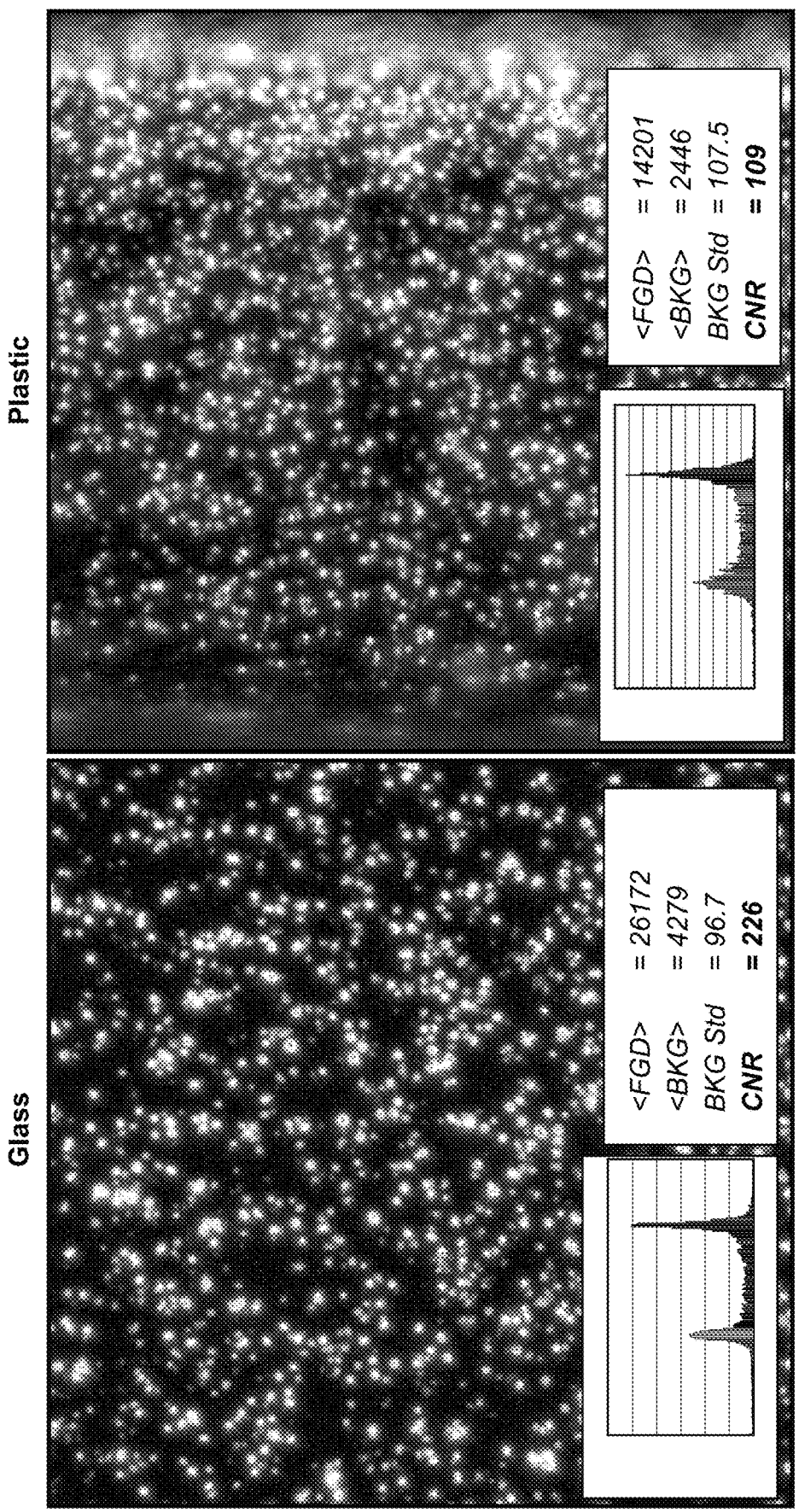
FIGS. 25A-B provide non-limiting examples of modified glass and polymer surfaces of the present disclosure having bound amplicons comprising fluorescently labeled nucleotides.

Here a plastic flow cell is tested that is populated with tethered DNA clusters and probed for the 1st base of the library sequence. For population of the surface with DNA, a hydrophilized cyclic olefin polymer (COP) plastic surface was grafted with 25-mer amine-primer 1, amine-primer 2, and amine-5K PEG as for PEG-NHS coated glass surfaces, as previously described in Examples 1 and 7 and elsewhere herein. 5 pM of a circularized DNA library that contains primer 2 sequence, sequencing primer sequence and a sequence that is complementary to primer 1, in addition to the library insert, was then hybridized to the surface for 15 minutes. Rolling Circle Amplification (RCA) was then performed as described in Examples 2-5 and elsewhere herein, for the creation of concatemeric sequence DNA coils of up to 0.5-1 Mb in length. The sequencing primer was hybridized, and the 1st base was incorporated using a fluorophore labeled dNTP set with a polymerase to label clusters with 3 different colors as shown in FIG. 25A.

A parallel experiment using identical parameters, starting with a glass, rather than a COP surface (with surface preparation as described in Example 7) was carried out in order to provide a comparison between passivated glass and passivated COP surfaces. As shown in FIGS. 25A-B, the signal produced by incorporation of the first fluorescently labeled base on COP surfaces is comparable to that obtained on similarly treated glass surfaces, both in terms of the intensity and the resolution of the observed spots. This suggests that the methods disclosed herein provide a general method for the preparation of surfaces for the immobilization, amplification, and detection of nucleic acids.

Figure 26B:
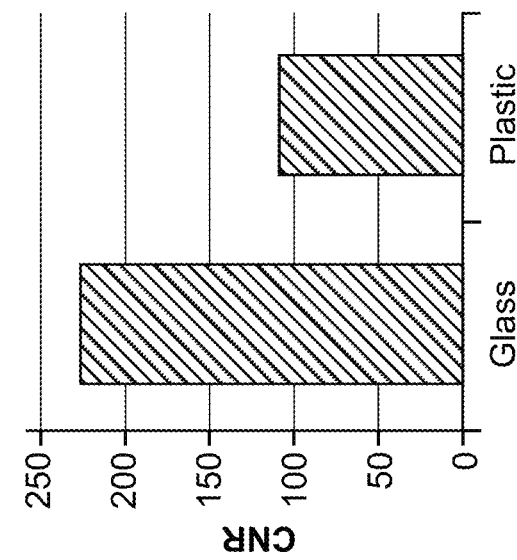
FIGS. 26A-B provide analysis of the images at FIG. 25A and FIG. 25B. At FIG. 26A, one sees signal intensity, left, and background intensity, right, for each of glass and plastic surfaces. For each, signal intensity is substantially greater than background intensity. At FIG. 26B, one sees a graphic depiction of CNR values for each of glass and plastic surfaces. At left, glass yields a CNR of 226, while at right, plastic yields a CNR of 109, consistent with the insets of FIG. 25A and FIG. 25B.
Figure 26A:
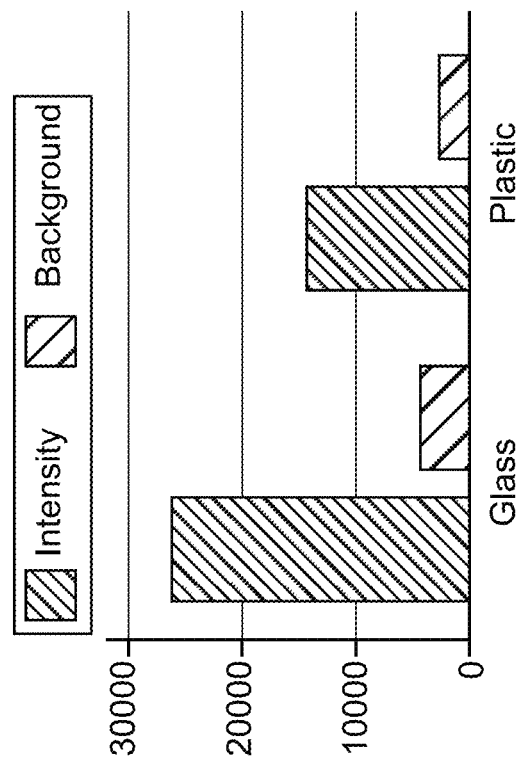

Intensity and CNR are determined for both glass and plastic. One sees at FIG. 26A that both glass and plastic exhibit an intensity of signal under detection conditions that is substantially above background. For both glass and plastic, intensity of signal is at left and background is depicted at right. One sees at FIG. 26B that CNR for both glass and plastic are above 50 under the conditions assayed.

Example 10—Surface Production

A surface exhibiting negligible nonspecific binding to organic dyes and proteins, exhibiting stability up to at least 95 C, chemical stability to High pH (0.1 M NaOH), Low pH (>5.0); organic solvents (Methanol, Ethanol, Acetonitrile, Formamide, oxidants, phosphines), long term storage stability, low input library requirements and scalable primer loading is produced as follows. The process comprises cleaning and silanizing or passivating the surface.

The surface is washed using a 2M KOH solution in combination with an alconox/hellmanex detergent and rinsed using ethanol. The surface is then heated to 560 C to expose OH groups. Surfaces are alternately or in combination subjected to a plasma treatment.

Surfaces are silanized using 5 mg/mL Silane-5kPEG-NHS (99.9% Ethanol/0.01% Acetic acid) and heated to 65 C, and tested using a KOH/Detergent/Heat cleaned surface. Alternately or in combination, surfaces are silanized using 10 mg/mL Silane-5kPEG-NHS (90% DMF/10% 100 mM MES PH5.5) and heated to 25 C, and tested using KOH/Detergent/Heat cleaned surface or with a plasma treated surface.

A number of dyes are compatible with these surfaces, such as Cy3-C, R11-U, Cy3.5C, 647N-A, Cy5-G, 660-U, Cy5.5-C (Note: Only dye at 200 nM). An exemplary dye mix comprises Cy3-A, Cy3.5-C, Cy5-U, AHO690-G.

Such surfaces are tuneably loaded with primers, at low concentrations ($5.0 \times 10^4$ primers/um$^2$), at high concentrations ($1.0 \times 10^7$ primers/um$^2$), and at concentrations of values within a range defined by these endpoints or outside of this range.

Concentration is optionally measured as follows. Make Cy3-dCTP solution of different concentrations, measure the FL intensity with a GE Typhoon (GE Healthcare Lifesciences, Pittsburgh, Pa.) or suitable instrument in a capillary with fixed dimension (0.5 mm×5 mm or other area). This yields the primer loading when area is known and number of molecules is known.

Concentrations, in primers/um$^2$ of 80,000; 160,000; 320,000; 640,000; 1,300,000; 2,600,000; and 5,100,000 have been measured using this approach, and other concentrations of values within a range defined by these endpoints or outside of this range are readily attainable. These densities are facilitated by the presence of multilayer PEG or other surfaces as disclosed herein.

Surfaces were seen to show no significant reduction in stability over one week of storage.

Densities were measured for a number of surface variants and results were as seem below. 3-layer multi-arm PEG (8, 16, 8) on PEGamine-APTES, exposed to two layers of 7 uM primer pre-loading, exhibited a concentration of 2,000,000 to 10,000,000 on the surface. Similar concentrations were observed for 3-layer multi-arm PEG (8, 16, 8) and (8, 64, 8) on PEGamine-APTES exposed to 8 uM primer, and 3-layer multi-arm PEG (8, 8, 8) using star-shape PEG-amine to replace dumbbell-shaped 16mer and 64mer.

Using these approaches, it was observed that increased primer densities yielded higher foreground intensities, higher colony densities and higher CNR. For example, a 10 pM input yielded a CNR of 10 on a surface having a Primer Density<$1.0 \times 10^4$ primer/um$^2$ while a similar input yielded a CNR of 40-60 at a Primer Density>$1.0 \times 10^6$ primer/um$^2$.

Example 11—High CNR Surfaces Yield High Quality Data

Current state of the art surfaces, and low and high CNR surfaces such as those disclosed herein were tested as to their fluorescence as detected at a first channel and a second channel, corresponding to a first and a second dye.

Figure 27:
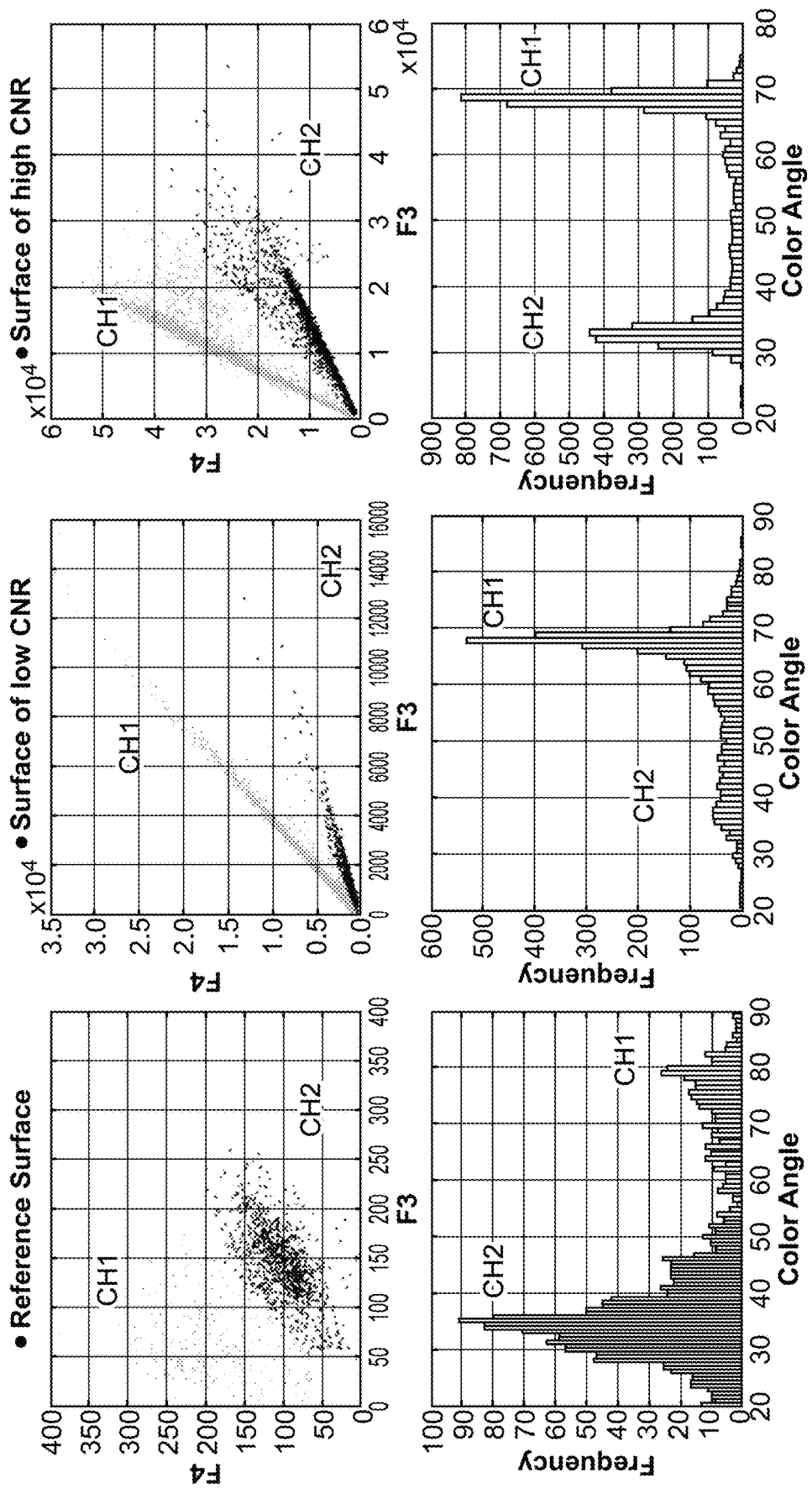
FIG. 27 provides analysis of surfaces as to the accuracy of their data. Data is collected in two channels and is depicted in scatter pot from (top) and quantified (bottom) for each of a commercially available, low CNR and high CNR surface from left to right.

One observed that, with increasing CNR, one sees a clearer resolution of individual detection events. These detection events align along distinct axes corresponding to dye emission spectra, rather than to higher error 'clouds' as seen in the top three files of FIG. 27. Turning to the bottom three files of FIG. 27, this more accurate data collection manifests itself as narrower, higher peaks at specific expected wavelengths and fewer data points at intermediate positions. This more clearly resolved dataset translates into more accurate fluorescence-based base calls resulting from assays performed on high CNR surfaces.

Example 12—Clonally-Amplified, Multimeric Target Oligonucleotide Molecules

Figure 28:
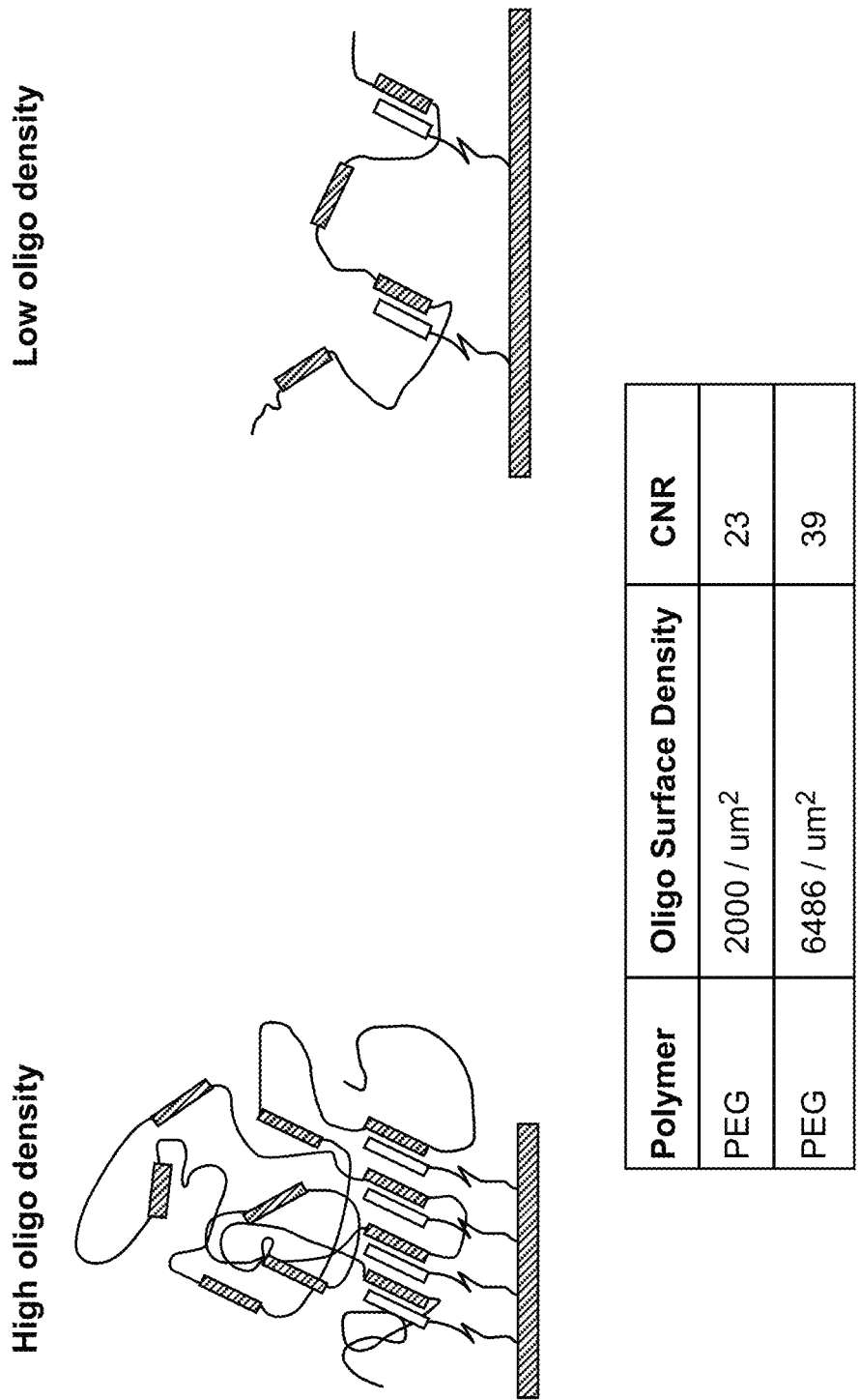
FIG. 28 provides a schematic illustration of a multimeric target oligonucleotide sequence hybridized to a surface comprising a high surface density of oligonucleotide adapter or primer molecules (left) and to a surface comprising a lower surface density of oligonucleotide adapter or primer molecules (right).

FIG. 28 provides a schematic illustration of a clonally-amplified, multimeric target oligonucleotide sequence hybridized to a surface comprising a high surface density of oligonucleotide adapter or primer molecules such as, for example, 4,000 or more molecules per um2 (left) and to a surface comprising a lower surface density such as, for example, below 500 molecules per um2 of oligonucleotide adapter or primer molecules (right) and illustrates the resulting improvement in CNR that may be achieved. Several surfaces were prepared to have oligonucleotide density that is higher than the 2000 molecules/uM$^2$, and the fluorescence image of the surfaces has a contrast to noise ratio of greater than 20.

Example 13—Reduction in Input Nucleic Acid Requirements

Figure 29:
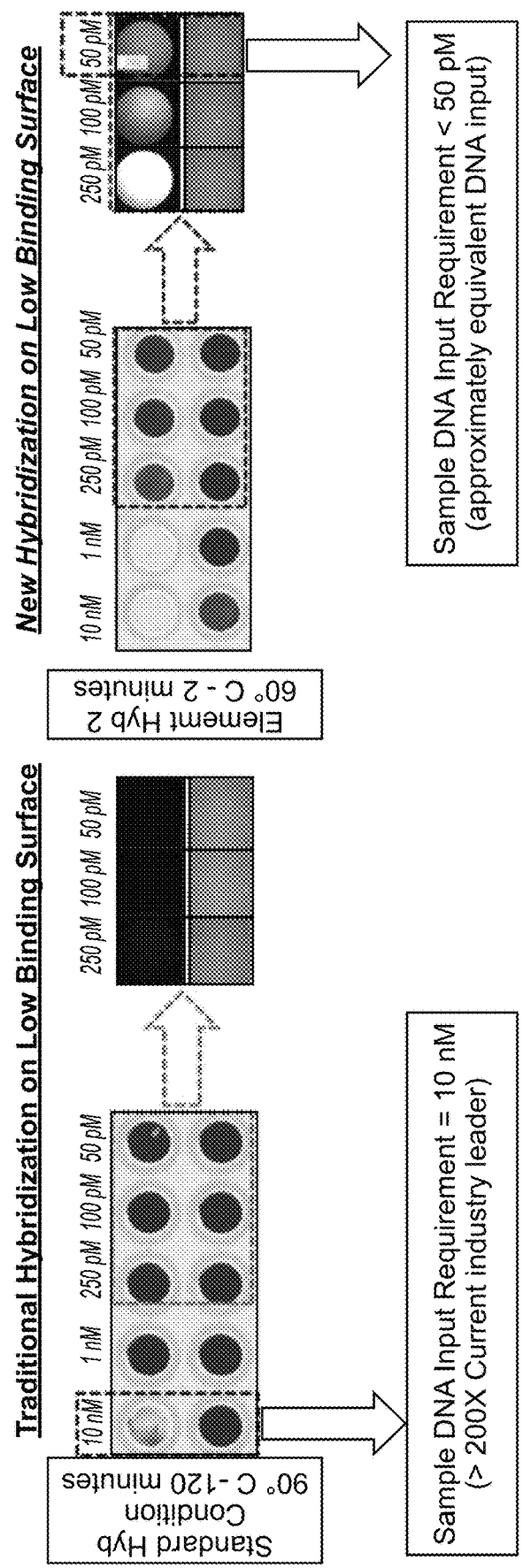
FIG. 29 provides a comparison of the experimental outcomes for performing a traditional hybridization reaction on a low-binding support surface of the present disclosure and performing an optimized hybridization reaction on the low-binding support surface of the present disclosure.

FIG. 29 provides a comparison of the experimental outcomes for performing a traditional hybridization reaction on a low-binding support surface of the present disclosure and performing an optimized hybridization reaction on the low-binding support surface of the present disclosure. Traditional hybridization approaches use SSC buffer and heating to 95 degrees and then a slow 2 hour cool. After attaching oligonucleotide primers to the low-binding support surface, efficient hybridization of target nucleic acids to the oligonucleotide primers may suffer from diminished collisional frequencies on the low binding surface. Due, at least in part, to decreased coupling of capture oligonucleotides on prior art surfaces, traditional hybridization methods for adding target DNA to surface-bound primers requires input DNA concentrations of up to 10 nM (see FIG. 29, left, showing binding of labeled target oligonucleotide to binding support surfaces). Even at these high concentrations, coupling of target oligonucleotides is limited. In comparison, a non-complementary oligonucleotide at the same respective concentrations was used as a negative control (bottom row FIG. 29) By comparison, using new hybridization reaction conditions that have been developed, which include a mixture comprising PEG, a solvent with a decreased polarity as compared to water, such as ethanol, methanol, isopropanol, acetonitrile, butanol, or the like, formamide and a low pH buffer (<7) target nucleic acid sequences were hybridized to surfaced-attached oligonucleotides at input concentrations of the target nucleic acid as low as 50 pM. The drop in the target nucleic acid input concentration indicates a roughly 200-fold increase in hybridization efficiency (see FIG. 29, right, showing the binding of labeled target oligonucleotide to the disclosed low-binding surfaces), which provides the disclosed low-binding support surfaces with a significant advantage for use in sequencing technologies where input library DNA may be scarce. The efficient primer coupling process and hybridization conditions can allow preparation of a surface having a low nonspecific binding and high surface density of oligonucleotide primers that would not be achieved using traditional primer coupling chemistries or hybridization conditions described in the art. In comparison, a non-complementary oligonucleotide at the same respective concentrations was used as a negative control (bottom row FIG. 29, right) The detectable tag for each of the images is Cyanine dye-3 (Cy3), and wherein a fluorescence image of the surface acquired) 20×, 0.75 NA, a 532 nm light source, a bandpass and dichroic minor filter set optimized for 532 nm long-pass excitation and Cy3 fluorescence emission filter, a Semrock 532 nm dichroic reflector, and a camera (e.g., an Andor sCMOS, Zyla 4.2)

Traditional or standard conditions were tested with hybridization reporter probe (complementary oligonucleotide sequences labeled with a Cy™3 fluorophore at the 5' end) in 2×-5× saline-sodium citrate (SSC) buffer (std) at concentrations reported at 90 degree with a slow cool process (2 hours) to reach 37 degrees. The surfaces used for both testing conditions were ultra-low non-specific binding surfaces having a level of non-specific Cy3 dye absorption of less than about 0.25 molecules/µm2. Wells were washed with 50 mM Tris pH 8.0; 50 mM NaCl. Images were obtained acquired using an inverted microscope (Olympus IX83) equipped with 100× TIRF objective, NA=1.4 (Olympus), dichroic mirror optimized for 532 nm light (Semrock, Di03-R532-t1-25×36), a bandpass filter optimized for Cy3 emission, (Semrock, FF01-562/40-25), and a camera (sCMOS, Andor Zyla) under non-signal saturating conditions for 1 s, (Laser Quantum, Gem 532, <1 W/cm2 at the sample) while sample is immersed a buffer (25 mM ACES, pH 7.4 buffer). Conditions 50% ACN+MES with 1 um oligonucleotide graft concentration and 25% ACN+MES+20% PEG+ 10% formaldehyde with 5.1 uM oligonucleotide graft concentration were chosen to test the viability of these conditions to improve existing standard surface hybridization protocols on a low binding substrate. The oligonucleotide probe was added at concentrations specified and hybridization performed for 2 min at 50 degrees C. Images were collected as described above and results shown in the figure.

Figure 30:
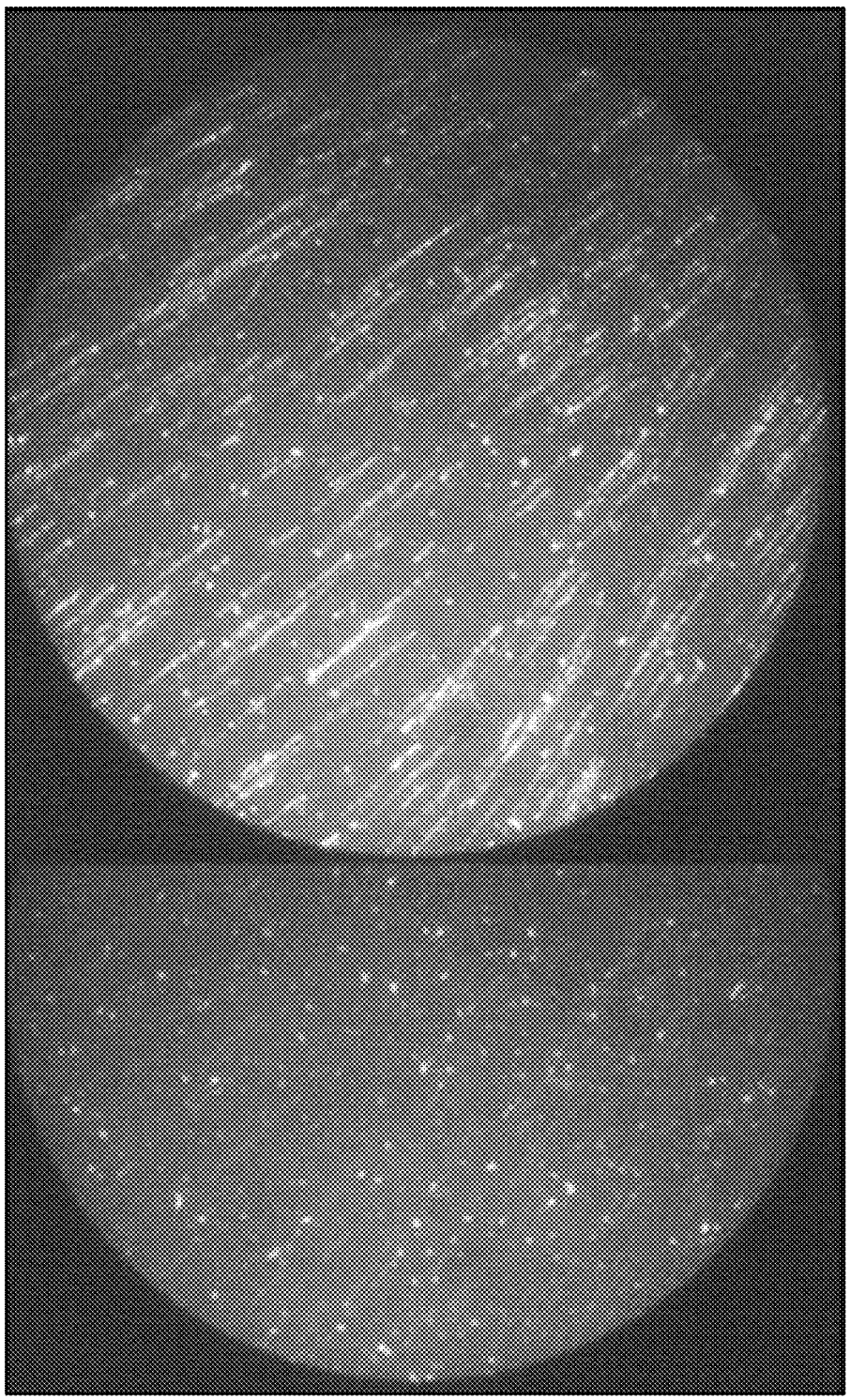
FIG. 30 provides an illustration of the experimental outcome of performing a traditional hybridization reaction on a low-binding support of the present disclosure, followed by performing RCA or Bridge amplification.
Figure 31:
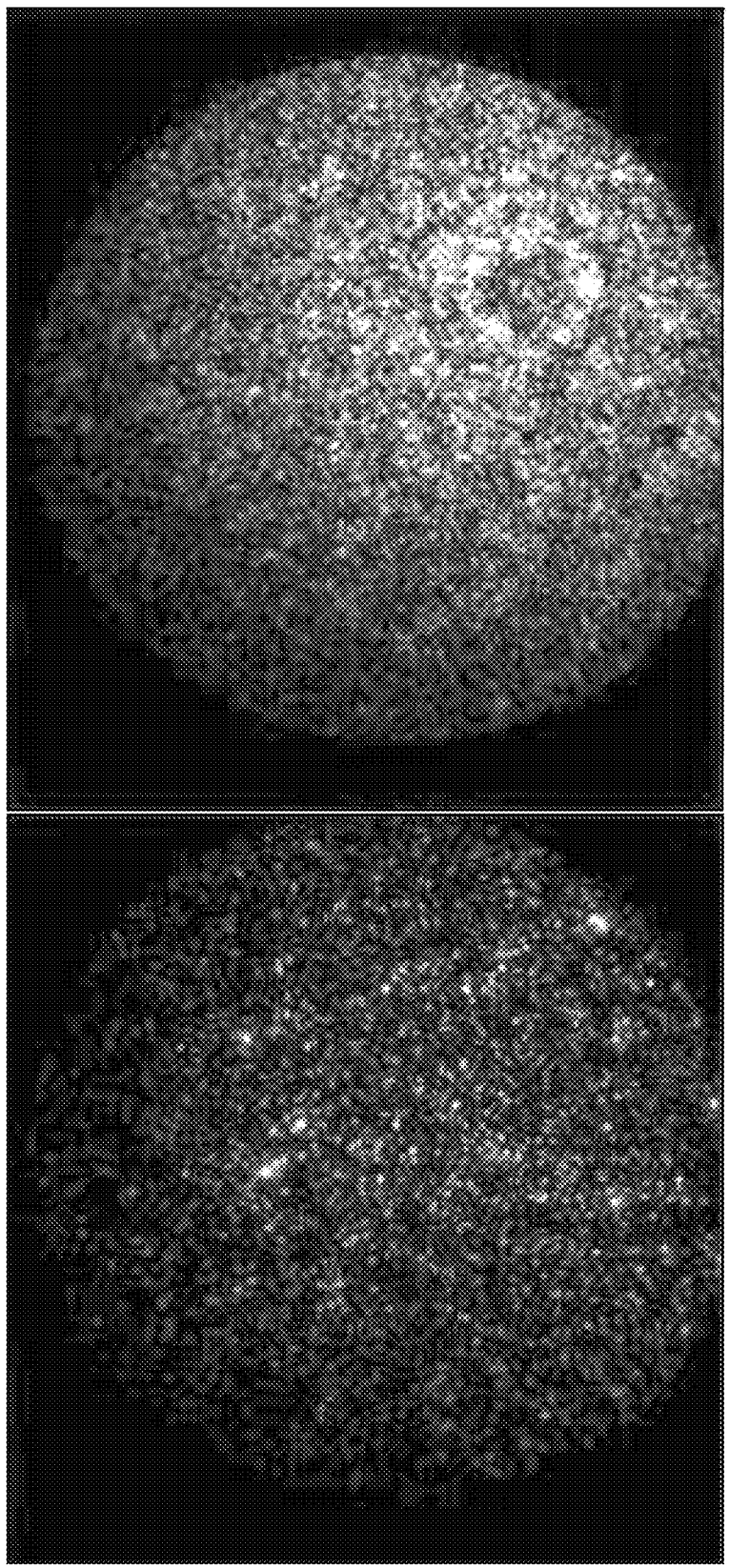
FIG. 31 provides an illustration of the experimental outcome of performing an optimized hybridization reaction on a low-binding support of the present disclosure, followed by performing RCA or Bridge amplification.
Figure 32:
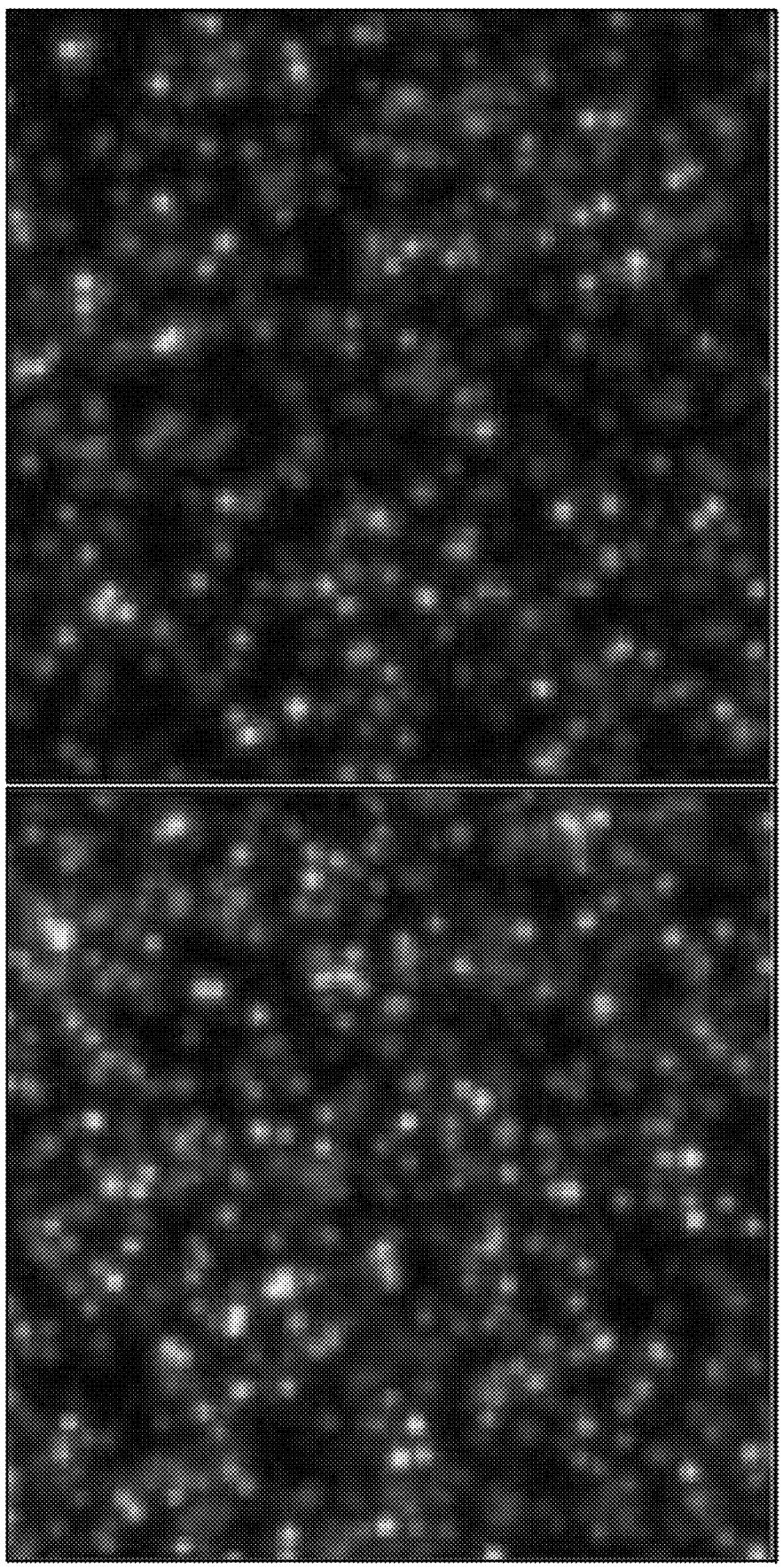
FIG. 32 provides an illustration of the experimental outcome of performing an optimized hybridization reaction on a low-binding support of the present disclosure prepared using improved coupling chemistry for attaching oligonucleotide adaptor or primer molecules to the surface, followed by performing RCA or Bridge amplification.
Figure 33:
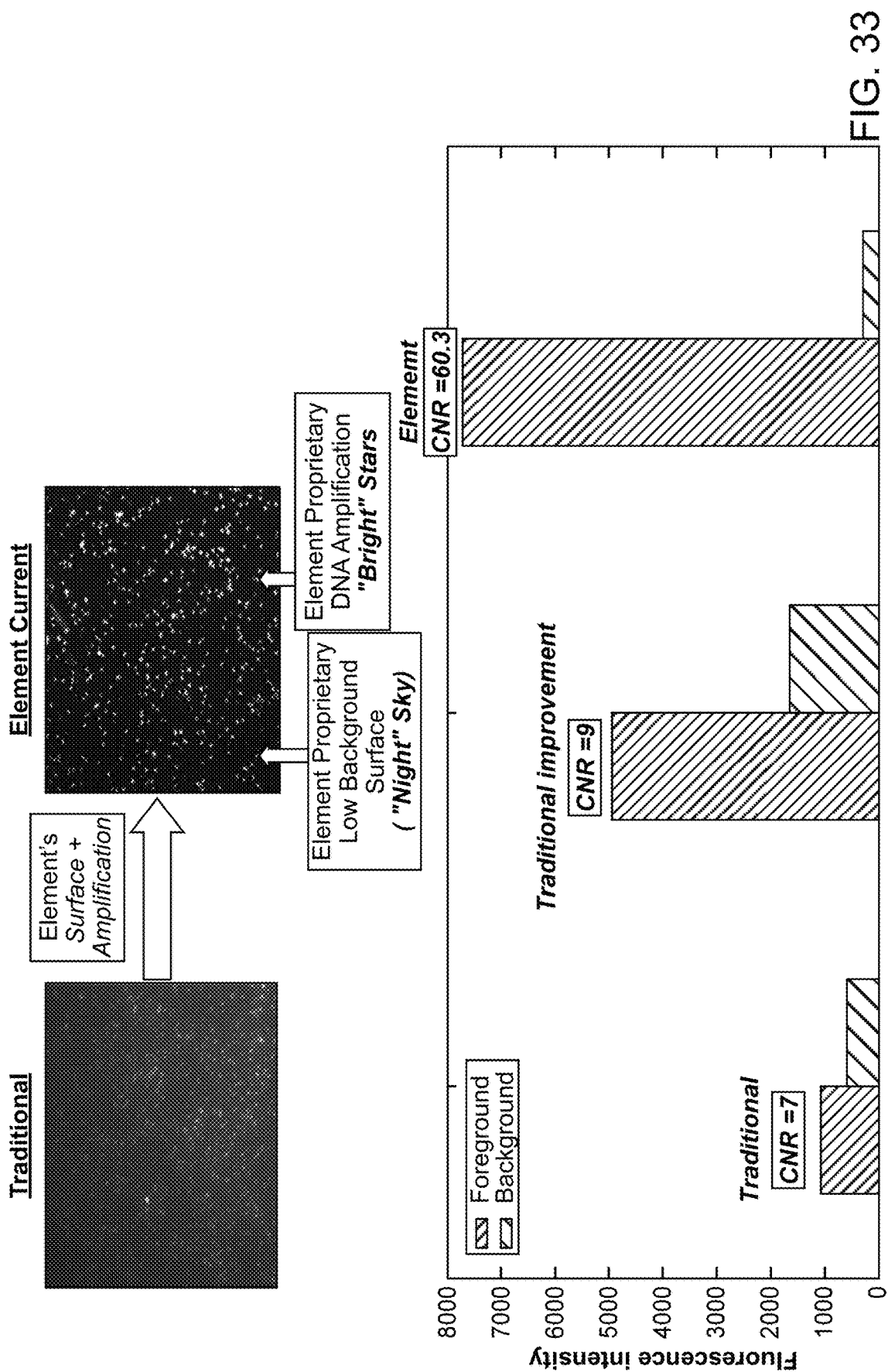
FIG. 33 provides non-limiting examples of fluorescence images of a traditional support surface and a low-binding support surface of the present disclosure to which target oligonucleotides have been hybridized and amplified. The plot illustrates the contrast-to-noise ratios measured from images such as those provided in the examples for a polyacrylamide surface with bridge amplification protocol, low binding support with a standard bridge amplification protocol and a primer density<1000 oligonucleotides/um$^2$, and a low-binding support surface of the present disclosure in combination with an improved solid-phase nucleic acid amplification method on a surface with a primer density>1000 oligonucleotides/um$^2$.

Example 14—Comparison of Traditional Oligo Primer Coupling Chemistries, Hybridization Reaction Conditions, and Amplification Techniques on Low-Binding Support Surfaces FIGS. 30-32 provide comparisons of the experimental outcomes for performing traditional hybridization reactions or improved hybridization reactions using the methodologies outlined in description of FIG. 29 on the low-binding supports of the present disclosure where the oligo primers were attached using a conventional coupling chemistry, which for NHS—NH2 coupling reactions are typically performed in sodium bicarbonate buffer at pH=8.3. or an improved coupling chemistry, which entail changing the polarity of the coupling buffer (organic based solvent) with the addition of a buffering component of pH>8.0, and where the hybridization reactions were followed by performing either RCA or Bridge amplification. Amplification of target DNA on low-binding supports having an oligonucleotide primer surface density of less than a distinct surface density threshold, either by PCR-based ("bridge") or by rolling circle amplification, gives elongated or spread target molecules that creates two challenges: 1) diminished packing densities, and 2) diminished signal. As a result, scaling a system for high throughput sequencing applications based on such a surface is drastically impaired. FIG. 30 shows the results of both PCR amplification ("bridge"; right) and rolling circle amplification (left) on low binding surfaces using traditional oligonucleotide coupling chemistries, such that the oligonucleotide density<1000 oligonucleotides/ um2. In these images, labeled amplified target DNA can be seen assuming extended conformations that would present severe difficulties for imaging in sequencing applications. By comparison, FIG. 31 shows the results of PCR/"bridge" amplification and FIG. 32 shows the results of rolling circle amplification (RCA) on surfaces having oligonucleotide primer surface densities of at least 1,000 molecules per µm$^2$. These surfaces support the compaction of the amplified target DNA into highly localized regions that yield high fluorescence intensities from attached labels, and small pixel areas in imaging. The high fluorescence intensities, notably, lead to increased signal when calculating spot intensities for sequencing applications. Importantly, the enhanced contrast-to-noise ratio resulting from the use of the low-binding surfaces disclosed herein is a function of both the very high signal resulting from this compaction of the amplified target DNA, and the very low background provided by the hydrophilic coated surfaces. Each of these images has a labeled nucleotide with individual labels, such that each nucleotide has a different emission label. As an example, the labels may consist of Cy3, Cy3.5, Cy5, and Cy5.5 respectively and then imaged on an Olympus IX83 microscope equipped with a 20×, 0.75 NA, a 532 nm light source, a bandpass and dichroic mirror filter set optimized for 532 nm long-pass excitation and Cy3 fluorescence emission filter, a Semrock 532 nm dichroic reflector, and a camera (Andor sCMOS, Zyla 4.2) at an exposure time of at least 0.5 s Example 15—Comparison of Amplification Reactions on Low-Binding Support Surfaces FIG. 33 provides non-limiting examples of fluorescence images of a traditional support surface and a low-binding support surface of the present disclosure to which target oligonucleotides have been hybridized and amplified. In order to facilitate sequencing accuracy, each amplified target nucleic acid must be clearly separable from other target nucleic acids in images of the support surface. Each target nucleic acid must also, during the sequencing cycle, present a signal (such as a fluorescence signal) that is related to identification of each nucleotide in the sequence (the process referred to as "base-calling"). This base-calling signal, which in many cases is simply the fluorescence intensity provided by a label attached to the target nucleic acid molecules, must be clearly and accurately resolvable above both noise (variation in signal within a spot or target) and background (spurious signal generated nonspecifically due to characteristics of the material forming the experimental milieu). The ratio between contrast and noise ("CNR") defines the ability to accurately determine which base is present at each position in a target nucleic acid sequence, as well as the read length, reproducibility, and throughput of a sequencing system. The presently disclosed low-binding support surfaces provide for reduced nonspecific protein and dye binding, thereby resulting in lower background signal, and a more compact, brighter foreground signal, thereby yielding enhanced CNR and facilitating superior base-calling results in sequencing applications. FIG. 32 shows a comparison between a PEG-coated surface prepared generally according to conventional methods and adapted as necessary for the binding of clonally-amplified target DNA (top, "Traditional); and the low-binding support surfaces of the present disclosure (top, "Element Current"). It is clear from the images that the presently disclosed surfaces show notably sharper, more intense spots for measurement of clonally-amplified DNA than the conventional surface. Quantitative measurement of both spot intensity (fluorescence attributable to clonally-amplified target DNA, equivalent to the sequencing signal) and background intensity show that the CNR for the disclosed low-binding support surfaces (bottom, "Element Current Best") far exceeds that achievable using the conventional surface (bottom, Traditional"), even under ideal imaging conditions such as when using improved hybridization conditions for the binding of target DNA (bottom, 'Traditional Improvement"). This increase in CNR is greater than what could reasonably be expected using a conventional support surface and represents both a qualitative and quantitative improvement over prior art surfaces. These improvements are achieved by generating a support surface that meets several criteria, e.g., reduced nonspecific protein and dye binding, attachment of the correct density of oligonucleotides to the surface, and hybridization/binding of a clonally-amplified target nucleic acid to the surface to yield images with very high CNR that enable enhanced base-calling in sequencing applications.

Example 16—Prophetic Example of Preparing Low-Binding Supports Using Other Polymers A glass slide is physically- or chemically-treated (e.g., using a plasma treatment, a piranha cleaning step, an acid wash, a base wash, high temperature glass annealing, or any combination thereof) to remove organic contaminants and activate surface hydroxyl groups for silane coupling. The prepared glass surface is then reacted with a silane to covalently attached a first layer of functional groups (e.g., primary amines) and/or a hydrophilic polymer layer. In some instances, for example, a silane such as (3-aminopropyl)trimethoxysilane (APTMS) or (3-aminopropyl)triethoxysilane (APTES) 3 (3-acrylopropyl) trimethoxysilane is reacted with the surface using standard protocols to covalently attach primary amine functional groups to the surface. In other instances, a silane-modified polymer, e.g., a hydrophilic, heterobifunctional polymer comprising a silyl group at one end and a second functional group (e.g., a primary amine, carboxyl group, etc.) at the other end may be reacted directly with the surface (e.g., by contacting the clean glass surface with the silane-modified polymer at concentration of 0.1%-2% in ethanol for about 1 to 2 hours followed by rinsing with ethanol and water). Examples of suitable silane-modified polymers include, but are not limited to, silane-PEG-NH$_2$ (having a polyethylene glycol (PEG) molecular weight of, for example, 1000, 2000, 3400, 5000, or 10K Daltons), silane-PEG-COOH (having a PEG molecular weight of, for example, 1000, 2000, 3400, 5000, or 10K Daltons), silane-PEG-maleimide (having a PEG molecular weight of, for example, 1000, 2000, 3400, 5000, or 10K Daltons), silane-PEG-biotin (having a PEG molecular weight of, for example, 1000, 2000, 3400, 5000, or 10K Daltons), silane-PEG-acrylate (having a PEG molecular weight of, for example, 1000, 2000, 3400, 5000, or 10K Daltons), silane-PEG-silane (having a PEG molecular weight of, for example, 1000, 2000, 3400, 5000, or 10K Daltons), silane-modified polypropylene glycols (PPGs) of various molecular weights that comprise an additional functional group, silane-modified poly(vinyl alcohols) (PVAs) of various molecular weights that comprise an additional reactive functional group, silane-modified polyethylenimine (PEIs) of various molecular weights that comprise an additional reactive functional group, silane-modified poly(lysine) of various molecular weights that comprise an additional reactive functional group, and the like, or any combination thereof.

In some instances, at least one additional layer of a hydrophilic polymer layer is coupled to, or deposited on, the glass surface following the initial reaction of the surface with a silane or silane-modified polymer. Any of a number of hydrophilic polymers known to those of skill in the art including, but not limited to, polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxyethyl methacrylate) (PHEMA), poly(oligo(ethylene glycol) methyl ether methacrylate) (POEGMA), polyglutamic acid (PGA), poly-lysine, poly-glucoside, streptavidin, dextran, or any combination thereof may be used where, in the case of covalent coupling, polymer(s) comprising the appropriate monofunctional, homobifunctional, and/or heterofunctional reactive groups are selected for compatibility with the chosen conjugation chemistry. In some cases, a derivatized polymer is used, such as a PEG-amine, a PEG-NHS, or a PEG-Acrylate. In some cases, a bifunctional PEG derivative is used, such as an acrylate-PEG-NHS. In some cases, these additional hydrophilic polymer layers may be coupled to, or deposited on, the previous layer by contacting the surface with a 0.1%-2% polymer in ethanol or an ethanol/aqueous buffer solution for about 5 minutes to about 1 hour at room temperature, followed by rinsing with ethanol or an ethanol/aqueous buffer.

In some instances, a second, third, fourth, fifth, or more additional layers of a hydrophilic polymer may be coupled to, or deposited on, the initial layer of the support surface. In some instances, the polymer molecules within a layer may be cross-linked with each other using appropriate homofunctional or heterofunctional cross-linking reagents. In some instances, the polymer molecules in different layers may be cross-linked with each other. In some instances, one or more of the hydrophilic polymer layers may comprise a branched polymer, e.g., a branched PEG, branched poly(vinyl alcohol) (branched PVA), branched poly(vinyl pyridine), branched poly(vinyl pyrrolidone) (branched PVP), branched), poly(acrylic acid) (branched PAA), branched polyacrylamide, branched poly(N-isopropylacrylamide) (branched PNIPAM), branched poly(methyl methacrylate) (branched PMA), branched poly(2-hydroxylethyl methacrylate) (branched PHEMA), branched poly(oligo(ethylene glycol) methyl ether methacrylate) (branched POEGMA), branched polyglutamic acid (branched PGA), branched poly-lysine, branched poly-glucoside, branched dextran, or any combination thereof.

One of more of the hydrophilic polymer layers may comprise a plurality of covalently-attached oligonucleotide adapter or primer molecules, wherein the oligonucleotide molecules are covalently coupled to the polymer using any of a variety of suitable conjugation chemistries known to those of skill in the art. In some instances, the oligonucleotide adapter or primer molecules are covalently coupled to the polymer in solution, i.e., prior to coupling or depositing the polymer on the surface. In some instances, the oligonucleotide adapter or primer molecules are covalently coupled to the polymer after it has been coupled to or deposited on the surface. In some instances, at least one hydrophilic polymer layer comprises a plurality of covalently-attached oligonucleotide adapter or primer molecules. In some instances, at least two, at least three, at least four, or at least five layers of hydrophilic polymer comprise a plurality of covalently-attached adapter or primer molecules.

The choice of polymer(s) used, the number of layers, the degree of cross-linking within and between layers, the number of layers comprising covalently-attached oligonucleotide adapter or primer molecules, and the local concentration or surface density of oligonucleotide adapter or primer molecules may be individually or collectively adjusted to "tune" the properties of the surface to achieve a desired surface wettability (as indicated, for example, by a water contact angle of less than 50 degrees), a desired surface stability under prolonged exposure to sequencing/genotyping reagents and repeated thermocycling, which often require temperature ramps at a peak temperature of at least 95 degrees C. and held for at least 5 minutes and cycled multiple times of at least 30 cycles, and a desired surface density of oligonucleotide adapter or primer molecules (e.g., at least 1,000 adapter or primer molecules per $\mu m^2$), which in turn provide for extremely low non-specific binding of dye molecules or other labeled sequencing/genotyping reagents, improved hybridization efficiency, improved amplification efficiency and specificity, optimal densities of clonally-amplified target sequences (in terms of the number of clonal colonies per unit area, the number of copies of target sequence per unit area, or the number of amplified target molecules per unit area), higher contrast-to-noise ratios (CNRs) in images (e.g., fluorescence images) of the support surface (e.g., CNR>20), and ultimately, improved detection accuracy or base-calling accuracy in genotyping and sequencing applications.

Example 17—Acrylate Coupled Surfaces

Plasma treated, KOH treated, or plasma/KOH treated glass surfaces or silicon wafers, or plasma treated COP surfaces were treated with (3-acrylopropyl) trimethoxysilane followed by incubation with bifunctional acrylate-PEG-NHS with average PEG molecular weights varying from 1K to 6K, including especially PEG-3.4K. Molecular weights of 500-10K were contemplated, with the limitation that the PEG had to be soluble in water at 42° C., soluble in water at 37° C., soluble in water at room temperature, in a liquid state at 42° C., in a liquid state at 37° C., or in a liquid state at room temperature. The PEG incorporation was optionally assisted by the addition of up to 0.5% (w/w) 2-hydroxy-2-methyl propiophenone, followed by UV treatment (10 minutes at 3.0 mW/cm2). Acrylate-PEG-NHS was used at concentrations of 3 mM and 6 mM, with superior results being achieved with 6 mM acrylate-PEG-NHS. After washing to remove unbound polymer, surfaces were incubated at room temperature for a sufficient time to allow the autolysis of the NHS groups, leaving free terminal carboxylate groups on the bound PEG molecules. These surfaces were then activated by treatment with EDAC-HCl, and 5'-amino oligonucleotides were added to yield the oligonucleotide conjugated surface. A combination of SP6 oligonucleotide (25NT) and SP5P oligonucleotide (a 25NT with a 3' phosphate cap) were added in a 1:1 ratio, or a 1:2, 1:5, or 1:10 ratio (SP6 oligonucleotide is a primer for surface-grown rolling circle amplification, while SP5P helps to prevent random priming events or nonspecific condensation/binding of RCA amplified products). After washing with 90% EtOH in MES at pH 9 to remove unbound oligonucleotide, a storage buffer was added comprising ACES/KCFEDTA/Tween20. Surfaces may be stored for at least 7 days under this buffer condition.

Surfaces comprising attached primers were then used for on-surface rolling circle amplification of target nucleic acids, yielding condensed nucleic acid molecules as shown elsewhere herein. Pre-prepared RCA products were also bound to the surface, yielding similarly compact nucleic acid structures.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in any combination in practicing the invention. It is intended that the following claims define the scope of the invention and that methods and structures within the scope of these claims and their equivalents be covered thereby.

We claim:

1. A method of detecting a nucleotide binding reaction or nucleotide incorporation reaction on a nucleic acid sequencing surface, the method comprising:
   (a) providing a surface that is passivated, wherein the surface comprises (i) at least one polymer coating layer adjacent to the surface, and (ii) a plurality of nucleic acid molecules coupled to at least one polymer coating layer, wherein at least one discrete region of the surface comprises a plurality of sample nucleic acid molecules hybridized to the plurality of nucleic acid molecules, and wherein the plurality of sample nucleic acid molecules are present at a density of at least 10,000/mm$^2$ of the surface; and
   (b) performing at least a nucleotide binding reaction or a nucleotide incorporation reaction with a nucleotide that is labeled with a detectable tag and a sample nucleic acid molecule of the plurality of sample nucleic acid molecules or derivative thereof,
   wherein an image of the surface exhibits a contrast to noise ratio (CNR) of at least 20 when the image of the surface following the nucleotide binding reaction or the nucleotide incorporation reaction of (b) is obtained.

2. The method of claim 1, further comprising, prior to (b), hybridizing the plurality of sample nucleic acid molecules to the plurality of nucleic acid molecules.

3. The method of claim 2, further comprising amplifying the plurality of sample nucleic acid molecules prior to hybridizing the plurality of sample nucleic acid molecules to the plurality of nucleic acid molecules.

4. The method of claim 3, wherein amplifying comprises performing a bridge amplification reaction on the plurality of sample nucleic acid molecules.

5. The method of claim 3, wherein the amplifying comprises performing a rolling circle amplification (RCA) reaction on the plurality of sample nucleic acid molecules.

6. The method of claim 3, wherein the amplifying comprises performing a helicase-dependent amplification reaction on the plurality of sample nucleic acid molecules.

7. The method of claim 3, wherein the amplifying comprises performing a recombinase-dependent amplification reaction on the plurality of sample nucleic acid molecules.

8. The method of claim 3, where the amplifying comprises a hybrid (1) of rolling circle amplification and (2) multi-strand displacement amplification or bridge amplification, on the plurality of sample nucleic acid molecules.

9. The method of claim 1, wherein the at least one polymer coating layer is hydrophilic.

10. The method of claim 1, wherein the at least one polymer coating layer comprises a molecule selected from the group consisting of polyethylene glycol (PEG), poly(vinyl alcohol) (PVA), poly(vinyl pyridine), poly(vinyl pyrrolidone) (PVP), poly(acrylic acid) (PAA), polyacrylamide, poly(N-isopropylacrylamide) (PNIPAM), poly(methyl methacrylate) (PMA), poly(2-hydroxyethyl methacrylate) (PHEMA), poly(oligo(ethylene glycol) methyl ether methacrylate) (POEGMA), polyglutamic acid (PGA), poly-lysine, poly-glucoside, streptavidin, and dextran.

11. The method of claim 10, wherein the at least one polymer coating layer comprises PEG.

12. The method of claim 1, wherein the surface comprises a second hydrophilic polymer coating layer.

13. The method of claim 1, wherein the at least one polymer coating layer comprises a polymer having a molecular weight of at least 1,000 Daltons.

14. The method of claim 1, wherein the at least one polymer layer comprises a branched hydrophilic polymer having at least 4 branches.

15. The method of claim 1, wherein at least one of the plurality of nucleic acid molecules comprises a sequence that includes a polymerase stop point.

16. The method of claim 2, wherein hybridizing the plurality of sample nucleic acid molecules to the plurality of nucleic acid molecules is performed by contacting the surface with the plurality of sample nucleic acid molecules at a concentration of no greater than 100 nM.

17. The method of claim 16, wherein hybridizing the plurality of sample nucleic acid molecules to the plurality of nucleic acid molecules is performed by contacting the surface with the sample nucleic acid molecules at a concentration of no greater than 10 nM.

18. The method of claim 3, wherein amplifying the plurality of sample nucleic acid molecules comprises clonally-amplifying the plurality of sample nucleic acid molecules prior to hybridizing to the plurality of nucleic acid molecules.

19. The method of claim 2, further comprising amplifying the plurality of sample nucleic acid molecules after hybridizing the plurality of sample nucleic acid molecules to the plurality of nucleic acid molecules.

20. The method of claim 1, wherein at least one of the plurality of sample nucleic acid molecules comprises a single-stranded or double stranded multimeric nucleic acid molecule comprising repeats of a regularly occurring monomer unit.

21. The method of claim 1, wherein at least one of the plurality of sample nucleic acid molecules comprises a concatemer.

22. The method of claim 1, wherein the surface density of the plurality of sample nucleic acid molecules is greater than a surface density of the plurality of nucleic acid molecules on the surface.

23. The method of claim 1, wherein the surface is positioned on an interior of a flow channel, flow cell, or capillary lumen.

24. The method of claim 23, wherein the flow channel, flow cell, or capillary lumen are configured for use in performing a nucleic acid hybridization, amplification, or sequencing reaction, or any combination thereof.

25. The method of claim 3, wherein an intensity of background light measured at a region of the surface that is laterally-displaced from the at least one discrete region is no more than twice an intensity measured at the at least one discrete region prior to the amplifying.

26. The method of claim 1, wherein the surface comprises:
   a) a first layer comprising a first monolayer of polymer molecules tethered to the surface;

b) a second layer comprising a second monolayer of polymer molecules tethered to the first monolayer of polymer molecules; and c) a third layer comprising a third monolayer of polymer molecules tethered to the second monolayer of polymer molecules, wherein the polymer molecules of the first layer, the second layer or the third layer comprises branched polymer molecules.

27. The method of claim 1, wherein the surface is part of a substrate comprising glass or plastic.

28. The method of claim 1, wherein (b) comprises performing the nucleotide binding reaction.

29. The method of claim 1, wherein an intensity of light measured at the at least one discrete region of the surface that comprises the sample nucleic acid molecule is at least 3× greater than the intensity of light measured at the same discrete region of the surface in the absence of said sample nucleic acid molecule.

30. The method of claim 1, wherein when the image is obtained, it is obtained using an inverted microscope and a camera under non-signal saturating conditions while the surface is immersed in a buffer, and wherein the detectable tag is Cyanine dye 3 (Cy3).

* * * * *